United States Patent
Partch et al.

(10) Patent No.: US 12,385,914 B2
(45) Date of Patent: Aug. 12, 2025

(54) CRY1-CLOCK-BMAL1 COMPLEX-DISRUPTING AGENTS AND METHODS OF IDENTIFYING AND USING SAME

(71) Applicant: The Regents of the University of California, Oakland, CA (US)

(72) Inventors: Carrie Partch, Santa Cruz, CA (US); Alicia Michael, Santa Cruz, CA (US); Jennifer Fribourgh, Santa Cruz, CA (US); Gian Carlo G. Parico, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 1663 days.

(21) Appl. No.: 16/475,960

(22) PCT Filed: Jan. 9, 2018

(86) PCT No.: PCT/US2018/012976
§ 371 (c)(1),
(2) Date: Jul. 3, 2019

(87) PCT Pub. No.: WO2018/132383
PCT Pub. Date: Jul. 19, 2018

(65) Prior Publication Data
US 2019/0324032 A1    Oct. 24, 2019

Related U.S. Application Data

(60) Provisional application No. 62/444,691, filed on Jan. 10, 2017.

(51) Int. Cl.
*G01N 33/53* (2006.01)
*G01N 21/64* (2006.01)
*G01N 33/566* (2006.01)
*G01N 33/68* (2006.01)

(52) U.S. Cl.
CPC ....... *G01N 33/566* (2013.01); *G01N 21/6428* (2013.01); *G01N 33/6872* (2013.01); *G01N 2021/6439* (2013.01); *G01N 2500/02* (2013.01); *G01N 2500/20* (2013.01)

(58) Field of Classification Search
None
See application file for complete search history.

(56) References Cited

U.S. PATENT DOCUMENTS

2003/0059848 A1* 3/2003 Reppert ............... C12Q 1/6897
435/7.1
2015/0284362 A1* 10/2015 Bersot ................. A61P 19/10
435/6.12

OTHER PUBLICATIONS

Birky et al. (2014) "The contribution of circadian rhythms to cancer formation and mortality" Atlas of Genetics and Cytogenetics in Oncology and Haematology, 18(2):133-145.
Czarna et al. (2013) "Structures of *Drosophila* cryptochrome and mouse cryptochrome1 provide insight into circadian function" Cell, 153:1394-1405.
Gustafson et al. (2015) "Emerging models for the molecular basis of mammalian circadian timing" Biochemistry, 54:134-149.
Michael (2016) "Molecular clockwork: integrative approaches unveil the first picture of a critical circadian transcriptional repressive complex" UCSD Center for Circadian Biology, 95 pgs.
Michael et al. (2017) "Format ion of a repressive complex in the mammalian circadian clock is mediated by the secondary pocket of CRY1" PNAS, 114(7):1560-1565.
Partch (2016) "Competitive mechanisms control the architecture of circadian regulatory complexes" UCSD Center for Circadian Biology, 23 pgs.
Ye et al. (2011) "Biochemical analysis of the canonical model for the mammalian circadian clock" The Journal of Biological Chemistry, 286(29):25891-25902.
Ahmad et al. (1998) "The CRY1 blue light photoreceptor of *Arabidopsis* interacts with phytochrome A in vitro" Molecular Cell, 1:939-948.

* cited by examiner

*Primary Examiner* — Michael D Pak
(74) *Attorney, Agent, or Firm* — Brian E. Davy; Bozicevic, Field & Francis LLP

(57) ABSTRACT

Provided are agents that disrupt CRY1-CLOCK-BMAL1 ternary complexes. In certain aspects, the agents bind to the secondary pocket of CRY1 and inhibit interaction between the secondary pocket and the PAS-B domain of CLOCK, to disrupt CRY1-CLOCK-BMAL1 ternary complexes. Also provided are methods for identifying such agents, compositions including such agents, and therapeutic methods employing such agents.

13 Claims, 15 Drawing Sheets
Specification includes a Sequence Listing.

SEQUENCE LISTING

```
<160> NUMBER OF SEQ ID NOS: 14

<210> SEQ ID NO 1
<211> LENGTH: 606
<212> TYPE: PRT
<213> ORGANISM: Mus musculus

<400> SEQUENCE: 1

Met Gly Val Asn Ala Val His Trp Phe Arg Lys Gly Leu Arg Leu His
1               5                   10                  15

Asp Asn Pro Ala Leu Lys Glu Cys Ile Gln Gly Ala Asp Thr Ile Arg
                20                  25                  30

Cys Val Tyr Ile Leu Asp Pro Trp Phe Ala Gly Ser Ser Asn Val Gly
            35                  40                  45

Ile Asn Arg Trp Arg Phe Leu Leu Gln Cys Leu Glu Asp Leu Asp Ala
        50                  55                  60

Asn Leu Arg Lys Leu Asn Ser Arg Leu Phe Val Ile Arg Gly Gln Pro
65                  70                  75                  80

Ala Asp Val Phe Pro Arg Leu Phe Lys Glu Trp Asn Ile Thr Lys Leu
                85                  90                  95

Ser Ile Glu Tyr Asp Ser Glu Pro Phe Gly Lys Glu Arg Asp Ala Ala
                100                 105                 110

Ile Lys Lys Leu Ala Thr Glu Ala Gly Val Glu Val Ile Val Arg Ile
            115                 120                 125

Ser His Thr Leu Tyr Asp Leu Asp Lys Ile Ile Glu Leu Asn Gly Gly
        130                 135                 140

Gln Pro Pro Leu Thr Tyr Lys Arg Phe Gln Thr Leu Val Ser Lys Met
145                 150                 155                 160

Glu Pro Leu Glu Met Pro Ala Asp Thr Ile Thr Ser Asp Val Ile Gly
                165                 170                 175

Lys Cys Met Thr Pro Leu Ser Asp His Asp Glu Lys Tyr Gly Val
                180                 185                 190

Pro Ser Leu Glu Glu Leu Gly Phe Asp Thr Asp Gly Leu Ser Ser Ala
            195                 200                 205

Val Trp Pro Gly Gly Glu Thr Glu Ala Leu Thr Arg Leu Glu Arg His
        210                 215                 220

Leu Glu Arg Lys Ala Trp Val Ala Asn Phe Glu Arg Pro Arg Met Asn
225                 230                 235                 240

Ala Asn Ser Leu Leu Ala Ser Pro Thr Gly Leu Ser Pro Tyr Leu Arg
                245                 250                 255
```

Phe Gly Cys Leu Ser Cys Arg Leu Phe Tyr Phe Lys Leu Thr Asp Leu
                260                 265                 270

Tyr Lys Lys Val Lys Lys Asn Ser Pro Pro Leu Ser Leu Tyr Gly
            275                 280                 285

Gln Leu Leu Trp Arg Glu Phe Phe Tyr Thr Ala Ala Thr Asn Asn Pro
290                 295                 300

Arg Phe Asp Lys Met Glu Gly Asn Pro Ile Cys Val Gln Ile Pro Trp
305                 310                 315                 320

Asp Lys Asn Pro Glu Ala Leu Ala Lys Trp Ala Gly Arg Thr Gly
            325                 330                 335

Phe Pro Trp Ile Asp Ala Ile Met Thr Gln Leu Arg Gln Glu Gly Trp
            340                 345                 350

Ile His His Leu Ala Arg His Ala Val Ala Cys Phe Leu Thr Arg Gly
            355                 360                 365

Asp Leu Trp Ile Ser Trp Glu Glu Gly Met Lys Val Phe Glu Glu Leu
            370                 375                 380

Leu Leu Asp Ala Asp Trp Ser Ile Asn Ala Gly Ser Trp Met Trp Leu
385                 390                 395                 400

Ser Cys Ser Ser Phe Phe Gln Gln Phe Phe His Cys Tyr Cys Pro Val
                405                 410                 415

Gly Phe Gly Arg Arg Thr Asp Pro Asn Gly Asp Tyr Ile Arg Arg Tyr
            420                 425                 430

Leu Pro Val Leu Arg Gly Phe Pro Ala Lys Tyr Ile Tyr Asp Pro Trp
            435                 440                 445

Asn Ala Pro Glu Gly Ile Gln Lys Val Ala Lys Cys Leu Ile Gly Val
450                 455                 460

Asn Tyr Pro Lys Pro Met Val Asn His Ala Glu Ala Ser Arg Leu Asn
465                 470                 475                 480

Ile Glu Arg Met Lys Gln Ile Tyr Gln Gln Leu Ser Arg Tyr Arg Gly
            485                 490                 495

Leu Gly Leu Leu Ala Ser Val Pro Ser Asn Ser Asn Gly Asn Gly Gly
            500                 505                 510

Leu Met Gly Tyr Ala Pro Gly Glu Asn Val Pro Ser Cys Ser Ser Ser
            515                 520                 525

Gly Asn Gly Gly Leu Met Gly Tyr Ala Pro Gly Glu Asn Val Pro Ser
            530                 535                 540

Cys Ser Gly Gly Asn Cys Ser Gln Gly Ser Gly Ile Leu His Tyr Ala
545                 550                 555                 560

His Gly Asp Ser Gln Gln Thr His Ser Leu Lys Gln Gly Arg Ser Ser
                565                 570                 575

Ala Gly Thr Gly Leu Ser Ser Gly Lys Arg Pro Ser Gln Glu Glu Asp
            580                 585                 590

Ala Gln Ser Val Gly Pro Lys Val Gln Arg Gln Ser Ser Asn
            595                 600                 605

<210> SEQ ID NO 2
<211> LENGTH: 855
<212> TYPE: PRT
<213> ORGANISM: Mus musculus

<400> SEQUENCE: 2

Met Val Phe Thr Val Ser Cys Ser Lys Met Ser Ser Ile Val Asp Arg
1               5                   10                  15

Asp Asp Ser Ser Ile Phe Asp Gly Leu Val Glu Glu Asp Asp Lys Asp

```
                20                  25                  30
Lys Ala Lys Arg Val Ser Arg Asn Lys Ser Glu Lys Lys Arg Arg Asp
            35                  40                  45
Gln Phe Asn Val Leu Ile Lys Glu Leu Gly Ser Met Leu Pro Gly Asn
            50                  55                  60
Ala Arg Lys Met Asp Lys Ser Thr Val Leu Gln Lys Ser Ile Asp Phe
65                  70                  75                  80
Leu Arg Lys His Lys Glu Thr Thr Ala Gln Ser Asp Ala Ser Glu Ile
                85                  90                  95
Arg Gln Asp Trp Lys Pro Thr Phe Leu Ser Asn Glu Glu Phe Thr Gln
            100                 105                 110
Leu Met Leu Glu Ala Leu Asp Gly Phe Phe Leu Ala Ile Met Thr Asp
            115                 120                 125
Gly Ser Ile Ile Tyr Val Ser Glu Ser Val Thr Ser Leu Leu Glu His
            130                 135                 140
Leu Pro Ser Asp Leu Val Asp Gln Ser Ile Phe Asn Phe Ile Pro Glu
145                 150                 155                 160
Gly Glu His Ser Glu Val Tyr Lys Ile Leu Ser Thr His Leu Leu Glu
                165                 170                 175
Ser Asp Ser Leu Thr Pro Glu Tyr Leu Lys Ser Lys Asn Gln Leu Glu
            180                 185                 190
Phe Cys Cys His Met Leu Arg Gly Thr Ile Asp Pro Lys Glu Pro Ser
            195                 200                 205
Thr Tyr Glu Tyr Val Arg Phe Ile Gly Asn Phe Lys Ser Leu Thr Ser
            210                 215                 220
Val Ser Thr Ser Thr His Asn Gly Phe Glu Gly Thr Ile Gln Arg Thr
225                 230                 235                 240
His Arg Pro Ser Tyr Glu Asp Arg Val Cys Phe Val Ala Thr Val Arg
                245                 250                 255
Leu Ala Thr Pro Gln Phe Ile Lys Glu Met Cys Thr Val Glu Glu Pro
            260                 265                 270
Asn Glu Glu Phe Thr Ser Arg His Ser Leu Glu Trp Lys Phe Leu Phe
            275                 280                 285
Leu Asp His Arg Ala Pro Pro Ile Ile Gly Tyr Leu Pro Phe Glu Val
            290                 295                 300
Leu Gly Thr Ser Gly Tyr Asp Tyr Tyr His Val Asp Asp Leu Glu Asn
305                 310                 315                 320
Leu Ala Lys Cys His Glu His Leu Met Gln Tyr Gly Lys Gly Lys Ser
                325                 330                 335
Cys Tyr Tyr Arg Phe Leu Thr Lys Gly Gln Gln Trp Ile Trp Leu Gln
            340                 345                 350
Thr His Tyr Tyr Ile Thr Tyr His Gln Trp Asn Ser Arg Pro Glu Phe
            355                 360                 365
Ile Val Cys Thr His Thr Val Val Ser Tyr Ala Glu Val Arg Ala Glu
            370                 375                 380
Arg Arg Arg Glu Leu Gly Ile Glu Glu Ser Leu Pro Glu Thr Ala Ala
385                 390                 395                 400
Asp Lys Ser Gln Asp Ser Gly Ser Asp Asn Arg Ile Asn Thr Val Ser
                405                 410                 415
Leu Lys Glu Ala Leu Glu Arg Phe Asp His Ser Pro Thr Pro Ser Ala
            420                 425                 430
Ser Ser Arg Ser Ser Arg Lys Ser Ser His Thr Ala Val Ser Asp Pro
            435                 440                 445
```

```
Ser Ser Thr Pro Thr Lys Ile Pro Thr Asp Thr Ser Thr Pro Pro Arg
    450                 455                 460
Gln His Leu Pro Ala His Glu Lys Met Thr Gln Arg Arg Ser Ser Phe
465                 470                 475                 480
Ser Ser Gln Ser Ile Asn Ser Gln Ser Val Gly Pro Ser Leu Thr Gln
                485                 490                 495
Pro Ala Met Ser Gln Ala Ala Asn Leu Pro Ile Pro Gln Gly Met Ser
            500                 505                 510
Gln Phe Gln Phe Ser Ala Gln Leu Gly Ala Met Gln His Leu Lys Asp
        515                 520                 525
Gln Leu Glu Gln Arg Thr Arg Met Ile Glu Ala Asn Ile His Arg Gln
    530                 535                 540
Gln Glu Glu Leu Arg Lys Ile Gln Glu Gln Leu Gln Met Val His Gly
545                 550                 555                 560
Gln Gly Leu Gln Met Phe Leu Gln Gln Ser Asn Pro Gly Leu Asn Phe
                565                 570                 575
Gly Ser Val Gln Leu Ser Ser Gly Asn Ser Asn Ile Gln Gln Leu Thr
            580                 585                 590
Pro Val Asn Met Gln Gly Gln Val Val Pro Ala Asn Gln Val Gln Ser
        595                 600                 605
Gly His Ile Ser Thr Gly Gln His Met Ile Gln Gln Gln Thr Leu Gln
    610                 615                 620
Ser Thr Ser Thr Gln Gln Ser Gln Gln Ser Val Met Ser Gly His Ser
625                 630                 635                 640
Gln Gln Thr Ser Leu Pro Ser Gln Thr Pro Ser Thr Leu Thr Ala Pro
                645                 650                 655
Leu Tyr Asn Thr Met Val Ile Ser Gln Pro Ala Ala Gly Ser Met Val
            660                 665                 670
Gln Ile Pro Ser Ser Met Pro Gln Asn Ser Thr Gln Ser Ala Thr Val
        675                 680                 685
Thr Thr Phe Thr Gln Asp Arg Gln Ile Arg Phe Ser Gln Gly Gln Gln
    690                 695                 700
Leu Val Thr Lys Leu Val Thr Ala Pro Val Ala Cys Gly Ala Val Met
705                 710                 715                 720
Val Pro Ser Thr Met Leu Met Gly Gln Val Val Thr Ala Tyr Pro Thr
                725                 730                 735
Phe Ala Thr Gln Gln Gln Ala Gln Thr Leu Ser Val Thr Gln Gln
            740                 745                 750
Gln Gln Gln Gln Gln Gln Pro Gln Gln Gln Gln Gln Gln Gln
        755                 760                 765
Gln Ser Ser Gln Glu Gln Gln Leu Pro Ser Val Gln Gln Pro Ala Gln
    770                 775                 780
Ala Gln Leu Gly Gln Pro Gln Gln Phe Leu Gln Thr Ser Arg Leu
785                 790                 795                 800
Leu His Gly Asn Pro Ser Thr Gln Leu Ile Leu Ser Ala Ala Phe Pro
                805                 810                 815
Leu Gln Gln Ser Thr Phe Pro Pro Ser His Gln Gln His Gln Pro
            820                 825                 830
Gln Gln Gln Gln Gln Leu Pro Arg His Arg Thr Asp Ser Leu Thr Asp
        835                 840                 845
Pro Ser Lys Val Gln Pro Gln
    850                 855
```

<210> SEQ ID NO 3
<211> LENGTH: 632
<212> TYPE: PRT
<213> ORGANISM: Mus musculus

<400> SEQUENCE: 3

Met Ala Asp Gln Arg Met Asp Ile Ser Ser Thr Ile Ser Asp Phe Met
1               5                   10                  15

Ser Pro Gly Pro Thr Asp Leu Leu Ser Gly Ser Leu Gly Thr Ser Gly
            20                  25                  30

Val Asp Cys Asn Arg Lys Arg Lys Gly Ser Ala Thr Asp Tyr Gln Leu
        35                  40                  45

Asp Asp Phe Ala Phe Glu Glu Ser Met Asp Thr Asp Lys Asp Asp Pro
    50                  55                  60

His Gly Arg Leu Glu Tyr Ala Glu His Gln Gly Arg Ile Lys Asn Ala
65                  70                  75                  80

Arg Glu Ala His Ser Gln Ile Glu Lys Arg Arg Arg Asp Lys Met Asn
                85                  90                  95

Ser Phe Ile Asp Glu Leu Ala Ser Leu Val Pro Thr Cys Asn Ala Met
            100                 105                 110

Ser Arg Lys Leu Asp Lys Leu Thr Val Leu Arg Met Ala Val Gln His
        115                 120                 125

Met Lys Thr Leu Arg Gly Ala Thr Asn Pro Tyr Thr Glu Ala Asn Tyr
    130                 135                 140

Lys Pro Thr Phe Leu Ser Asp Asp Glu Leu Lys His Leu Ile Leu Arg
145                 150                 155                 160

Ala Ala Asp Gly Phe Leu Phe Val Val Gly Cys Asp Arg Gly Lys Ile
                165                 170                 175

Leu Phe Val Ser Glu Ser Val Phe Lys Ile Leu Asn Tyr Ser Gln Asn
            180                 185                 190

Asp Leu Ile Gly Gln Ser Leu Phe Asp Tyr Leu His Pro Lys Asp Ile
        195                 200                 205

Ala Lys Val Lys Glu Gln Leu Ser Ser Ser Asp Thr Ala Pro Arg Glu
    210                 215                 220

Arg Leu Ile Asp Ala Lys Thr Gly Leu Pro Val Lys Thr Asp Ile Thr
225                 230                 235                 240

Pro Gly Pro Ser Arg Leu Cys Ser Gly Ala Arg Arg Ser Phe Phe Cys
                245                 250                 255

Arg Met Lys Cys Asn Arg Pro Ser Val Lys Val Glu Asp Lys Asp Phe
            260                 265                 270

Ala Ser Thr Cys Ser Lys Lys Asp Arg Lys Ser Phe Cys Thr Ile
        275                 280                 285

His Ser Thr Gly Tyr Leu Lys Ser Trp Pro Pro Thr Lys Met Gly Leu
    290                 295                 300

Asp Glu Asp Asn Glu Pro Asp Asn Glu Gly Cys Asn Leu Ser Cys Leu
305                 310                 315                 320

Val Ala Ile Gly Arg Leu His Ser His Met Val Pro Gln Pro Ala Asn
                325                 330                 335

Gly Glu Ile Arg Val Lys Ser Met Glu Tyr Val Ser Arg His Ala Ile
            340                 345                 350

Asp Gly Lys Phe Val Phe Val Asp Gln Arg Ala Thr Ala Ile Leu Ala
        355                 360                 365

Tyr Leu Pro Gln Glu Leu Leu Gly Thr Ser Cys Tyr Glu Tyr Phe His
    370                 375                 380

Gln Asp Asp Ile Gly His Leu Ala Glu Cys His Arg Gln Val Leu Gln
385                 390                 395                 400

Thr Arg Glu Lys Ile Thr Thr Asn Cys Tyr Lys Phe Lys Ile Lys Asp
            405                 410                 415

Gly Ser Phe Ile Thr Leu Arg Ser Arg Trp Phe Ser Phe Met Asn Pro
            420                 425                 430

Trp Thr Lys Glu Val Glu Tyr Ile Val Ser Thr Asn Thr Val Val Leu
        435                 440                 445

Ala Asn Val Leu Glu Gly Gly Asp Pro Thr Phe Pro Gln Leu Thr Ala
450                 455                 460

Pro Pro His Ser Met Asp Ser Met Leu Pro Ser Gly Glu Gly Gly Pro
465                 470                 475                 480

Lys Arg Thr His Pro Thr Val Pro Gly Ile Pro Gly Gly Thr Arg Ala
                485                 490                 495

Gly Ala Gly Lys Ile Gly Arg Met Ile Ala Glu Glu Ile Met Glu Ile
            500                 505                 510

His Arg Ile Arg Gly Ser Ser Pro Ser Cys Gly Ser Ser Pro Leu
        515                 520                 525

Asn Ile Thr Ser Thr Pro Pro Asp Ala Ser Ser Pro Gly Gly Lys
530                 535                 540

Lys Ile Leu Asn Gly Gly Thr Pro Asp Ile Pro Ser Thr Gly Leu Leu
545                 550                 555                 560

Pro Gly Gln Ala Gln Glu Thr Pro Gly Tyr Pro Tyr Ser Asp Ser Ser
            565                 570                 575

Ser Ile Leu Gly Glu Asn Pro His Ile Gly Ile Asp Met Ile Asp Asn
        580                 585                 590

Asp Gln Gly Ser Ser Ser Pro Ser Asn Asp Glu Ala Ala Met Ala Val
            595                 600                 605

Ile Met Ser Leu Leu Glu Ala Asp Ala Gly Leu Gly Gly Pro Val Asp
    610                 615                 620

Phe Ser Asp Leu Pro Trp Pro Leu
625                 630

<210> SEQ ID NO 4
<211> LENGTH: 586
<212> TYPE: PRT
<213> ORGANISM: Homo sapiens

<400> SEQUENCE: 4

Met Gly Val Asn Ala Val His Trp Phe Arg Lys Gly Leu Arg Leu His
1               5                   10                  15

Asp Asn Pro Ala Leu Lys Glu Cys Ile Gln Gly Ala Asp Thr Ile Arg
            20                  25                  30

Cys Val Tyr Ile Leu Asp Pro Trp Phe Ala Gly Ser Ser Asn Val Gly
        35                  40                  45

Ile Asn Arg Trp Arg Phe Leu Leu Gln Cys Leu Glu Asp Leu Asp Ala
    50                  55                  60

Asn Leu Arg Lys Leu Asn Ser Arg Leu Phe Val Ile Arg Gly Gln Pro
65                  70                  75                  80

Ala Asp Val Phe Pro Arg Leu Phe Lys Glu Trp Asn Ile Thr Lys Leu
                85                  90                  95

Ser Ile Glu Tyr Asp Ser Glu Pro Phe Gly Lys Glu Arg Asp Ala Ala
            100                 105                 110

Ile Lys Lys Leu Ala Thr Glu Ala Gly Val Glu Val Ile Val Arg Ile

```
            115                 120                 125
Ser His Thr Leu Tyr Asp Leu Asp Lys Ile Ile Glu Leu Asn Gly Gly
130                 135                 140

Gln Pro Pro Leu Thr Tyr Lys Arg Phe Gln Thr Leu Ile Ser Lys Met
145                 150                 155                 160

Glu Pro Leu Glu Ile Pro Val Glu Thr Ile Thr Ser Glu Val Ile Glu
                165                 170                 175

Lys Cys Thr Thr Pro Leu Ser Asp Asp His Asp Glu Lys Tyr Gly Val
            180                 185                 190

Pro Ser Leu Glu Glu Leu Gly Phe Asp Thr Asp Gly Leu Ser Ser Ala
        195                 200                 205

Val Trp Pro Gly Gly Glu Thr Glu Ala Leu Thr Arg Leu Glu Arg His
    210                 215                 220

Leu Glu Arg Lys Ala Trp Val Ala Asn Phe Glu Arg Pro Arg Met Asn
225                 230                 235                 240

Ala Asn Ser Leu Leu Ala Ser Pro Thr Gly Leu Ser Pro Tyr Leu Arg
                245                 250                 255

Phe Gly Cys Leu Ser Cys Arg Leu Phe Tyr Phe Lys Leu Thr Asp Leu
            260                 265                 270

Tyr Lys Lys Val Lys Lys Asn Ser Pro Pro Leu Ser Leu Tyr Gly
        275                 280                 285

Gln Leu Leu Trp Arg Glu Phe Phe Tyr Thr Ala Ala Thr Asn Asn Pro
    290                 295                 300

Arg Phe Asp Lys Met Glu Gly Asn Pro Ile Cys Val Gln Ile Pro Trp
305                 310                 315                 320

Asp Lys Asn Pro Glu Ala Leu Ala Lys Trp Ala Glu Gly Arg Thr Gly
                325                 330                 335

Phe Pro Trp Ile Asp Ala Ile Met Thr Gln Leu Arg Gln Glu Gly Trp
            340                 345                 350

Ile His His Leu Ala Arg His Ala Val Ala Cys Phe Leu Thr Arg Gly
        355                 360                 365

Asp Leu Trp Ile Ser Trp Glu Glu Gly Met Lys Val Phe Glu Glu Leu
    370                 375                 380

Leu Leu Asp Ala Asp Trp Ser Ile Asn Ala Gly Ser Trp Met Trp Leu
385                 390                 395                 400

Ser Cys Ser Ser Phe Phe Gln Gln Phe Phe His Cys Tyr Cys Pro Val
                405                 410                 415

Gly Phe Gly Arg Arg Thr Asp Pro Asn Gly Asp Tyr Ile Arg Arg Tyr
            420                 425                 430

Leu Pro Val Leu Arg Gly Phe Pro Ala Lys Tyr Ile Tyr Asp Pro Trp
        435                 440                 445

Asn Ala Pro Glu Gly Ile Gln Lys Val Ala Lys Cys Leu Ile Gly Val
    450                 455                 460

Asn Tyr Pro Lys Pro Met Val Asn His Ala Glu Ala Ser Arg Leu Asn
465                 470                 475                 480

Ile Glu Arg Met Lys Gln Ile Tyr Gln Gln Leu Ser Arg Tyr Arg Gly
                485                 490                 495

Leu Gly Leu Leu Ala Ser Val Pro Ser Asn Pro Asn Gly Asn Gly Gly
            500                 505                 510

Phe Met Gly Tyr Ser Ala Glu Asn Ile Pro Gly Cys Ser Ser Ser Gly
        515                 520                 525

Ser Cys Ser Gln Gly Ser Gly Ile Leu His Tyr Ala His Gly Asp Ser
    530                 535                 540
```

Gln Gln Thr His Leu Leu Lys Gln Gly Arg Ser Ser Met Gly Thr Gly
545                 550                 555                 560

Leu Ser Gly Gly Lys Arg Pro Ser Gln Glu Glu Asp Thr Gln Ser Ile
                565                 570                 575

Gly Pro Lys Val Gln Arg Gln Ser Thr Asn
            580                 585

<210> SEQ ID NO 5
<211> LENGTH: 846
<212> TYPE: PRT
<213> ORGANISM: Homo sapiens

<400> SEQUENCE: 5

Met Leu Phe Thr Val Ser Cys Ser Lys Met Ser Ser Ile Val Asp Arg
1               5                   10                  15

Asp Asp Ser Ser Ile Phe Asp Gly Leu Val Glu Glu Asp Asp Lys Asp
                20                  25                  30

Lys Ala Lys Arg Val Ser Arg Asn Lys Ser Glu Lys Lys Arg Arg Asp
            35                  40                  45

Gln Phe Asn Val Leu Ile Lys Glu Leu Gly Ser Met Leu Pro Gly Asn
50                  55                  60

Ala Arg Lys Met Asp Lys Ser Thr Val Leu Gln Lys Ser Ile Asp Phe
65                  70                  75                  80

Leu Arg Lys His Lys Glu Ile Thr Ala Gln Ser Asp Ala Ser Glu Ile
                85                  90                  95

Arg Gln Asp Trp Lys Pro Thr Phe Leu Ser Asn Glu Glu Phe Thr Gln
            100                 105                 110

Leu Met Leu Glu Ala Leu Asp Gly Phe Phe Leu Ala Ile Met Thr Asp
        115                 120                 125

Gly Ser Ile Ile Tyr Val Ser Glu Ser Val Thr Ser Leu Leu Glu His
130                 135                 140

Leu Pro Ser Asp Leu Val Asp Gln Ser Ile Phe Asn Phe Ile Pro Glu
145                 150                 155                 160

Gly Glu His Ser Glu Val Tyr Lys Ile Leu Ser Thr His Leu Leu Glu
                165                 170                 175

Ser Asp Ser Leu Thr Pro Glu Tyr Leu Lys Ser Lys Asn Gln Leu Glu
            180                 185                 190

Phe Cys Cys His Met Leu Arg Gly Thr Ile Asp Pro Lys Glu Pro Ser
        195                 200                 205

Thr Tyr Glu Tyr Val Lys Phe Ile Gly Asn Phe Lys Ser Leu Asn Ser
210                 215                 220

Val Ser Ser Ser Ala His Asn Gly Phe Glu Gly Thr Ile Gln Arg Thr
225                 230                 235                 240

His Arg Pro Ser Tyr Glu Asp Arg Val Cys Phe Val Ala Thr Val Arg
                245                 250                 255

Leu Ala Thr Pro Gln Phe Ile Lys Glu Met Cys Thr Val Glu Glu Pro
            260                 265                 270

Asn Glu Glu Phe Thr Ser Arg His Ser Leu Glu Trp Lys Phe Leu Phe
        275                 280                 285

Leu Asp His Arg Ala Pro Pro Ile Ile Gly Tyr Leu Pro Phe Glu Val
        290                 295                 300

Leu Gly Thr Ser Gly Tyr Asp Tyr Tyr His Val Asp Asp Leu Glu Asn
305                 310                 315                 320

Leu Ala Lys Cys His Glu His Leu Met Gln Tyr Gly Lys Gly Lys Ser

```
            325                 330                 335
Cys Tyr Tyr Arg Phe Leu Thr Lys Gly Gln Gln Trp Ile Trp Leu Gln
            340                 345                 350

Thr His Tyr Tyr Ile Thr Tyr His Gln Trp Asn Ser Arg Pro Glu Phe
            355                 360                 365

Ile Val Cys Thr His Thr Val Val Ser Tyr Ala Glu Val Arg Ala Glu
370                 375                 380

Arg Arg Arg Glu Leu Gly Ile Glu Glu Ser Leu Pro Glu Thr Ala Ala
385                 390                 395                 400

Asp Lys Ser Gln Asp Ser Gly Ser Asp Asn Arg Ile Asn Thr Val Ser
                405                 410                 415

Leu Lys Glu Ala Leu Glu Arg Phe Asp His Ser Pro Thr Pro Ser Ala
            420                 425                 430

Ser Ser Arg Ser Ser Arg Lys Ser Ser His Thr Ala Val Ser Asp Pro
            435                 440                 445

Ser Ser Thr Pro Thr Lys Ile Pro Thr Asp Thr Ser Thr Pro Pro Arg
450                 455                 460

Gln His Leu Pro Ala His Glu Lys Met Val Gln Arg Ser Ser Phe
465                 470                 475                 480

Ser Ser Gln Ser Ile Asn Ser Gln Ser Val Gly Ser Ser Leu Thr Gln
                485                 490                 495

Pro Val Met Ser Gln Ala Thr Asn Leu Pro Ile Pro Gln Gly Met Ser
            500                 505                 510

Gln Phe Gln Phe Ser Ala Gln Leu Gly Ala Met Gln His Leu Lys Asp
            515                 520                 525

Gln Leu Glu Gln Arg Thr Arg Met Ile Glu Ala Asn Ile His Arg Gln
            530                 535                 540

Gln Glu Glu Leu Arg Lys Ile Gln Glu Gln Leu Gln Met Val His Gly
545                 550                 555                 560

Gln Gly Leu Gln Met Phe Leu Gln Gln Ser Asn Pro Gly Leu Asn Phe
            565                 570                 575

Gly Ser Val Gln Leu Ser Ser Gly Asn Ser Ser Asn Ile Gln Gln Leu
            580                 585                 590

Ala Pro Ile Asn Met Gln Gly Gln Val Val Pro Thr Asn Gln Ile Gln
            595                 600                 605

Ser Gly Met Asn Thr Gly His Ile Gly Thr Thr Gln His Met Ile Gln
            610                 615                 620

Gln Gln Thr Leu Gln Ser Thr Ser Thr Gln Ser Gln Gln Asn Val Leu
625                 630                 635                 640

Ser Gly His Ser Gln Gln Thr Ser Leu Pro Ser Gln Thr Gln Ser Thr
                645                 650                 655

Leu Thr Ala Pro Leu Tyr Asn Thr Met Val Ile Ser Gln Pro Ala Ala
            660                 665                 670

Gly Ser Met Val Gln Ile Pro Ser Ser Met Pro Gln Asn Ser Thr Gln
            675                 680                 685

Ser Ala Ala Val Thr Thr Phe Thr Gln Asp Arg Gln Ile Arg Phe Ser
            690                 695                 700

Gln Gly Gln Gln Leu Val Thr Lys Leu Val Thr Ala Pro Val Ala Cys
705                 710                 715                 720

Gly Ala Val Met Val Pro Ser Thr Met Leu Met Gly Gln Val Val Thr
            725                 730                 735

Ala Tyr Pro Thr Phe Ala Thr Gln Gln Gln Gln Ser Gln Thr Leu Ser
            740                 745                 750
```

Val Thr Gln Gln Gln Gln Gln Ser Ser Gln Glu Gln Gln Leu Thr
            755                 760                 765

Ser Val Gln Gln Pro Ser Gln Ala Gln Leu Thr Gln Pro Pro Gln Gln
770                 775                 780

Phe Leu Gln Thr Ser Arg Leu Leu His Gly Asn Pro Ser Thr Gln Leu
785                 790                 795                 800

Ile Leu Ser Ala Ala Phe Pro Leu Gln Gln Ser Thr Phe Pro Gln Ser
                805                 810                 815

His His Gln Gln His Gln Ser Gln Gln Gln Gln Leu Ser Arg His
                820                 825                 830

Arg Thr Asp Ser Leu Pro Asp Pro Ser Lys Val Gln Pro Gln
            835                 840                 845

<210> SEQ ID NO 6
<211> LENGTH: 626
<212> TYPE: PRT
<213> ORGANISM: Homo sapiens

<400> SEQUENCE: 6

Met Ala Asp Gln Arg Met Asp Ile Ser Ser Thr Ile Ser Asp Phe Met
1               5                   10                  15

Ser Pro Gly Pro Thr Asp Leu Leu Ser Ser Ser Leu Gly Thr Ser Gly
                20                  25                  30

Val Asp Cys Asn Arg Lys Arg Lys Gly Ser Ser Thr Asp Tyr Gln Glu
            35                  40                  45

Ser Met Asp Thr Asp Lys Asp Pro His Gly Arg Leu Glu Tyr Thr
        50                  55                  60

Glu His Gln Gly Arg Ile Lys Asn Ala Arg Glu Ala His Ser Gln Ile
65                  70                  75                  80

Glu Lys Arg Arg Arg Asp Lys Met Asn Ser Phe Ile Asp Glu Leu Ala
                85                  90                  95

Ser Leu Val Pro Thr Cys Asn Ala Met Ser Arg Lys Leu Asp Lys Leu
            100                 105                 110

Thr Val Leu Arg Met Ala Val Gln His Met Lys Thr Leu Arg Gly Ala
        115                 120                 125

Thr Asn Pro Tyr Thr Glu Ala Asn Tyr Lys Pro Thr Phe Leu Ser Asp
    130                 135                 140

Asp Glu Leu Lys His Leu Ile Leu Arg Ala Ala Asp Gly Phe Leu Phe
145                 150                 155                 160

Val Val Gly Cys Asp Arg Gly Lys Ile Leu Phe Val Ser Glu Ser Val
                165                 170                 175

Phe Lys Ile Leu Asn Tyr Ser Gln Asn Asp Leu Ile Gly Gln Ser Leu
            180                 185                 190

Phe Asp Tyr Leu His Pro Lys Asp Ile Ala Lys Val Lys Glu Gln Leu
        195                 200                 205

Ser Ser Ser Asp Thr Ala Pro Arg Glu Arg Leu Ile Asp Ala Lys Thr
    210                 215                 220

Gly Leu Pro Val Lys Thr Asp Ile Thr Pro Gly Pro Ser Arg Leu Cys
225                 230                 235                 240

Ser Gly Ala Arg Arg Ser Phe Phe Cys Arg Met Lys Cys Asn Arg Pro
                245                 250                 255

Ser Val Lys Val Glu Asp Lys Asp Phe Pro Ser Thr Cys Ser Lys Lys
            260                 265                 270

Lys Ala Asp Arg Lys Ser Phe Cys Thr Ile His Ser Thr Gly Tyr Leu

```
                275                 280                 285
Lys Ser Trp Pro Pro Thr Lys Met Gly Leu Asp Glu Asp Asn Glu Pro
290                 295                 300

Asp Asn Glu Gly Cys Asn Leu Ser Cys Leu Val Ala Ile Gly Arg Leu
305                 310                 315                 320

His Ser His Val Val Pro Gln Pro Val Asn Gly Glu Ile Arg Val Lys
                325                 330                 335

Ser Met Glu Tyr Val Ser Arg His Ala Ile Asp Gly Lys Phe Val Phe
            340                 345                 350

Val Asp Gln Arg Ala Thr Ala Ile Leu Ala Tyr Leu Pro Gln Glu Leu
        355                 360                 365

Leu Gly Thr Ser Cys Tyr Glu Tyr Phe His Gln Asp Asp Ile Gly His
370                 375                 380

Leu Ala Glu Cys His Arg Gln Val Leu Gln Thr Arg Glu Lys Ile Thr
385                 390                 395                 400

Thr Asn Cys Tyr Lys Phe Lys Ile Lys Asp Gly Ser Phe Ile Thr Leu
                405                 410                 415

Arg Ser Arg Trp Phe Ser Phe Met Asn Pro Trp Thr Lys Glu Val Glu
            420                 425                 430

Tyr Ile Val Ser Thr Asn Thr Val Val Leu Ala Asn Val Leu Glu Gly
        435                 440                 445

Gly Asp Pro Thr Phe Pro Gln Leu Thr Ala Ser Pro His Ser Met Asp
450                 455                 460

Ser Met Leu Pro Ser Gly Glu Gly Gly Pro Lys Arg Thr His Pro Thr
465                 470                 475                 480

Val Pro Gly Ile Pro Gly Gly Thr Arg Ala Gly Ala Gly Lys Ile Gly
                485                 490                 495

Arg Met Ile Ala Glu Glu Ile Met Glu Ile His Arg Ile Arg Gly Ser
            500                 505                 510

Ser Pro Ser Ser Cys Gly Ser Ser Pro Leu Asn Ile Thr Ser Thr Pro
        515                 520                 525

Pro Pro Asp Ala Ser Ser Pro Gly Gly Lys Lys Ile Leu Asn Gly Gly
530                 535                 540

Thr Pro Asp Ile Pro Ser Ser Gly Leu Leu Ser Gly Gln Ala Gln Glu
545                 550                 555                 560

Asn Pro Gly Tyr Pro Tyr Ser Asp Ser Ser Ile Leu Gly Glu Asn
                565                 570                 575

Pro His Ile Gly Ile Asp Met Ile Asp Asn Asp Gln Gly Ser Ser Ser
            580                 585                 590

Pro Ser Asn Asp Glu Ala Ala Met Ala Val Ile Met Ser Leu Leu Glu
        595                 600                 605

Ala Asp Ala Gly Leu Gly Gly Pro Val Asp Phe Ser Asp Leu Pro Trp
    610                 615                 620

Pro Leu
625

<210> SEQ ID NO 7
<211> LENGTH: 491
<212> TYPE: PRT
<213> ORGANISM: Homo sapiens

<400> SEQUENCE: 7

Met Gly Val Asn Ala Val His Trp Phe Arg Lys Gly Leu Arg Leu His
1               5                   10                  15
```

```
Asp Asn Pro Ala Leu Lys Glu Cys Ile Gln Gly Ala Asp Thr Ile Arg
             20                  25                  30
Cys Val Tyr Ile Leu Asp Pro Trp Phe Ala Gly Ser Ser Asn Val Gly
             35                  40                  45
Ile Asn Arg Trp Arg Phe Leu Leu Gln Cys Leu Glu Asp Leu Asp Ala
 50                  55                  60
Asn Leu Arg Lys Leu Asn Ser Arg Leu Phe Val Ile Arg Gly Gln Pro
 65                  70                  75                  80
Ala Asp Val Phe Pro Arg Leu Phe Lys Glu Trp Asn Ile Thr Lys Leu
             85                  90                  95
Ser Ile Glu Tyr Asp Ser Glu Pro Phe Gly Lys Glu Arg Asp Ala Ala
            100                 105                 110
Ile Lys Lys Leu Ala Thr Glu Ala Gly Val Glu Val Ile Val Arg Ile
            115                 120                 125
Ser His Thr Leu Tyr Asp Leu Asp Lys Ile Ile Glu Leu Asn Gly Gly
            130                 135                 140
Gln Pro Pro Leu Thr Tyr Lys Arg Phe Gln Thr Leu Val Ser Lys Met
145                 150                 155                 160
Glu Pro Leu Glu Met Pro Ala Asp Thr Ile Thr Ser Asp Val Ile Gly
                165                 170                 175
Lys Cys Met Thr Pro Leu Ser Asp Asp His Asp Glu Lys Tyr Gly Val
                180                 185                 190
Pro Ser Leu Glu Glu Leu Gly Phe Asp Thr Asp Gly Leu Ser Ser Ala
            195                 200                 205
Val Trp Pro Gly Gly Glu Thr Glu Ala Leu Thr Arg Leu Glu Arg His
210                 215                 220
Leu Glu Arg Lys Ala Trp Val Ala Asn Phe Glu Arg Pro Arg Met Asn
225                 230                 235                 240
Ala Asn Ser Leu Leu Ala Ser Pro Thr Gly Leu Ser Pro Tyr Leu Arg
                245                 250                 255
Phe Gly Cys Leu Ser Cys Arg Leu Phe Tyr Phe Lys Leu Thr Asp Leu
                260                 265                 270
Tyr Lys Lys Val Lys Lys Asn Ser Ser Pro Pro Leu Ser Leu Tyr Gly
            275                 280                 285
Gln Leu Leu Trp Arg Glu Phe Phe Tyr Thr Ala Ala Thr Asn Asn Pro
290                 295                 300
Arg Phe Asp Lys Met Glu Gly Asn Pro Ile Cys Val Gln Ile Pro Trp
305                 310                 315                 320
Asp Lys Asn Pro Glu Ala Leu Ala Lys Trp Ala Glu Gly Arg Thr Gly
            325                 330                 335
Phe Pro Trp Ile Asp Ala Ile Met Thr Gln Leu Arg Gln Glu Gly Trp
            340                 345                 350
Ile His His Leu Ala Arg His Ala Val Ala Cys Phe Leu Thr Arg Gly
        355                 360                 365
Asp Leu Trp Ile Ser Trp Glu Glu Gly Met Lys Val Phe Glu Glu Leu
    370                 375                 380
Leu Leu Asp Ala Asp Trp Ser Ile Asn Ala Gly Ser Trp Met Trp Leu
385                 390                 395                 400
Ser Cys Ser Ser Phe Phe Gln Gln Phe Phe His Cys Tyr Cys Pro Val
                405                 410                 415
Gly Phe Gly Arg Arg Thr Asp Pro Asn Gly Asp Tyr Ile Arg Arg Tyr
            420                 425                 430
Leu Pro Val Leu Arg Gly Phe Pro Ala Lys Tyr Ile Tyr Asp Pro Trp
```

-continued

```
                435                 440                 445
Asn Ala Pro Glu Gly Ile Gln Lys Val Ala Lys Cys Leu Ile Gly Val
            450                 455                 460
Asn Tyr Pro Lys Pro Met Val Asn His Ala Glu Ala Ser Arg Leu Asn
465                 470                 475                 480
Ile Glu Arg Met Lys Gln Ile Tyr Gln Gln Leu
                485                 490

<210> SEQ ID NO 8
<211> LENGTH: 498
<212> TYPE: PRT
<213> ORGANISM: Artificial Sequence
<220> FEATURE:
<223> OTHER INFORMATION: synthetic polypeptide sequence

<400> SEQUENCE: 8

Gly Ala Met Asp Pro Glu Phe Met Gly Val Asn Ala Val His Trp Phe
1               5                   10                  15
Arg Lys Gly Leu Arg Leu His Asp Asn Pro Ala Leu Lys Glu Cys Ile
            20                  25                  30
Gln Gly Ala Asp Thr Ile Arg Cys Val Tyr Ile Leu Asp Pro Trp Phe
        35                  40                  45
Ala Gly Ser Ser Asn Val Gly Ile Asn Arg Trp Arg Phe Leu Leu Gln
    50                  55                  60
Cys Leu Glu Asp Leu Asp Ala Asn Leu Arg Lys Leu Asn Ser Arg Leu
65                  70                  75                  80
Phe Val Ile Arg Gly Gln Pro Ala Asp Val Phe Pro Arg Leu Phe Lys
                85                  90                  95
Glu Trp Asn Ile Thr Lys Leu Ser Ile Glu Tyr Asp Ser Glu Pro Phe
            100                 105                 110
Gly Lys Glu Arg Asp Ala Ala Ile Lys Lys Leu Ala Thr Glu Ala Gly
        115                 120                 125
Val Glu Val Ile Val Arg Ile Ser His Thr Leu Tyr Asp Leu Asp Lys
    130                 135                 140
Ile Ile Glu Leu Asn Gly Gly Gln Pro Pro Leu Thr Tyr Lys Arg Phe
145                 150                 155                 160
Gln Thr Leu Val Ser Lys Met Glu Pro Leu Glu Met Pro Ala Asp Thr
                165                 170                 175
Ile Thr Ser Asp Val Ile Gly Lys Cys Met Thr Pro Leu Ser Asp Asp
            180                 185                 190
His Asp Glu Lys Tyr Gly Val Pro Ser Leu Glu Glu Leu Gly Phe Asp
        195                 200                 205
Thr Asp Gly Leu Ser Ser Ala Val Trp Pro Gly Gly Glu Thr Glu Ala
    210                 215                 220
Leu Thr Arg Leu Glu Arg His Leu Glu Arg Lys Ala Trp Val Ala Asn
225                 230                 235                 240
Phe Glu Arg Pro Arg Met Asn Ala Asn Ser Leu Leu Ala Ser Pro Thr
                245                 250                 255
Gly Leu Ser Pro Tyr Leu Arg Phe Gly Cys Leu Ser Cys Arg Leu Phe
            260                 265                 270
Tyr Phe Lys Leu Thr Asp Leu Tyr Lys Lys Val Lys Lys Asn Ser Ser
        275                 280                 285
Pro Pro Leu Ser Leu Tyr Gly Gln Leu Leu Trp Arg Glu Phe Phe Tyr
    290                 295                 300
Thr Ala Ala Thr Asn Asn Pro Arg Phe Asp Lys Met Glu Gly Asn Pro
```

```
            305                 310                 315                 320
    Ile Cys Val Gln Ile Pro Trp Asp Lys Asn Pro Glu Ala Leu Ala Lys
                        325                 330                 335

Trp Ala Glu Gly Arg Thr Gly Phe Pro Trp Ile Asp Ala Ile Met Thr
                    340                 345                 350

Gln Leu Arg Gln Glu Gly Trp Ile His His Leu Ala Arg His Ala Val
                355                 360                 365

Ala Cys Phe Leu Thr Arg Gly Asp Leu Trp Ile Ser Trp Glu Glu Gly
            370                 375                 380

Met Lys Val Phe Glu Glu Leu Leu Asp Ala Asp Trp Ser Ile Asn
    385                 390                 395                 400

Ala Gly Ser Trp Met Trp Leu Ser Cys Ser Ser Phe Phe Gln Gln Phe
                    405                 410                 415

Phe His Cys Tyr Cys Pro Val Gly Phe Gly Arg Arg Thr Asp Pro Asn
                420                 425                 430

Gly Asp Tyr Ile Arg Arg Tyr Leu Pro Val Leu Arg Gly Phe Pro Ala
            435                 440                 445

Lys Tyr Ile Tyr Asp Pro Trp Asn Ala Pro Glu Gly Ile Gln Lys Val
        450                 455                 460

Ala Lys Cys Leu Ile Gly Val Asn Tyr Pro Lys Pro Met Val Asn His
    465                 470                 475                 480

Ala Glu Ala Ser Arg Leu Asn Ile Glu Arg Met Lys Gln Ile Tyr Gln
                    485                 490                 495

Gln Leu

<210> SEQ ID NO 9
<211> LENGTH: 540
<212> TYPE: PRT
<213> ORGANISM: Artificial sequence
<220> FEATURE:
<223> OTHER INFORMATION: synthetic polypeptide sequence

<400> SEQUENCE: 9

Met Gly Ser Ser His His His His His His Gly Ser Ser Gly Ser Ser
    1               5                   10                  15

Gly His His His Gly Ser Ser Gly Ser Ser Gly Ser Ser Met Asn Lys
                    20                  25                  30

Glu Ile Leu Ala Val Val Glu Ala Val Ser Asn Glu Lys Ala Leu Pro
                35                  40                  45

Arg Glu Lys Ile Phe Glu Ala Leu Glu Ser Ala Leu Ala Thr Ala Thr
        50                  55                  60

Lys Lys Lys Tyr Glu Gln Glu Ile Asp Val Arg Val Gln Ile Asp Arg
    65                  70                  75                  80

Lys Ser Gly Asp Phe Asp Thr Phe Arg Arg Trp Leu Val Val Asp Glu
                    85                  90                  95

Val Thr Gln Pro Thr Lys Glu Ile Thr Leu Glu Ala Ala Arg Tyr Glu
                100                 105                 110

Asp Glu Ser Leu Asn Leu Gly Asp Tyr Val Glu Asp Gln Ile Glu Ser
                115                 120                 125

Val Thr Phe Asp Arg Ile Thr Thr Gln Thr Ala Lys Gln Val Ile Val
                130                 135                 140

Gln Lys Val Arg Glu Ala Glu Arg Ala Met Val Val Asp Gln Phe Arg
    145                 150                 155                 160

Glu His Glu Gly Glu Ile Ile Thr Gly Val Val Lys Lys Val Asn Arg
                    165                 170                 175
```

```
Asp Asn Ile Ser Leu Asp Leu Gly Asn Asn Ala Glu Ala Val Ile Leu
                180                 185                 190

Arg Glu Asp Met Leu Pro Arg Glu Asn Phe Arg Pro Gly Asp Arg Val
            195                 200                 205

Arg Gly Val Leu Tyr Ser Val Arg Pro Glu Ala Arg Gly Ala Gln Leu
        210                 215                 220

Phe Val Thr Arg Ser Lys Pro Glu Met Leu Ile Glu Leu Phe Arg Ile
225                 230                 235                 240

Glu Val Pro Glu Ile Gly Glu Val Ile Glu Ile Lys Ala Ala
                245                 250                 255

Arg Asp Pro Gly Ser Arg Ala Lys Ile Ala Val Lys Thr Asn Asp Lys
                260                 265                 270

Arg Ile Asp Pro Val Gly Ala Cys Val Gly Met Arg Gly Ala Arg Val
            275                 280                 285

Gln Ala Val Ser Thr Glu Leu Gly Gly Glu Arg Ile Asp Ile Val Leu
        290                 295                 300

Trp Asp Asp Asn Pro Ala Gln Phe Val Ile Asn Ala Met Ala Pro Ala
305                 310                 315                 320

Asp Val Ala Ser Ile Val Val Asp Glu Asp Lys His Thr Met Asp Ile
                325                 330                 335

Ala Val Glu Ala Gly Asn Leu Ala Gln Ala Ile Gly Arg Asn Gly Gln
            340                 345                 350

Asn Val Arg Leu Ala Ser Gln Leu Ser Gly Trp Glu Leu Asn Val Met
        355                 360                 365

Thr Val Asp Asp Leu Gln Ala Lys His Gln Ala Glu Ala His Ala Ala
370                 375                 380

Ile Asp Thr Phe Thr Lys Tyr Leu Asp Ile Asp Glu Asp Phe Ala Thr
385                 390                 395                 400

Val Leu Val Glu Glu Gly Phe Ser Thr Leu Glu Glu Leu Ala Tyr Val
                405                 410                 415

Pro Met Lys Glu Leu Leu Glu Ile Glu Gly Leu Asp Glu Pro Thr Val
            420                 425                 430

Glu Ala Leu Arg Glu Arg Ala Lys Asn Ala Leu Ala Thr Ile Ala Gln
        435                 440                 445

Ala Gln Glu Glu Ser Leu Gly Asp Asn Lys Pro Ala Asp Asp Leu Leu
450                 455                 460

Asn Leu Glu Gly Val Asp Arg Asp Leu Ala Phe Lys Leu Ala Ala Arg
465                 470                 475                 480

Gly Val Cys Thr Leu Glu Asp Leu Ala Glu Gln Gly Ile Asp Asp Leu
                485                 490                 495

Ala Asp Ile Glu Gly Leu Thr Asp Glu Lys Ala Gly Ala Leu Ile Met
            500                 505                 510

Ala Ala Arg Asn Ile Cys Trp Phe Gly Asp Glu Ala Gly Ile Glu Glu
        515                 520                 525

Asn Leu Tyr Phe Gln Gly Ala Met Asp Pro Glu Phe
530                 535                 540

<210> SEQ ID NO 10
<211> LENGTH: 135
<212> TYPE: PRT
<213> ORGANISM: Homo sapiens

<400> SEQUENCE: 10

Gln Phe Ile Lys Glu Met Cys Thr Val Glu Glu Pro Asn Glu Glu Phe
```

```
                1               5                   10                  15
            Thr Ser Arg His Ser Leu Glu Trp Lys Phe Leu Phe Leu Asp His Arg
                            20                  25                  30

Ala Pro Pro Ile Ile Gly Tyr Leu Pro Phe Glu Val Leu Gly Thr Ser
                        35                  40                  45

Gly Tyr Asp Tyr Tyr His Val Asp Asp Leu Glu Asn Leu Ala Lys Cys
                    50                  55                  60

His Glu His Leu Met Gln Tyr Gly Lys Gly Lys Ser Cys Tyr Tyr Arg
            65                  70                  75                  80

Phe Leu Thr Lys Gly Gln Gln Trp Ile Trp Leu Gln Thr His Tyr Tyr
                            85                  90                  95

Ile Thr Tyr His Gln Trp Asn Ser Arg Pro Glu Phe Ile Val Cys Thr
                        100                 105                 110

His Thr Val Val Ser Tyr Ala Glu Val Arg Ala Glu Arg Arg Arg Glu
                    115                 120                 125

Leu Gly Ile Glu Glu Ser Leu
                    130                 135

<210> SEQ ID NO 11
<211> LENGTH: 142
<212> TYPE: PRT
<213> ORGANISM: Artificial sequence
<220> FEATURE:
<223> OTHER INFORMATION: synthetic polypeptide sequence

<400> SEQUENCE: 11

Gly Ala Met Asp Pro Glu Phe Gln Phe Ile Lys Glu Met Cys Thr Val
            1               5                   10                  15

Glu Glu Pro Asn Glu Glu Phe Thr Ser Arg His Ser Leu Glu Trp Lys
                            20                  25                  30

Phe Leu Phe Leu Asp His Arg Ala Pro Pro Ile Ile Gly Tyr Leu Pro
                        35                  40                  45

Phe Glu Val Leu Gly Thr Ser Gly Tyr Asp Tyr Tyr His Val Asp Asp
                    50                  55                  60

Leu Glu Asn Leu Ala Lys Cys His Glu His Leu Met Gln Tyr Gly Lys
            65                  70                  75                  80

Gly Lys Ser Cys Tyr Tyr Arg Phe Leu Thr Lys Gly Gln Gln Trp Ile
                            85                  90                  95

Trp Leu Gln Thr His Tyr Tyr Ile Thr Tyr His Gln Trp Asn Ser Arg
                        100                 105                 110

Pro Glu Phe Ile Val Cys Thr His Thr Val Val Ser Tyr Ala Glu Val
                    115                 120                 125

Arg Ala Glu Arg Arg Arg Glu Leu Gly Ile Glu Glu Ser Leu
                130                 135                 140

<210> SEQ ID NO 12
<211> LENGTH: 22
<212> TYPE: PRT
<213> ORGANISM: Homo sapiens

<400> SEQUENCE: 12

Cys Ser Gln Gly Ser Gly Ile Leu His Tyr Ala His Gly Asp Ser Gln
            1               5                   10                  15

Gln Thr His Leu Leu Lys
                            20

<210> SEQ ID NO 13
```

```
<211> LENGTH: 6
<212> TYPE: PRT
<213> ORGANISM: Artificial sequence
<220> FEATURE:
<223> OTHER INFORMATION: synthetic polypeptide sequence

<400> SEQUENCE: 13

His Gln Trp Asn Ser Arg
1               5

<210> SEQ ID NO 14
<211> LENGTH: 6
<212> TYPE: PRT
<213> ORGANISM: Artificial sequence
<220> FEATURE:
<223> OTHER INFORMATION: synthetic polypeptide sequence

<400> SEQUENCE: 14

Asn Pro Trp Thr Lys Glu
1               5
```

CRY1-CLOCK-BMAL1 COMPLEX-DISRUPTING AGENTS AND METHODS OF IDENTIFYING AND USING SAME

CROSS-REFERENCE TO RELATED APPLICATIONS

This application claims the benefit of U.S. Provisional Patent Application No. 62/444,691, filed Jan. 10, 2017, which application is incorporated herein by reference in its entirety.

STATEMENT OF GOVERNMENTAL SUPPORT

This invention was made with Government support under contract numbers CA189660 and GM107069, awarded by the National Institutes of Health. The Government has certain rights in the invention.

INTRODUCTION

Circadian rhythms allow animals to coordinate behavior and physiology with the environmental light/dark cycle. While a host of cellular processes contribute to the generation of ~24-hour timing at the molecular level (e.g., transcriptional, post-transcriptional, translational, post-translational), the mammalian transcription factor CLOCK:BMAL1 sits at the core of integrated transcription-translation feedback loops that regulate the rhythmic expression of over 40% of the genome throughout the body. In support of its central role, the loss of Bmal1 renders mice arrhythmic in the absence of external time cues, the only single clock gene deletion to do so in mice. Disruption of circadian rhythms has been linked to altered cellular homeostasis and disease.

Recent studies have suggested the presence of several regulatory complexes of core clock proteins that form throughout the day to establish a dynamic balance of CLOCK:BMAL1 activation and repression. In the morning, CLOCK:BMAL1 is bound at E-box sites on DNA with its coactivator CBP/p300, driving expression of the core clock repressors Per and Cry along with other clock-controlled output genes. Repression begins early in the evening, defined by large hetero-multimeric PER:CRY complexes bound to CLOCK:BMAL1. The structural basis for formation of these complexes, and whether they occur primarily on or off DNA, is still not well understood. Based on ChIP-Seq studies, these complexes appear to remodel or reform over time, evolving to a late repressive complex where CRY1 is bound to CLOCK:BMAL1 on DNA, apparently independently of PER. These findings indicate that cryptochromes can work both together and separately from PER to repress CLOCK:BMAL1 activity. Tuning affinity of CRY1 for the transactivation domain (TAD) of BMAL1 controls circadian period by competing with the coactivator CBP/p300. CRY1 also binds to CLOCK, although it is not yet understood how multivalent interactions with CLOCK:BMAL1 contribute to CRY1 function. Therefore, understanding the molecular basis for recruitment of regulators to CLOCK:BMAL1 will shed light on mechanisms that are crucial for establishing the ~24-hour periodicity of the circadian clock.

SUMMARY

Provided are agents that disrupt CRY1-CLOCK-BMAL1 ternary complexes. In certain aspects, the agents bind to the secondary pocket of CRY1 and inhibit interaction between the secondary pocket and the PAS-B domain of CLOCK, to disrupt CRY1-CLOCK-BMAL1 ternary complexes. Also provided are methods for identifying such agents, compositions including such agents, and therapeutic methods employing such agents.

DETAILED DESCRIPTION

Figure 1:
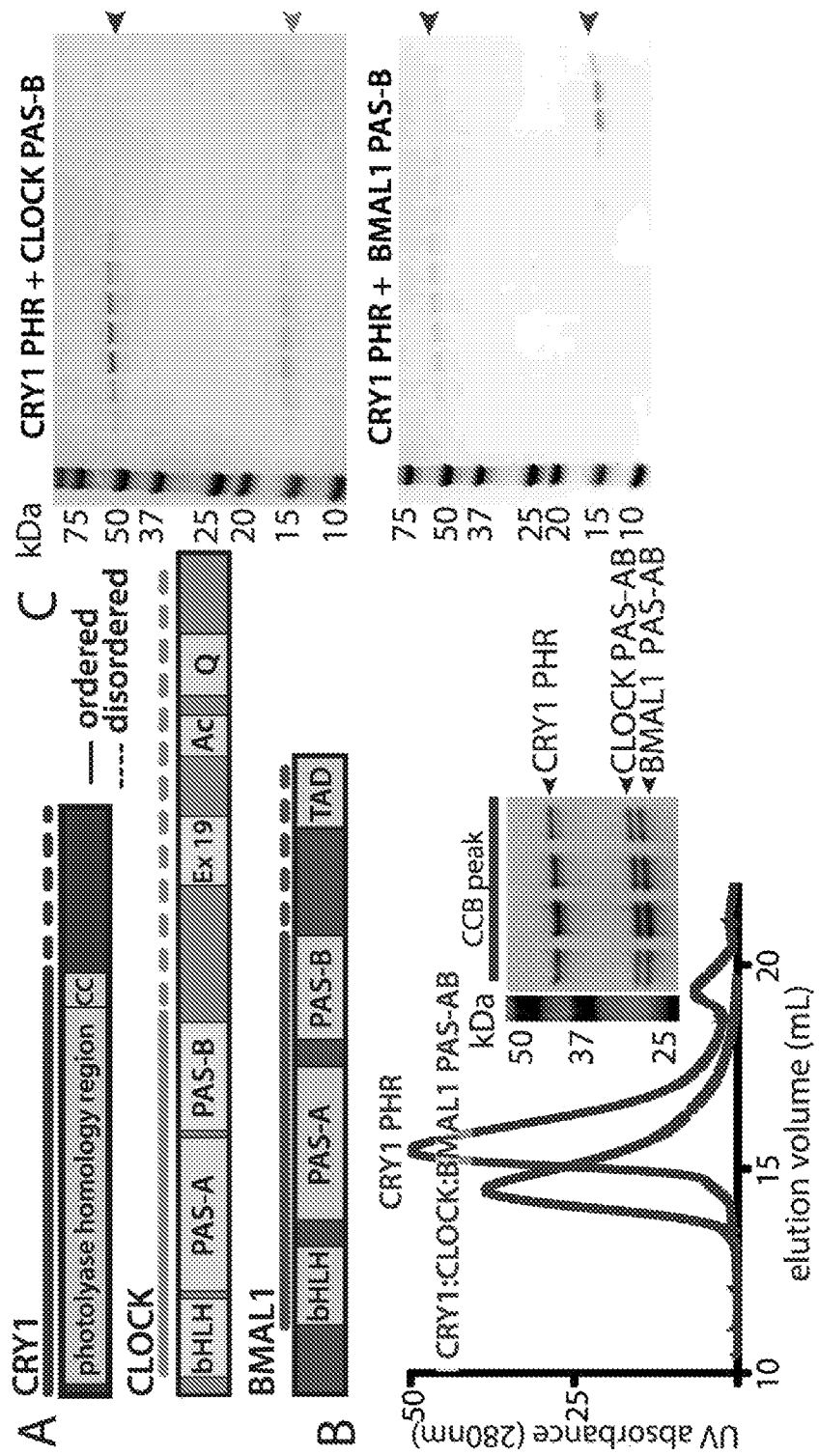
FIG. 1 provides data demonstrating that CRY interacts directly with the CLOCK:BMAL1 PAS domain core. Panel A: Domain schematic of CRY1, CLOCK and BMAL1. Solid lines indicate regions used in the studies described in the Experimental section below. Panel B: Size exclusion chromatography (SEC) analysis of complex formation with CRY1 PHR alone or mixed with the CLOCK:BMAL1 tandem PAS-AB domain dimer. Proteins were mixed and incubated at 4° C. overnight and then injected on a S200 10/300 GL column. The peak fraction of CRY1 PHR with CLOCK:BMAL1 PAS-AB was analyzed by SDS-PAGE (CCB peak) and stained by Coomassie. Panel C: SEC analysis of CRY1 PHR with CLOCK PAS-B (top) or BMAL1 PAS-B (bottom) in isolation. Identical fractions (12-18.5 mL on a S200 10/300GL column, 0.5 mL each) were analyzed by SDS-PAGE gel electrophoresis and stained by Coomassie. Arrows indicate CRY1 PHR, CLOCK PAS-B and BMAL1 PAS-B.

Provided are agents that disrupt CRY1-CLOCK-BMAL1 ternary complexes. In certain aspects, the agents bind to the secondary pocket of CRY1 and inhibit interaction between the secondary pocket and the PAS-B domain of CLOCK, to disrupt CRY1-CLOCK-BMAL1 ternary complexes. Also provided are methods for identifying such agents, corn positions including such agents, and therapeutic methods employing such agents.

Before the agents and methods of the present disclosure are described in greater detail, it is to be understood that the agents and methods are not limited to particular embodiments described, as such may, of course, vary. It is also to be understood that the terminology used herein is for the purpose of describing particular embodiments only, and is not intended to be limiting, since the scope of the agents and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the agents and methods. The upper and lower limits of these smaller ranges may independently be included in the smaller ranges and are also encompassed within the agents and methods, subject to any specifically excluded limit in the stated range. Where the stated range includes one or both of the limits, ranges excluding either or both of those included limits are also included in the agents and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the agents and methods belong. Although any agents and methods similar or equivalent to those described herein can also be used in the practice or testing of the agents and methods, representative illustrative agents and methods are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present agents and methods are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the agents and methods, which are, for clarity, described in the context of separate embodiments, may also be provided in combination in a single embodiment. Conversely, various features of the agents and methods, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present agents and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

CRY1:CLOCK:BMAL1 Complex-Disrupting Agents

Circadian rhythms are established by genetically encoded clocks that function at the cellular level to measure time in ~24-hour increments to align host physiology and behavior with the 24-hour light/dark cycle. The molecular clock that underlies circadian rhythms is based on a set of interlocked transcription/translation feedback loops including a set of dedicated core clock proteins. At the heart of the feedback loops, the primary circadian transcription factor CLOCK:BMAL1 binds to E-box consensus motifs in clock target genes to activate transcription; two of the targeted genes encode its dedicated repressors, cryptochrome (CRY) and period (PER). CRY and PER proteins associate in the cytoplasm, undergo extensive post-translational modification, and re-enter the nucleus to inhibit CLOCK:BMAL1 activity. The onset and duration of the circadian repressive phase is critical for establishing the intrinsic ~24-hour period of the clock.

The inventors identify herein a deep, druggable pocket on the core clock protein CRY1 that is used to bind the primary circadian transcription factor CLOCK:BMAL1. The molecular factors governing complex formation are described in detail herein, including in the Experimental section below. In addition to the agents provided herein, the present disclosure allows for the design and discovery of agents (e.g., small molecules, peptides, and/or the like) that rapidly reset the circadian clock, allowing easier adjustment to changes in the light environment encountered in, e.g., shift work, long-distance travel, etc.

Previous attempts to regulate the circadian clock with drug-like molecules has not yielded viable candidate drugs, likely due to the fact that the protein targets of these drugs (kinases that phosphorylate PER-CRY complexes) function in many other signaling pathways and likely lead to off-target effects. Moreover, the goal of any drug to manipulate circadian rhythms is to rapidly and precisely take the transcription/translation feedback loop of the clock to a single point within its 24-hour cycle (to shift the phase of the oscillator). Agents of the present disclosure meet this criteria.

As summarized above, aspects of the present disclosure include CRY1:CLOCK:BMAL1 complex-disrupting agents. As used herein, a "CRY1:CLOCK:BMAL1 complex-disrupting agent" is an agent that binds to the CRY1 PHR (e.g., at the CRY1 secondary pocket) and inhibits/disrupts interaction between the secondary pocket and the CLOCK PAS-B domain, thereby disrupting an existing CRY1:CLOCK:BMAL1 complex (where "BMAL1" as used herein may refer to ARNTL (Aryl Hydrocarbon Receptor Nuclear Translocator Like)) or preventing the formation of such a complex. As demonstrated in the Experimental section below, the inventors have surprisingly discovered that inhibition/disruption of the interaction between the secondary pocket and the CLOCK PAS-B domain (which interaction is described for the first time herein) is sufficient to prevent formation of the CRY1:CLOCK:BMAL1 ternary complex. This interaction may be targeted using an agent of the present disclosure for research and/or therapeutic purposes. In the therapeutic context, the agents may be administered as therapy to, e.g., reset the circadian clock in an individual having a circadian rhythm-related disorder such as shift-work sleep disorder, jet lag, metabolic imbalance, etc.

The amino acid sequences of wild-type mouse and human CRY1, CLOCK and BMAL1 are provided in Table 1 below. The mouse and human CLOCK PAS-B domain amino acid sequences are identical and underlined in Table 1.

TABLE 1

CRY1, CLOCK and BMAL1 Amino Acid Sequences

| | Amino Acid Sequence |
|---|---|
| Wild-Type Mouse CRY1 (UniProt No. P97784) (SEQ ID NO: 1) | MGVNAVHWFRKGLRLHDNPALKECIQGADTIRCVYILDPWFAGSSNVGI NRWRFLLQCLEDLDANLRKLNSRLFVIRGQPADVFPRLFKEWNITKLSIE YDSEPFGKERDAAIKKLATEAGVEVIVRISHTLYDLDKIIELNGGQPPLTY KRFQTLVSKMEPLEMPADTITSDVIGKCMTPLSDDHDEKYGVPSLEELG FDTDGLSSAVWPGGETEALTRLERHLERKAWVANFERPRMNANSLLA SPTGLSPYLRFGCLSCRLFYFKLTDLYKKVKKNSSPPLSLYGQLLWREF FYTAATNNPRFDKMEGNPICVQIPWDKNPEALAKWAEGRTGFPWIDAI MTQLRQEGWIHHLARHAVACFLTRGDLWISWEEGMKVFEELLLDADW SINAGSWMWLSCSSFFQQFFHCYCPVGFGRRTDPNGDYIRRYLPVLR GFPAKYIYDPWNAPEGIQKVAKCLIGVNYPKPMVNHAEASRLNIERMKQ IYQQLSRYRGLGLLASVPSNSNGNGGLMGYAPGENVPSCSSSGNGGL MGYAPGENVPSCSGGNCSQGSGILHYAHGDSQQTHSLKQGRSSAGT GLSSGKRPSQEEDAQSVGPKVORQSSN |
| Wild-Type Mouse CLOCK (UniProt No. O08785) (SEQ ID NO: 2) | MVFTVSCSKMSSIVDRDDSSIFDGLVEEDDKDKAKRVSRNKSEKKRRD QFNVLIKELGSMLPGNARKMDKSTVLQKSIDFLRKHKETTAQSDASEIR QDWKPTFLSNEEFTQLMLEALDGFFLAIMTDGSIIYVSESVTSLLEHLPS DLVDQSIFNFIPEGEHSEVYKILSTHLLESDSLTPEYLKSKNOLEFCCHM LRGTIDPKEPSTYEYVRFIGNFKSLTSVSTSTHNGFEGTIQRTHRPSYED RVCFVATVRLATPQFIKEMCTVEEPNEEFTSRHSLEWKFLFLDHRAPPII GYLPFEVLGTSGYDYYHVDDLENLAKCHEHLMQYGKGKSCYYRFLTKG QQWIWLQTHYYITYHQWNSRPEFIVCTHTVVSYAEVRAERRRELGIEES LPETAADKSQDSGSDNRINTVSLKEALERFDHSPTPSASSRSSRKSSHT AVSDPSSTPTKIPTDTSTPPROHLPAHEKMTQRRSSFSSQSINSQSVGP SLTQPAMSQAANLPIPQGMSQFQFSAQLGAMQHLKDQLEQRTRMIEA NIHRQQEELRKIQEQLQMVHGQGLQMFLQQSNPGLNFGSVQLSSGNS NIQQLTPVNMQGQVVPANQVQSGHISTGQHMIQQQTLOSTSTQQSQQ SVMSGHSQQTSLPSQTPSTLTAPLYNTMVISQPAAGSMVQ1PSSMPQN STQSATVITFTQDRQIRFSQGQQLVTKLVTAPVACGAVMVPSTMLMGQ VVTAYPTFATQQOOAQTLSVTQQQQQQQQPPQQQQQOOQSSQEQ QLPSVQQPAQAQLGQPPQQFLQTSRLLHGNPSTQLILSAAFPLQQSTF PPSHHQQHQPQQQQQLPRHRTDSLTDPSKVQPQ |
| Wild-Type Mouse BMAL1 (UniProt No. Q9WTL8) (SEQ ID NO: 3) | MADQRMDISSTISDFMSPGPTDLLSGSLGTSGVDCNRKRKGSATDYQL DDFAFEESMDTDKDDPHGRLEYAEHQGRIKNAREAHSQIEKRRRDKM NSFIDELASLVPTCNAMSRKLDKLTVLRMAVQHMKTLRGATNPYTEANY KPTFLSDDELKHLILRAADGFLFVVGCDRGKILFVSESVFKILNYSQNDLI GOSLFDYLHPKDIAKVKEQLSSSDTAPRERLIDAKTGLPVKTDITPGPSR LCSGARRSFFCRMKCNRPSVKVEDKDFASTCSKKKDRKSFCTIHSTGY LKSWPPTKMGLDEDNEPDNEGCNLSCLVAIGRLHSHMVPQPANGEIRV KSMEYVSRHAIDGKFVFVDQRATAILAYLPQELLGTSCYEYFHQDDIGH LAECHRQVLQTREKITTNCYKFKIKDGSFITLRSRWFSFMNPWTKEVEYI VSTNTVVLANVLEGGDPTFPQLTAPPHSMDSMLPSGEGGPKRTHPTVP GIPGGTRAGAGKIGRMIAEEIMEIHRIRGSSPSSCGSSPLNITSTPPPDA SSPGGKKILNGGTPDIPSTGLLPGQAQETPGYPYSDSSSILGENPHIGID MIDNDQGSSSPSNDEAAMAVIMSLLEADAGLGGPVDFSDLPWPL |
| Wild-Type Human CRY1 (UniProt No. Q16526) (SEQ ID NO: 4) | MGVNAVHWFRKGLRLHDNPALKECIQGADTIRCVYILDPWFAGSSNVGI NRWRFLLQCLEDLDANLRKLNSRLFVIRGQPADVFPRLFKEWNITKLSIE YDSEPFGKERDAAIKKLATEAGVEVIVRISHTLYDLDKIIELNGGQPPLTY KRFQTLISKMEPLEIPVETITSEVIEKCTTPLSDDHDEKYGVPSLEELGFD TDGLSSAVWPGGETEALTRLERHLERKAWVANFERPRMNANSLLASP TGLSPYLRFGCLSCRLFYFKLTDLYKKVKKNSSPPLSLYGQLLWREFFY |

TABLE 1 -continued

CRY1, CLOCK and BMAL1 Amino Acid Sequences

| | Amino Acid Sequence |
|---|---|
| | TAATNNPRFDKMEGNPICVQIPWDKNPEALAKWAEGRTGFPWIDAIMT<br>QLRQEGWIHHLARHAVACFLTRGDLWISWEEGMKVFEELLLDADWSIN<br>AGSWMWLSCSSFFQQFFHCYCPVGFGRRTDPNGDYIRRYLPVLRGFP<br>AKYIYDPWNAPEGIQKVAKCLIGVNYPKPMVNHAEASRLNIERMKQIYQ<br>QLSRYRGLGLLASVPSNPNGNGGFMGYSAENIPGCSSSGSCSQGSGIL<br>HYAHGDSQQTHLLKQGRSSMGTLSGGKRPSQEEDTQSIGPKVQRQS<br>TN |
| Wild-Type<br>Human CLOCK<br>(UniProt No.<br>O15516)<br>(SEQ ID NO: 5) | MLFTVSCSKMSSIVDRDDSSIFDGLVEEDDKDKAKRVSRNKSEKKRRD<br>QFNVLIKELGSMLPGNARKMDKSTVLQKSIDFLRKHKEITAQSDASEIRQ<br>DWKPTFLSNEEFTQLMLEALDGFFLAIMTDGSIIYVSESVTSLLEHLPSD<br>LVDQSIFNFIPEGEHSEVYKILSTHLLESDSLTPEYLKSKNQLEFCCHML<br>RGTIDPKEPSTYEYVKFIGNFKSLNSVSSSAHNGFEGTIQRTHRPSYED<br>RVCFVATVRLATPQFIKEMCTVEEPNEEFTSRHSLEWKFLFLDHRAPPII<br>GYLPFEVLGTSGYDYYHVDDLENLAKCHEHLMQYGKGKSCYYRFLTKG<br>QQW1WLQTHYYITYHOWNSRPEFIVOTHTVVSYAEVRAERRRELGIEES<br>LPETAADKSQDSGSDNRINTVSLKEALERFDHSPTPSASSRSSRKSSHT<br>AVSDPSSTPTKIPTDTSTPPRQHLPAHEKMVQRRSSFSSQSINSQSVGS<br>SLTQPVMSQATNLPIPQGMSQFQFSAQLGAMQHLKDQLEQRTRMIEAN<br>IHRQQEELRKIQEQLQMVHGQGLQMFLQQSNPGLNFGSVQLSSGNSS<br>NIQQLAPINMQGQVVPTNQIQSGMNTGHIGTTQHMIQQQTLQSTSTQS<br>QQNVLSGHSQQTSLPSQTQSTLTAPLYNTMVISQPAAGSMVQIPSSMP<br>QNSTQSAAVTTFTQDRQIRFSQGQQLVTKLVTAPVACGAVMVPSTMLM<br>GQVVTAYPTFATQQQQSQTLSVTQQQQQQSSQEQQLTSVQQPSQAQ<br>LTQPPQQFLQTSRLLHGNPSTQLILSAAFPLQQSTFPQSHHQQHQSQQ<br>QQQLSRHRTDSLPDPSKVQPQ |
| Wild-Type<br>Human BMAL1<br>(UniProt No.<br>O00327)<br>(SEQ ID NO: 6) | MADQRMDISSTISDFMSPGPTDLLSSSLGTSGVDCNRKRKGSSTDYQE<br>SMDTDKDDPHGRLEYTEHQGRIKNAREAHSQIEKRRRDKMNSFIDELA<br>SLVPTCNAMSRKLDKLTVLRMAVQHMKTLRGATNPYTEANYKPTFLSD<br>DELKHLILRAADGFLFVVGCDRGKILFVSESVFKILNYSQNDLIGQSLFDY<br>LHPKDIAKVKEQLSSSDTAPRERLIDAKTGLPVKTDITPGPSRLCSGARR<br>SFFCRMKCNRPSVKVEDKDFPSTCSKKKADRKSFCTIHSTGYLKSWPP<br>TKMGLDEDNEPDNEGCNLSCLVAIGRLHSHVVPQPVNGEIRVKSMEYV<br>SRHAIDGKFVFVDQRATAILAYLPQELLGTSCYEYFHQDDIGHLAECHR<br>QVLQTREKITTNCYKFKIKDGSFITLRSRWFSFMNPWTKEVEYIVSTNTV<br>VLANVLEGGDPTFPQLTASPHSMDSMLPSGEGGPKRTHPTVPGIPGGT<br>RAGAGKIGRMIAEEIMEIHRIRGSSPSSCGSSPLNITSTPPPDASSPGGK<br>KILNGGTPDIPSSGLLSGQAQENPGYPYSDSSSILGENPHIGIDMIDNDQ<br>GSSSPSNDEAAMAVIMSLLEADAGLGGPVDFSDLPWPL |

According to certain embodiments, a CRY1:CLOCK:BMAL1 complex-disrupting agent of the present disclosure binds to the secondary pocket of CRY1 and inhibits interaction between the secondary pocket and the CLOCK PAS-B domain. Agents of interest include, but are not limited to, small molecules, polymers (e.g., peptides, polypeptides, etc.), or the like. As used herein, a "peptide" is a polymer including from 2 to 50 amino acids, and a "polypeptide" is a polymer including more than 50 amino acids.

The N-terminal subdomain of the photolyase/cryptochrome family has a ligand-binding pocket known as the antenna chromophore (or "secondary") binding pocket. The nucleotide-like chromophores that have been identified to bind this cavity act as efficient light harvesters for photolyases and cryptochromes that possess photosensory functions (as DNA repair enzymes or blue light signaling molecules). Both flavin mononucleotide (FMN) and flavin adenine dinucleotide (FAD), the two biologically active forms of riboflavin (vitamin $B_2$), have been shown to bind members of the family. In addition, 8-hydroxydeazaflavin (8-HDF) has also been shown to bind in organisms that have the capability to synthesize this modified flavin. In addition to these molecules of the flavin family, some photolyases bind the folate derivative MTHF (methylenetetrahydrofolate). As demonstrated in the Experimental section below, the inventors have determined that a tryptophan side chain from CLOCK PAS-B is essential for CRY1 binding, which possesses chemical similarity to these known photolyase- and cryptochrome-binding molecules. As such, in certain aspects, a CRY1:CLOCK:BMAL1 complex-disrupting agent of the present disclosure includes a flavin moiety. According to certain embodiments, an agent of the present disclosure is a folate derivative.

In certain aspects, the agent is a peptide or polypeptide that includes, or consists of, a CLOCK PAS-B domain or a variant thereof. For example, the agent may be a peptide or polypeptide that includes, or consists of, a CLOCK PAS-B domain, where the peptide or polypeptide does not bind to BMAL1 and competes with a CLOCK PAS-B domain present in a CLOCK:BMAL1 complex for binding to the photolyase homology region (PHR) (e.g., the secondary pocket) of CRY1. By "variant" is meant a CLOCK PAS-B domain that differs (e.g., in amino acid sequence) from a wild-type CLOCK PAS-B domain, but retains the ability to bind the secondary pocket of CRY1 in the same or substantially the same manner as a wild-type CLOCK PAS-B domain. Details regarding the manner in which a wild-type CLOCK PAS-B domain interacts with the secondary pocket of CRY1, and example approaches for determining the manner in which a PAS-B domain interacts with the secondary pocket of CRY1, are provided in the Experimental section below.

Also provided are nucleic acids that encode any of the peptide or polypeptide agents of the present disclosure. In certain aspects, such a nucleic acid is present in an expression vector. The expression vector includes a promoter operably linked to the nucleic acid encoding the peptide or polypeptide agent, the promoter being selected based on the type of host cell selected to express the peptide or polypeptide agent, which in certain aspects is a target host cell in an individual (e.g., an individual having a circadian rhythm disorder). Also provided are liposomes that include any of the nucleic acids or expression vectors of the present disclosure. In certain aspects, such liposomes include targeting moieties (e.g., antibodies) on the surface thereof to target the liposomes (and in turn, the nucleic acids or expression vectors) to a target tissue of interest.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance, neomycin resistance, and/or the like) to permit detection of those cells transformed with the desired DNA sequences.

Also provided are host cells that include a nucleic acid that encodes any of the peptide or polypeptide agents described herein, as well as any expression vectors including the same. *Escherichia coli* is an example of a prokaryotic host cell that can be used for cloning a nucleic acid encoding a peptide or polypeptide agent of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In some embodiments, insect cells are used to express and produce a peptide or polypeptide agent of the present disclosure. For example, the CRY1 protein that includes the CRY1 PHR and/or the CLOCK PAS-B domain may be produced in suitable insect cell, a non-limiting example of which is an Sf9 cell.

In addition to microorganisms and insect cells, mammalian cells (e.g., mammalian cells grown in in vitro cell culture) can be used to express and produce the peptide or polypeptide agents of the present disclosure. Suitable mammalian host cells include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like.

In some embodiments, a CRY1:CLOCK:BMAL1 complex-disrupting agent of the present disclosure is an agent identified using the methods of the present disclosure for identifying agents that disrupt a ternary complex including CRY1, CLOCK, and BMAL1. Such methods are described in detail below.

Methods for Identifying Agents that Disrupt CRY1:CLOCK:BMAL1 Ternary Complexes

As summarized above, the present disclosure provides methods for identifying an agent that disrupts a ternary complex including CRY1, CLOCK, and BMAL1. The methods include combining a CRY1 protein including the CRY1 photolyase homology region (PHR), a CLOCK PAS-B domain, and a test agent, under conditions suitable for CRY1-CLOCK PAS-B domain complex formation. The methods further include assessing CRY1-CLOCK PAS-B domain complex formation, where inhibition of CRY1-CLOCK PAS-B domain complex formation (e.g., as compared to conditions in which the test agent is absent, and/or below a pre-determined cut-off level) identifies the test agent as an agent that disrupts a ternary complex comprising CRY1, CLOCK, and BMAL1.

As used herein, a "CRY1 protein comprising the CRY1 photolyase homology region (PHR)" encompasses full-length CRY1 proteins as well as fragments thereof that include the PHR. The CRY1 protein may be a variant full-length CRY1 protein or fragment thereof, which variant has a secondary pocket that interacts with a CLOCK PAS-B domain in the same or substantially the same manner as a wild-type CRY1 secondary pocket. Details regarding the manner in which a wild-type CRY1 secondary pocket interacts with a CLOCK PAS-B domain, and example approaches for determining the manner in which a wild-type CRY1 secondary pocket interacts with a CLOCK PAS-B domain, are provided in the Experimental section below. A variant CRY1 protein may include, e.g., one or more amino acid substitutions, insertions, or deletions, relative to the corresponding wild-type CRY1 protein. The CRY1 protein may be fused to a heterologous peptide or polypeptide, e.g., a tag (e.g., a His tag or the like), a surface display protein (e.g., a yeast Aga2p cell wall protein), etc. In certain aspects, the CRY1 protein is a human CRY1 protein. In some embodiments, the CRY1 protein is a mouse CRY1 protein. In some embodiments, the CRY1 protein includes the CRY1 secondary pocket and includes or consists of an amino acid sequence having 70% or greater, 75% or greater, 80% or greater, 85% or greater, 90% or greater, 95% or greater, or 100% amino acid sequence identity to the amino acid sequence set forth in SEQ ID NO:7 or SEQ ID NO:8.

The "CLOCK PAS-B domain" employed in the subject methods encompasses full-length CLOCK PAS-B domains and fragments thereof, as well as CLOCK PAS-B domains that include one or more non-PAS-B domain regions of the CLOCK protein, such as from 1 to 100 amino acids from non-PAS-B domain regions of the CLOCK protein, e.g., from 1 to 10, 10 to 20, 20 to 30, 30 to 40, 40 to 50, 50 to 60, 60 to 70, 70 to 80, 80 to 90, 90 to 100, etc. amino acids from non-PAS-B domain regions of the CLOCK protein. In certain aspects, the one or more non-PAS-B domain regions of the CLOCK protein is a region contiguous with the PAS-B domain in a wild-type CLOCK protein. The CLOCK PAS-B domain employed in the subject methods is capable of binding the secondary pocket of CRY1 in the same or substantially the same manner as a wild-type CLOCK PAS-B domain. Details regarding the manner in which a wild-type CLOCK PAS-B domain interacts with the secondary pocket of CRY1, and example approaches for determining the manner in which a PAS-B domain interacts with the secondary pocket of CRY1, are provided in the Experimental section below. The CLOCK PAS-B domain may be a variant CLOCK PAS-B domain. For example, the CLOCK PAS-B domain may include one or more amino acid substitutions, insertions, or deletions, relative to the corresponding wild-type CLOCK PAS-B domain. The CLOCK PAS-B domain may be fused to a heterologous peptide or polypeptide, e.g., a tag (e.g., a His tag or the like), a surface display protein (e.g., a yeast Aga2p cell wall protein), etc. In certain aspects, the CLOCK PAS-B domain is a human CLOCK PAS-B domain. The amino acid sequences of the wild-type human and mouse CLOCK PAS-B domains are identical (see underlined regions in Table 1). In some embodiments, the CLOCK PAS-B domain is capable of binding the secondary pocket of CRY1 in the same or substantially the same manner as a wild-type CLOCK PAS-B domain, and includes or consists of an amino acid sequence having 70% or greater, 75% or greater, 80% or greater, 85% or greater, 90% or greater, 95% or greater, or 100% amino acid sequence identity to the amino acid sequence set forth in SEQ ID NO:10 or SEQ ID NO:11.

The CRY1 protein, the CLOCK PAS-B domain, or both, may include a detectable label, e.g., by fusion or conjugation to a detectable label. Detectable labels of interest include, but are not limited to, fluorescent labels, fluorescence resonance energy transfer (FRET) labels, radiolabels, colorimetric labels, biotin, avidin, streptavidin, etc.

The combining step may be carried out in a variety of ways and formats. For example, in certain aspects, the combining step includes combining the CRY1 protein with the CLOCK PAS-B domain to form CRY1-CLOCK PAS-B domain complexes in the absence of the test agent, and subsequently combining the test agent and the CRY1-CLOCK PAS-B domain complexes. In other aspects, the combining step includes combining the CRY1 protein with the test agent, and subsequently combining the CLOCK PAS-B domain with the CRY1 protein and test agent. Example approaches for producing the CRY1 protein and CLOCK PAS-B domain (e.g., by recombinant protein expression) are described in detail in the Experimental section below.

The combining of the CRY1 protein, CLOCK PAS-B domain and test agent may occur in a suitable container, such as a tube, well, vial, or the like. According to certain embodiments, the components are combined in a well of a multi-well plate (e.g., a 96-well, 384-well, or other multi-well plate), permitting the methods to be carried out in high-throughput, e.g., using a library of test agents (e.g., a small molecule library). The components may be combined in a cell-free system. Alternatively, the components may be combined within a cell, e.g., a cell expressing the CRY1 protein and the CLOCK PAS-B domain may be treated with a test agent. In some embodiments, the combining step includes displaying the CRY1 protein on the surface of a cell or phage in the presence of the CLOCK PAS-B domain and test agent. In other embodiments, the combining step includes displaying the CLOCK PAS-B domain on the surface of a cell or phage in the presence of the CRY1 protein and test agent. Surface display approaches for interrogating protein-protein interactions on the surface of phage, bacterial cells, yeast cells (e.g., employing Aga2p fusion proteins), etc. are known.

A variety of test agents may be employed in the subject methods. In certain aspects, the test agent includes a flavin moiety. In some embodiments, the test agent is a folate derivative. In certain aspects, the test agent is a polymer, such as a peptide, a polypeptide, a polynucleotide, a polysaccharide, or the like. According to certain embodiments, the test agent is a CLOCK PAS-B domain or a variant thereof.

As summarized above, the methods include assessing CRY1-CLOCK PAS-B domain complex formation. By "assessing CRY1-CLOCK PAS-B domain complex formation" is meant measuring (e.g., qualitatively or quantitatively) the formation of CRY1-CLOCK PAS-B domain complexes in the presence of the test agent, or a remaining abundance of CRY1-CLOCK PAS-B domain complexes when such complexes are preformed and subsequently combined/contacted with the test agent.

Any suitable approach for assessing the presence of CRY1-CLOCK PAS-B domain complexes may be employed. Suitable approaches include those employed in other contexts to assess protein-protein interactions in the presence of agents being tested for the ability to disrupt such interactions. According to some embodiments, a fluorescence polarization (FP) assay is employed to assess CRY1-CLOCK PAS-B domain complex formation. An example of such an assay is described in the Experimental section below and schematically illustrated in FIG. 11. In some embodiments, and in the example schematically illustrated in FIG. 11, recombinantly expressed CLOCK PAS-B domain is covalently labeled with a fluorescent label and then incubated with purified CRY1 (residues 1-491 of the photolyase homology region (PHR)) at a concentration just above the equilibrium dissociation constant ($K_d$) to ensure complex formation. Complexes may be plated, e.g., in a 384-well format opaque plate, after which test agents (e.g., small molecule test agents) from a library of test agents may then be pinned into the plate alongside corresponding negative controls, e.g., DMSO negative controls. In this example, total fluorescence and fluorescence polarization are measured to calculate the overall FP ratio. A test agent that produces a low FP ratio (e.g., an FP ratio below a predetermined cutoff level, and FP ratio that is lower than the FP ratio of a corresponding negative control by a certain amount, and/or the like) indicates that the test agent inhibits CRY1-CLOCK PAS-B domain complex formation and, in turn, identifies the test agent as an agent that disrupts a ternary complex comprising CRY1, CLOCK, and BMAL1.

When the assessing is by a fluorescence-based assay (e.g., fluorescence polarization (FP) assay or other suitable fluorescence-based assay), the CRY1 protein, the CLOCK PAS-B domain, or both, may be fluorescently labeled. In some embodiments, the fluorescent labeling is site-specific. For example, the CRY1 protein, the CLOCK PAS-B domain, or both, may be fluorescently labeled at a desired site internal to the protein, or at a terminus of the protein. In one non-limiting example, the CLOCK PAS-B domain is site-specifically labeled at its N-terminus. Any suitable fluorescent label may be employed. In certain aspects, the fluorescent label is a Tetramethylrhodamine (TAMRA) fluorescent label or a derivative thereof. In some embodiments, the fluorescent label is a Fluorescein-based fluorescent label, such as a Fluorescein amidite (FAM) fluorescent label.

Protein labeling may be carried out using any suitable approach. In some embodiments, the CRY1 protein, the CLOCK PAS-B domain, or both, are labeled using a Sortase enzyme, e.g., Sortase A. Sortases comprise a family of membrane-associated transpeptidases that anchor proteins to the cell wall of Gram-positive bacteria. Sortase-mediated ligation reactions are applicable to any two proteins of interest, provided one contains an LPXTG motif as the sortase target and the other has a suitably exposed N-terminal glycine residue to serve as the incoming nucleophile. Both modifications (LPXTG, glycine) can be introduced using standard molecular cloning protocols. In addition, sortases A are readily expressed in soluble recombinant form and in excellent yield in *Escherichia coli*. The natural nucleophile, lipid II, can be replaced by any peptide with an oligoglycine (Gly1-5) at the N terminus (in many cases a single glycine suffices). In turn, the LPXTG-containing peptides can be decorated with any molecule accessible through chemical synthesis (e.g., fluorophores, biotin, cross-linkers, lipids, carbohydrates, nucleic acids). Thus, incubation of sortase, an LPXTG-containing protein or peptide and nucleophile on the target protein leads to the covalent attachment of that LPXTG peptide to the protein of interest in a site-specific manner.

Various assays other than a fluorescence polarization (FP) assay may be used to monitor the effect of test agents (e.g., small molecules, peptides or polypeptides, including antibodies and other biologics) on CRY1:CLOCK PAS-B complex formation, including surface plasmon resonance (SPR), size exclusion chromatography coupled to multi-angle light scattering (SEC-MALS), NMR spectroscopy, flow cytometry, or the like, including any combinations thereof.

Test agents that inhibit CRY1-CLOCK PAS-B domain complex formation in an initial screen may then be subjected to a dose-response to obtain an approximate $K_I$ for the disruption of the complex. Compounds that pass this test (reproducibility and dose dependence outside of the screening format) may be further investigated for activity as CRY1 secondary pocket drugs that inhibit formation of the CRY1:CLOCK PAS-B complex, and by extension, the CRY1:CLOCK:BMAL1 ternary complex. Such an agent/drug could be used as a circadian-targeted therapeutic to "reset" the transcription-translation feedback loop of the clock. By directly targeting the CLOCK-binding secondary pocket of CRY1, the mechanism of action of such agents/drugs is much more rapid and focused compared to kinase inhibitors that have previously been proposed to elicit similar effects.

The inventors have established conditions for crystallizing CRY1, such that high-resolution structural information on binding locations (e.g., determining binding to the secondary pocket)/modes of interaction may be obtained via x-ray crystallography. Agents that have been validated to disrupt the CRY1:CLOCK PAS-B complex could then be validated in a variety of steady-state and real-time cell-based assays of CLOCK:BMAL1 activity and regulation by CRY1.

In certain aspects, the methods of the present disclosure for identifying an agent that disrupts a ternary complex comprising CRY1, CLOCK, and BMAL1 further include performing one or more controls, such as a negative control, a positive control, or both. In some embodiments, the methods include performing a positive control using a positive control agent known to inhibit CRY1-CLOCK PAS-B domain complex formation. Such a method may include combining a CRY1 protein including the CRY1 photolyase homology region (PHR), a CLOCK PAS-B domain, and a positive control agent, under conditions suitable for CRY1-CLOCK PAS-B domain complex formation, where the positive control agent inhibits CRY1-CLOCK PAS-B domain complex formation. A dominant mutation in CRY1 which induces alternate splicing and exclusion of CRY1 Exon 11 was recently discovered in humans having a longer circadian period. Patke et al. (2017) *Cell* 169:203-215. The present inventors have determined how this mutation exerts biochemical control of CRY1 interactions with CLOCK:BMAL1. In summary, the peptide encoded by the 11th exon of CRY1 acts as an auto-inhibitory module to antagonize the interaction of CRY1 with CLOCK PAS-B. The inventors investigated whether a peptide encoded by CRY1 Exon 11 could serve as a positive control inhibitor of the CRY1-CLOCK PAS-B domain complex. As described in Example 10 below and shown in FIG. 13, a 23 residue peptide encoded by CRY1 Exon 11 is able to displace CLOCK PAS-B from the CRY1 PHR, demonstrating the utility of the peptide encoded by CRY1 Exon 11 as a positive control inhibitor in such assays.

Compositions

Also provided are compositions that include a CRY1:CLOCK:BMAL1 complex-disrupting agent of the present disclosure. The compositions may include, e.g., any of the CRY1:CLOCK:BMAL1 complex-disrupting agents described herein.

In certain aspects, the compositions include a CRY1:CLOCK:BMAL1 complex-disrupting agent of the present disclosure present in a liquid medium. The liquid medium may be an aqueous liquid medium, such as water, a buffered solution, and the like. One or more additives such as a salt (e.g., NaCl, $MgCl_2$, KCl, $MgSO_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), glycerol, and the like may be present in such compositions.

Pharmaceutical compositions are also provided. The pharmaceutical compositions include any of the CRY1:CLOCK:BMAL1 complex-disrupting agents of the present disclosure, and a pharmaceutically acceptable carrier. The pharmaceutical compositions generally include a therapeutically effective amount of the CRY1:CLOCK:BMAL1 complex-disrupting agent. By "therapeutically effective amount" is meant a dosage sufficient to produce a desired result, e.g., an amount sufficient to effect beneficial or desired therapeutic (including preventative) results, such as a desired resetting of the circadian clock in an individual having a circadian rhythm disorder, or the like.

A CRY1:CLOCK:BMAL1 complex-disrupting agent of the present disclosure can be incorporated into a variety of formulations for therapeutic administration. More particularly, the CRY1:CLOCK:BMAL1 complex-disrupting agent can be formulated into pharmaceutical compositions by combination with appropriate pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the CRY1:CLOCK:BMAL1 complex-disrupting agents of the present disclosure suitable for administration to an individual (e.g., suitable for human administration) are generally sterile and may further be free of detectable pyrogens or other contaminants contraindicated for administration to an individual according to a selected route of administration.

In certain aspects, the pharmaceutical compositions of the present disclosure are formulated for oral, parenteral, intravenous, intraperitoneal, intramuscular, topical, transdermal, subcutaneous, intranasal, mucosal, or sublingual administration.

In pharmaceutical dosage forms, the CRY1:CLOCK:BMAL1 complex-disrupting agent can be administered alone or in appropriate association, as well as in combination, with other pharmaceutically-active compounds. The following methods and excipients are merely examples and are in no way limiting.

For oral preparations, the CRY1:CLOCK:BMAL1 complex-disrupting agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The CRY1:CLOCK:BMAL1 complex-disrupting agents can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The pharmaceutical composition may be in a liquid form, a lyophilized form or a liquid form reconstituted from a lyophilized form, where the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

An aqueous formulation of the CRY1:CLOCK:BMAL1 complex-disrupting agent may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

Methods of Use

Also provided are methods of using the CRY1:CLOCK:BMAL1 complex-disrupting agent and compositions of the present disclosure.

In some embodiments, provided are methods for disrupting a CRY1:CLOCK:BMAL1 complex. Such methods include contacting a CRY1:CLOCK:BMAL1 complex with a CRY1:CLOCK:BMAL1 complex-disrupting agent of the present disclosure, including any of the CRY1:CLOCK:BMAL1 complex-disrupting agents described herein. The agent may be present in a composition of the present disclosure.

The contacting may occur in vitro. For example, the contacting may include combining an agent of the present disclosure with a CRY1:CLOCK:BMAL1 complex in a cell-free medium in a tube, vial, well, or the like.

In some embodiments, the contacting occurs in vivo. An example in vivo embodiment includes treating cells (e.g., cultured cells (e.g., in a tube, vial, well, or the like) or cells present in an individual in need thereof) expressing CRY1, CLOCK, and BMAL1 with an agent of the present disclosure, where the agent enters the cell and disrupts a CRY1:CLOCK:BMAL1 complex therein. When the agent is a peptide or polypeptide (e.g., a CLOCK PAS-B domain, variant thereof, or other suitable peptide or polypeptide), the contacting may include transforming/transfecting the cells with a nucleic acid encoding the agent, operably linked to a suitable promoter, for expression in the cells and, in turn, disruption of CRY1:CLOCK:BMAL1 complexes therein. The peptide or polypeptide encoded by the nucleic acid may be such that the peptide or polypeptide enters the nucleus of the cell and disrupts CRY1:CLOCK:BMAL1 complexes therein. For example, the nucleic acid may encode a peptide or polypeptide having a nuclear localization signal (NLS) and/or other component to facilitate transport of the peptide or polypeptide into the nucleus.

In certain aspects, a method of present disclosure includes administering to an individual in need thereof a therapeutically effective amount of a CRY1:CLOCK:BMAL1 complex-disrupting agent or pharmaceutical composition of the present disclosure. Any of the CRY1:CLOCK:BMAL1 complex-disrupting agents or pharmaceutical compositions of the present disclosure may be administered.

In certain aspects, the individual in need thereof has a circadian rhythm disorder. Non-limiting examples of circadian rhythm disorders include shift-work sleep disorder, jet lag, metabolic imbalance, delayed sleep phase syndrome (DSPS), advanced sleep phase syndrome (ASPS), non-24-hour sleep-wake syndrome, and irregular sleep-wake rhythm. In some embodiments, the individual in need thereof is a shift worker (that is, someone who works substantially outside the traditional 9 am-5 pm day, such as evening or night shifts), a long-distance traveler, a submariner, an astronaut, a miner, or the like.

Human physiology and behavior are coordinated at the molecular level to exist in harmony with the earth's 24-hour solar cycle. Regulation on the circadian timescale provides homeostatic stability within an ever-changing environment by orchestrating daily changes throughout nearly all the tissues in the body. Disruption of this systemic synchronization leads to discordant physiological states marked by an increase in, e.g., metabolic disorders, cardiovascular disease, premature aging and cancer. In addition, circadian disruption has a dramatic effect on sleep and psychiatric and mood disorders, e.g., seasonal affective disorder, depression and bipolar disorder.

At the molecular level, the circadian clock regulates cellular homeostasis by driving the transcription and translation of over 40% of the genome to generate a peak of protein expression for each target gene once per day. As a result of this circadian regulation, the peak activities of most cellular processes, including DNA replication/cell division, nucleotide excision repair, and the response to immune challenges are limited to specific times of day.

As a diurnal species, the phase of the human internal clock is adjusted by light each day to maintain alignment of the active phase with daylight. This relationship with light can influence health adversely by causing circadian desynchronization. Inadequate or inappropriately timed lighting cues, including exposure to light at night from shift work, or through long-distance trans-meridian travel, can lead to rapid misalignment of cellular circadian clocks that disrupt the system-wide orchestration of circadian-controlled physiology. On average, it takes about 5-7 days to re-entrain (align rhythms with the new light/dark cycle) to a new environment. Therapeutic agents that reinforce circadian timing, help to maintain alignment in non-native light dark cycles, or speed up re-entrainment would have a significant impact on human health.

In certain aspects, the methods/agents of the present disclosure find use in resetting the circadian transcription/translation feedback loop upon administration to an individual. In some embodiments, such resetting: assists in realignment (e.g., rapid realignment) of circadian clocks with the environment for, e.g., shift workers, long-distance travelers, those with non-24 hour light/dark rhythms (e.g., submariners, astronauts, miners, etc.), etc.; reinforces circadian-driven sleep/wake cycles in the elderly and in patients with psychiatric disorders such as bipolar disorder and schizophrenia, where regular sleep schedules improve quality of life; restores typical circadian-driven sleep/wake cycles, e.g., for those with the Delayed Sleep Phase Disorder, e.g., resulting from CRY1 Exon 11 deletion; offsets the metabolic consequences of circadian misalignment resulting from exposure to light at night; enhances clock-mediated expression of protective genes across nearly all tissues of the body (e.g., to help with the decline in circadian function (and concomitant decreases in systemic health) in the elderly, etc.); promotes circadian alignment in conjunction with other FDA-approved drugs that have marked time-of-day effects due to the fact that their targets are under circadian control; and any combination thereof.

The CRY1:CLOCK:BMAL1 complex-disrupting agent may be administered alone (e.g., in monotherapy) or in combination (e.g., in combination therapy) with one or more additional therapeutic agents.

In some embodiments, an effective amount of the CRY1:CLOCK:BMAL1 complex-disrupting agent (or pharmaceutical composition including same) is an amount that, when administered alone (e.g., in monotherapy) or in combination (e.g., in combination therapy) with one or more additional therapeutic agents, in one or more doses, is effective to reduce the symptoms of a circadian rhythm disorder in the individual by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the symptoms in the individual in the absence of treatment with the CRY1:CLOCK:BMAL1 complex-disrupting agent or pharmaceutical composition.

In certain aspects, the methods of the present disclosure reset the circadian clock in cells of the individual when the CRY1:CLOCK:BMAL1 complex-disrupting agent or pharmaceutical composition is administered in an effective amount.

The CRY1:CLOCK:BMAL1 complex-disrupting agent or pharmaceutical composition may be administered to an individual using any available method and route suitable for drug delivery, including in vivo and ex vivo methods, as well as systemic and localized routes of administration. Conventional and pharmaceutically acceptable routes of administration include oral, intranasal, intramuscular, intra-tracheal, subcutaneous, intradermal, topical application, transdermal, ocular, intravenous, intra-arterial, intraperitoneal, intranasal, mucosal, and other enteral and parenteral routes of administration, including any combinations thereof. Routes of administration may be combined, if desired, or adjusted depending upon the CRY1:CLOCK:BMAL1 complex-disrupting agent and/or the desired effect. The CRY1:CLOCK:BMAL1 complex-disrupting agents or pharmaceutical compositions may be administered in a single dose or in multiple doses.

A variety of individuals are treatable according to the subject methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the individual is a human.

By "therapeutic", "therapeutically effective", "treating" or "treatment" is meant at least an amelioration of the symptoms associated with, e.g., a circadian rhythm disorder, where amelioration is used in a broad sense to refer to at least a reduction in the magnitude of a parameter, e.g. symptom, associated with, e.g., a circadian rhythm disorder being treated. As such, treatment also includes situations where a circadian rhythm disorder, or at least symptoms associated therewith, are completely inhibited, e.g., prevented from happening, or stopped, e.g., terminated, such that the individual no longer suffers from the circadian rhythm disorder, or at least the symptoms that characterize the circadian rhythm disorder.

Dosing is dependent on severity and responsiveness of the disease state to be treated. Optimal dosing schedules can be calculated from measurements of drug accumulation in the body of the patient. The administering physician can determine optimum dosages, dosing methodologies and repetition rates. Optimum dosages may vary depending on the relative potency of individual CRY1:CLOCK:BMAL1 complex-disrupting agents, and can generally be estimated based on $EC_{50}$s found to be effective in in vitro and in vivo animal models, etc. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, where the CRY1:CLOCK:BMAL1 complex-disrupting agent or pharmaceutical composition is administered in maintenance doses, ranging from 0.01 µg to 100 g per kg of body weight, once or more daily, to once every several months, once every six months, once every year, or at any other suitable frequency.

The therapeutic methods of the present disclosure may include administering a single type of CRY1:CLOCK:BMAL1 complex-disrupting agent to the individual, or may include administering two or more types of CRY1:CLOCK:BMAL1 complex-disrupting agents to an individual by administration of a cocktail of different CRY1:CLOCK:BMAL1 complex-disrupting agents.

In some embodiments, the methods include, prior to the administering the CRY1:CLOCK:BMAL1 complex-disrupting agent or pharmaceutical composition, identifying the individual as having a circadian rhythm disorder. A variety of suitable approaches are available to identify an individual as having a circadian rhythm disorder. In certain aspects, the identification includes having the individual provide information regarding her/his sleep patterns (e.g., via interview, questionnaire, and/or the like), monitoring the sleep of the individual (e.g., using available sleep monitoring devices), or a combination thereof. In certain aspects, the individual is identified as having a circadian rhythm disorder based on the individual being a shift worker, a long-distance traveler, a submariner, an astronaut, a miner, or the like.

In some embodiments, identifying the individual as having a circadian rhythm disorder includes testing the individual for a genetic mutation associated with a circadian rhythm disorder. In certain aspects, the individual is tested for one or more genetic mutations in a gene encoding CRY1, CRY2, CLOCK, BMAL1, ARNTL, PER1, PER2, PER3, and any combinations thereof. In some embodiments, identifying the individual as having a circadian rhythm disorder includes testing the individual for a mutation in the CRY1 gene, such as a gain-of-function mutation in the CRY1 gene. In one non-limiting example, the gain-of-function mutation is an adenine-to-cytosine transversion within the 5' splice site following Exon 11 in the CRY1 gene, which mutation causes skipping of Exon 11 (and in turn, absence of the amino acids encoded by Exon 11 in the CRY1 protein) and is associated with delayed sleep phase disorder (DSPD) as reported by Patke et al. (2017) *Cell* 169:203-215.

Kits

Also provided by the present disclosure are kits. In certain aspects, provided are kits that include a CRY1 protein including the CRY1 photolyase homology region (PHR), a CLOCK PAS-B domain, or both. Such kits may include any of the CRY1 proteins and/or CLOCK PAS-B domains described herein. Such kits may further include instructions for using the CRY1 protein, the CLOCK PAS-B domain, or both, in a screening assay for identifying an agent that disrupts a ternary complex comprising CRY1, CLOCK, and BMAL1. For example, the kits may include instructions for practicing any of the methods of the present disclosure for identifying an agent that disrupts a ternary complex including CRY1, CLOCK, and BMAL1. In some embodiments, the kits include a CRY1 protein including the CRY1 PHR, and a CLOCK PAS-B domain. The CRY1 protein, CLOCK PAS-B domain, or both, may be labeled, e.g., site-specifically labeled. In certain aspects, such a kit includes a CLOCK PAS-B domain that is site-specifically labeled at a terminus, such as the N-terminus. Labels of interest include, but are not limited to, fluorescent labels, such as a Tetramethylrhodamine (TAMRA) fluorescent label or a Fluorescein amidite (FAM) fluorescent label. The above-described kits may further include one or more negative and/or positive controls. In some embodiments, the kits include a positive control agent. For example, the kits may include a peptide encoded by Exon 11 of CRY1 as a positive control agent, as demonstrated in the Experimental section (Example 10) below. In certain aspects, the screening assay is a fluorescence polarization (FP)-based displacement assay as described in detail elsewhere herein. One or more components of the kits (e.g., a CRY1 protein, a CLOCK PAS-B domain, and/or a peptide encoded by Exon 11 of CRY1) may be provided in frozen form (e.g., as one or more frozen aliquots) for enhanced storage stability.

Also provided are kits that include an amount of any of the CRY1:CLOCK:BMAL1 complex-disrupting agents described herein, or any of the pharmaceutical compositions described herein, and instructions for using same in a particular application. In certain aspects, the kit provides a CRY1:CLOCK:BMAL1 complex-disrupting agent of the present disclosure and instructions for using the agent to disrupt CRY1:CLOCK:BMAL1 complexes in vitro or in vivo, e.g., for research purposes (e.g., for purposes of interrogating/elucidating mechanisms of the circadian clock, resetting the circadian clock in cells to "align"/synchronize the cells to the same or substantially the same stage of the circadian feedback loop (e.g., to control for differences in gene expression, etc. that result from cells being at different stages of the circadian cycle)), and/or the like.

In some embodiments, a kit of the present disclosure includes a therapeutically effective amount of any of the CRY1:CLOCK:BMAL1 complex-disrupting agents described herein, or any of the pharmaceutical compositions described herein, and instructions for administering the CRY1:CLOCK:BMAL1 complex-disrupting agent or pharmaceutical composition to an individual in need thereof, e.g., an individual identified as having a circadian rhythm disorder. According to certain embodiments, the kits include the CRY1:CLOCK:BMAL1 complex-disrupting agent or the pharmaceutical composition present in one or more unit dosages, such as 1, 2 or more, 3 or more, 4 or more, 5 or more, etc. unit dosages.

Components of the kits may be present in any suitable container(s), such as a tube, vial, or the like. Components of the kits may be present in separate containers, or multiple components may be present in a single container.

The instructions provided with a kit of the present disclosure may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

The following examples are offered by way of illustration and not by way of limitation.

EXPERIMENTAL

Introduction

The present inventors set out to identify how CRY1 interacts with CLOCK:BMAL1 to form a stable ternary complex. It was found that the photolyase homology region (PHR) of CRY1 binds directly to the second of two tandem PAS domains (PAS-B) of CLOCK, and single point mutations on CRY1 and CLOCK PAS-B that eliminate complex formation were identified. Using these data to guide HAD-DOCK modeling, it was found that CLOCK PAS-B docks directly into the secondary pocket of the CRY1 PHR. This pocket is evolutionarily conserved with photolyase, where it serves as the binding site for an antenna chromophore that is important for repair of UV-induced DNA damage. Small angle x-ray scattering (SAXS) studies of CRY1, CLOCK:BMAL1, and the CRY1:CLOCK:BMAL1 ternary complex highlight structural dynamics of these complexes and validate the inventors' low resolution model of the ternary complex. Together, these data illustrate how CRY1 exploits a conserved binding pocket to form a ternary complex with CLOCK:BMAL1 that maintains the transcription factor in a repressed state to close the circadian feedback loop.

Example 1—CRY1 Interacts Directly with the CLOCK-BMAL1 PAS Domain Core

The repressive activity of CRY1 is essential to generate circadian rhythms; one way that CRY1 does this is by binding the BMAL1 TAD to sequester it from co-activators. However, CRY1 has only moderate affinity ($K_d$~1 μM) for the isolated TAD, suggesting that it makes at least one other interaction with CLOCK:BMAL1 that allows it to serve as a potent repressor when expressed to near stoichiometric levels. Previous studies suggest the CLOCK PAS-B domain plays a role in repression by CRY1 (Xu et al. (2015) Nat Struct Mol Biol 22(6):476-484; Sato et al. (2006) Nature Genetics 38(3):312-319; Zhao et al. (2007) Nature Cell Biology 9(3):268-275), but no evidence exists for a direct interaction. To further explore the biochemical basis for interactions between CRY1 and CLOCK:BMAL1, the core photolyase homology region of mouse CRY1 (PHR) and a tandem PAS domain heterodimer (comprising PAS-A and PAS-B domains, PAS-AB) of mouse CLOCK:BMAL1 were purified (FIG. 1, panel A). Using size exclusion chromatography to follow complex formation, it was found that the CRY1 PHR directly bound the PAS-AB core of CLOCK:BMAL1 to form a ternary complex (FIG. 1, panel B). Further dissection of this interaction revealed that the CLOCK PAS-B domain alone was sufficient to bind CRY1 PHR. Moreover, while BMAL1 PAS-B shares the same protein fold as CLOCK PAS-B, it did not interact with CRY1, highlighting the specificity of this interaction (FIG. 1, panel C).

Figure 2:
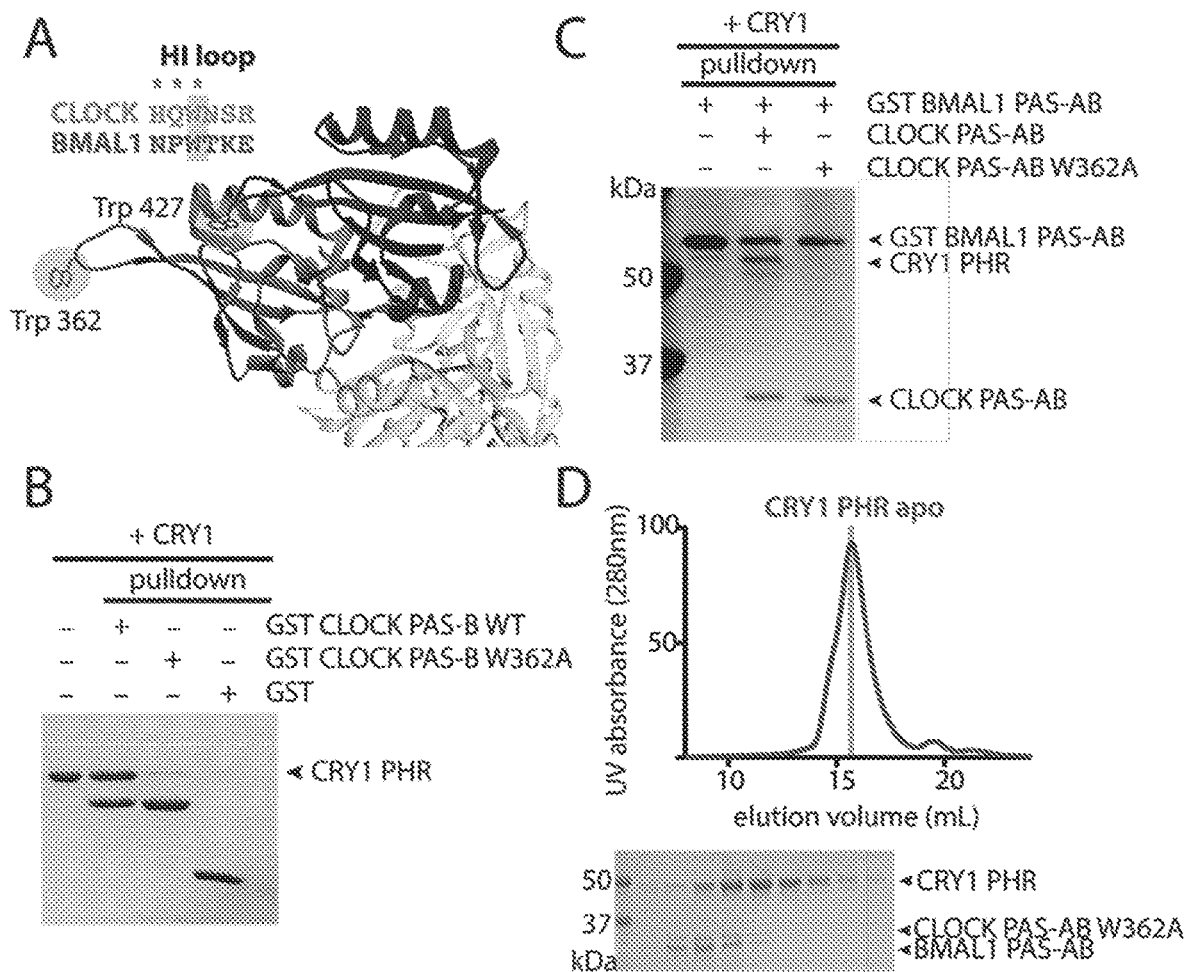
FIG. 2 depicts data demonstrating that a single point mutation disrupts CRY1:CLOCK:BMAL1 complex formation. Panel A: PAS-B domains of CLOCK:BMAL1 (PDB: 4F3L; CLOCK, BMAL1) with conserved tryptophan in HI loop shown in sticks. Asterisks indicate mutations in CLOCK that disrupt CRY1 repression of CLOCK:BMAL1. Adjacent PAS-A domains are shown. Panel B: GST pull-down assay of GST-CLOCK PAS-B and GST-CLOCK PAS-B W362A with CRY1 PHR. Panel C: GST pull-down assay of GST-BMAL1 PAS-AB alone, in the presence of CLOCK PAS-AB or CLOCK PAS-AB W362A with CRY1 PHR. Panel D: S200 10/300 GL SEC analysis of complex formation with CRY1 PHR and the PAS-AB dimer with W362A CLOCK mutation.

Several residues in the HI loop (connecting the Hβ and Iβ strands) of CLOCK PAS-B are important for CRY1-mediated repression of CLOCK:BMAL1 (Xu et al. (2015) Nat Struct Mol Biol 22(6):476-484; Sato et al. (2006) Nature Genetics 38(3):312-319; Zhao et al. (2007) Nature Cell Biology 9(3):268-275). The entire HI loop is freely accessible in the crystal structure of the CLOCK:BMAL1 bHLH-PAS dimer, protruding out from the PAS-B dimer interface (FIG. 2, panel A). To test the role of the HI loop in binding CRY1, a W362A substitution in CLOCK PAS-B was made and its ability to bind CRY1 was tested using a GST pull-down experiment. This single point mutation disrupted formation of the stoichiometric CRY1:CLOCK PAS-B complex (FIG. 2, panel B). The importance of W362 for the CRY1:CLOCK interaction in the context of a larger, tandem PAS domain dimer was then investigated. While GST-BMAL1 PAS-AB was able to pull down similar amounts of wild-type and W362A CLOCK PAS-AB, CRY1 was only present in a ternary complex with wild-type CLOCK PAS-AB (FIG. 2, panel C). Furthermore, a CLOCK:BMAL1 PAS-AB dimer possessing the W362A mutation no longer co-migrated with CRY1 on size-exclusion chromatography (FIG. 2, panel D). Collectively, these data demonstrate that stable association of CRY1 with the CLOCK:BMAL1 PAS domain core is predicated on a single, solvent-accessible tryptophan on CLOCK PAS-B.

Example 2—The CLOCK PAS-B Domain Docks into the CRY1 Secondary Pocket

Figure 3:
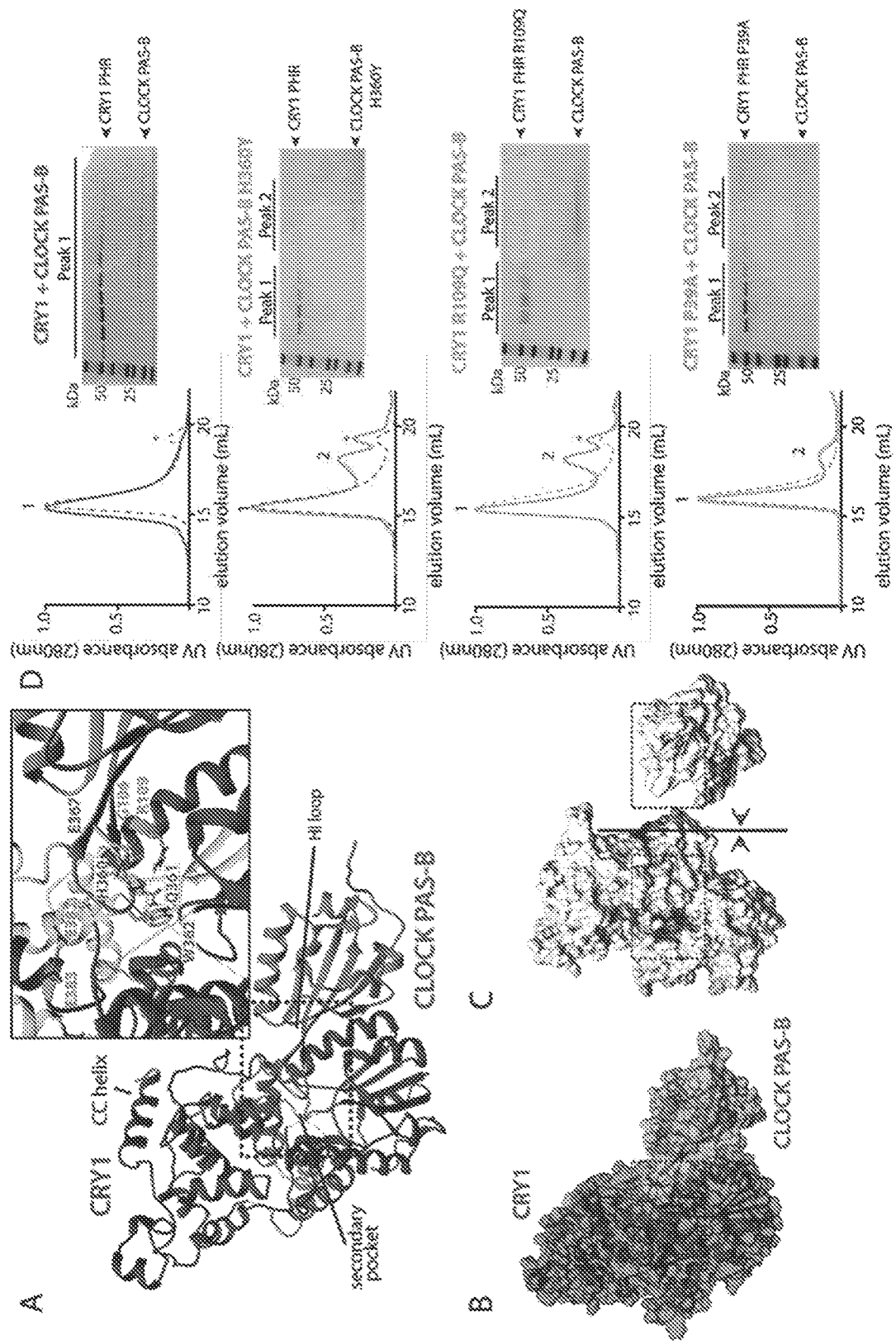
FIG. 3 provides data demonstrating that CLOCK PAS-B docks into the secondary pocket of CRY1. Panel A: Representative PDB from top HADDOCK cluster (cluster 1). Active residues used to guide the docking are shown. CRY1 PHR unstructured secondary pocket loop is shown in a dashed line. See Table 2 for details on HADDOCK cluster statistics. Panel B: Surface representation of CRY1:CLOCK PAS-B HADDOCK model. Panel C: Electrostatic representation of CRY1:CLOCK PAS-B HADDOCK model. Surface potential maps were generated using the Adaptive Poisson-Boltzmann Solver (APBS) in UCSF Chimera. The secondary pocket of CRY1 and HI loop of CLOCK PAS-B are highlighted in the dashed box analogous to panel A. Panel D: SEC analysis of the CRY1:CLOCK PAS-B interaction with mutants. Proteins were mixed and incubated at ~30 min. at 4° C. and then injected on a S200 10/300 GL column. Top, wild-type CRY1 PHR and CLOCK PAS-B. Asterisk, slight UV-absorbing contaminant. Numbers above peaks correspond to fractions analyzed by SDS-PAGE and Coomassie stain at right. Top middle, wild-type CRY1 PHR and CLOCK PAS-B H360Y mutant. Bottom middle, CRY1 PHR R109Q mutant with wild-type CLOCK PAS-B. Bottom, CRY1 PHR P39A mutant with wild-type CLOCK PAS-B. Residue P39 is located in the disordered loop shown in a dashed line in panel A. Elution profiles of CRY1 PHR WT or mutant alone are shown in each respective panel in the dashed line.

To better understand the nature of the CRY1:CLOCK PAS-B interface, a computational model of the complex was generated using HADDOCK (High Ambiguity Driven protein-protein DOCKing). HADDOCK utilizes residues identified from experimental studies to guide selection of probable protein-protein interfaces and then performs rigid body docking and simulated annealing protocols to provide clusters of hits that are ranked by energetic considerations and their similarity to one another. Based on previous mutagenesis data and the present studies, the following residues as active restraints were used, defined by their importance for binding and solvent accessibility: CRY1: G106, R109, E383, E382 and CLOCK PAS-B: G332, H360, Q361, W362, E367 (FIG. 3, panel A). The CRY1 restraints cluster around the secondary pocket in the PHR, which is structurally conserved with photolyase where it serves as a chromophore binding pocket. The existing crystal structure of mouse CRY1 lacks a short, flexible loop adjacent to this pocket, so the inventors solved a structure of the mouse CRY1 PHR (1.8 Å resolution) in a new space group with the goal of visualizing this loop (PDB: 5T5X). While the new structure also lacked density for this loop, it was of higher resolution so it was used along with the CLOCK PAS-B domain (isolated from PDB: 4F3L) for HADDOCK modeling. Clusters were ranked using electrostatic, van der Waals, and ambiguous interaction restraint energy terms. All four clusters docked the HI loop of CLOCK PAS-B into the secondary pocket of CRY1 in similar orientations (FIG. 4, panel A) with the top cluster populated by the greatest number of models (118) and the best overall HADDOCK score (Table 2).

TABLE 2

HADDOCK Cluster Statistics

|  | Cluster 1 | Cluster 2 | Cluster 3 | Cluster 4 |
| --- | --- | --- | --- | --- |
| HADDOCK score | −147.3 | −131.6 | −109.5 | −132.1 |
| Cluster size | 118 | 43 | 15 | 13 |
| RMSD lowest-energy structure | 12.7 ± 0.2 | 13.3 ± 0.2 | 11.0 ± 0.8 | 2.8 ± 2.0 |
| Van der Walls energy | −47.4 ± 3.8 | −47.4 ± 4.1 | −40.1 ± 7.3 | −51.9 ± 9.9 |
| Electrostatic energy | −289.5 ± 42.7 | −243.0 ± 31.0 | −213.8 ± 52.9 | −206.9 ± 18.3 |
| Desolvation energy | −44.5 ± 7.6 | −36.7 ± 5.9 | −30.9 ± 7.7 | −41.0 ± 7.2 |
| Restraints violation energy | 24.1 ± 25.04 | 11.5 ± 14.27 | 43.7 ± 11.91 | 22.2 ± 17.36 |
| Buried surface area | 1944.5 ± 83.2 | 1869.0 ± 46.2 | 1446.6 ± 114.9 | 1839.6 ± 105.4 |
| Z-score | −1.3 | −0.1 | 1.5 | −0.1 |

Figure 4:
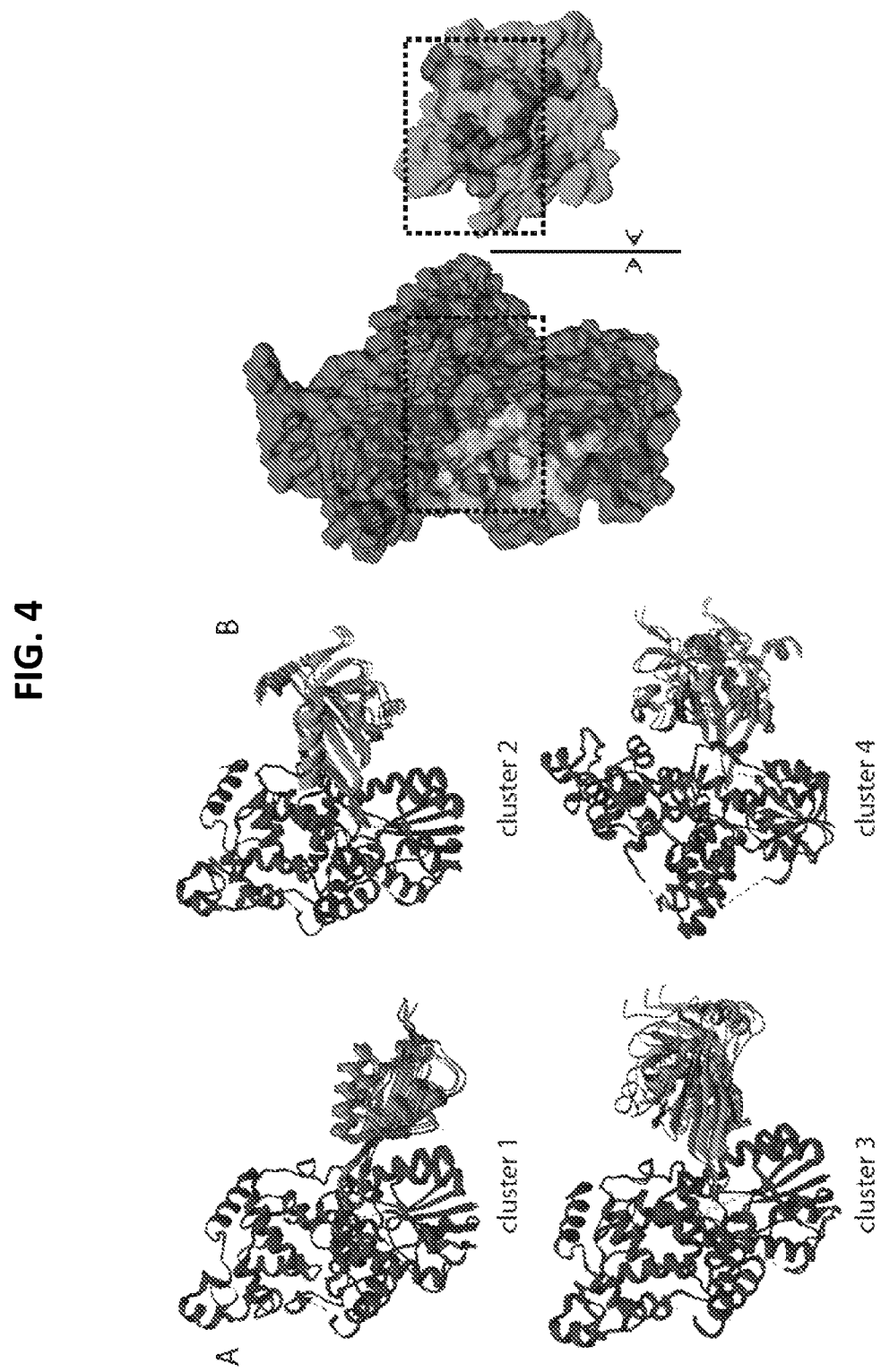
FIG. 4 shows CRY1:CLOCK PAS-B HADDOCK modeling. Panel A: All docking solutions from HADDOCK 2.2 analysis of CRY1:CLOCK PAS-B interaction. Clusters are ranked numerically according to lowest HADDOCK scoring. See Table 2 for details of cluster scoring. Panel B: Buried surface area representation of CRY1 and CLOCK PAS-B for top HADDOCK cluster 1 PDB using built-in chimera tools. Buried surface of CRY1 and CLOCK PAS-B shown. Buried surface area calculated by HADDOCK: 1944.5±83.2 Å$^2$.

A representative model from the top cluster is characterized by a large buried surface area (1994.5±83.2 Å$^2$) mediated by burial of the HI loop and additional sites of contact between the β-sheet of CLOCK PAS-B and CRY1 (FIG. 3, panel B and FIG. 4, panel B). Complementary electrostatic contacts at the interface (FIG. 3, panel C) were also noted. To test this model experimentally, additional point mutations at the observed interface were made. CLOCK PAS-B H360Y and two mutations in CRY1 (P39A and R109Q) each disrupted formation of a CRY1:CLOCK PAS-B complex as shown by loss of CLOCK PAS-B co-migration with CRY1 (peak 1) and the presence of a new peak for the isolated CLOCK PAS-B domain (peak 2) by size exclusion chromatography (FIG. 3, panel D). This is consistent with the inability of CRY1 R109Q to co-immunoprecipitate with CLOCK:BMAL1 and reconstitute circadian rhythms in cell-based cycling assays. Additionally, mutations that eliminate CRY1:CLOCK PAS-B complex formation in vitro also significantly reduce repressive activity of full-length mCRY1 in steady-state luciferase reporter assays (FIG. 5), surprisingly demonstrating that these phenotypes are mediated by a direct interaction between CRY1 and the CLOCK:BMAL1 complex at the secondary pocket.

Figure 6:
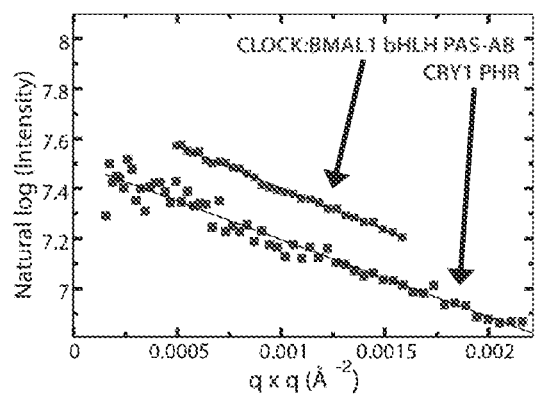
FIG. 6 depicts small angle x-ray scattering (SAXS) profile data of CRY1 and CLOCK:BMAL1 bHLH PAS-AB. Panel A: Guinier analysis of both CLOCK:BMAL1 bHLH PAS-AB and CRY1 PHR show no aggregation indicated by the linear dependence of log(I(q)) vs. q$^2$. SAXS calculated molecular weight for CRY1 PHR: 45 kDa, CLOCK:BMAL1 bHLH PAS-AB: 78 kDa. Panel B: Kratky plot of CLOCK:BMAL1 dimer and CRY PHR show mostly folded character and an elongated shape.
Figure 6:
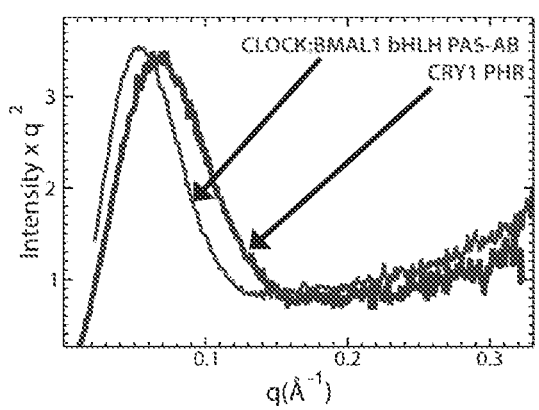
Figure 7:
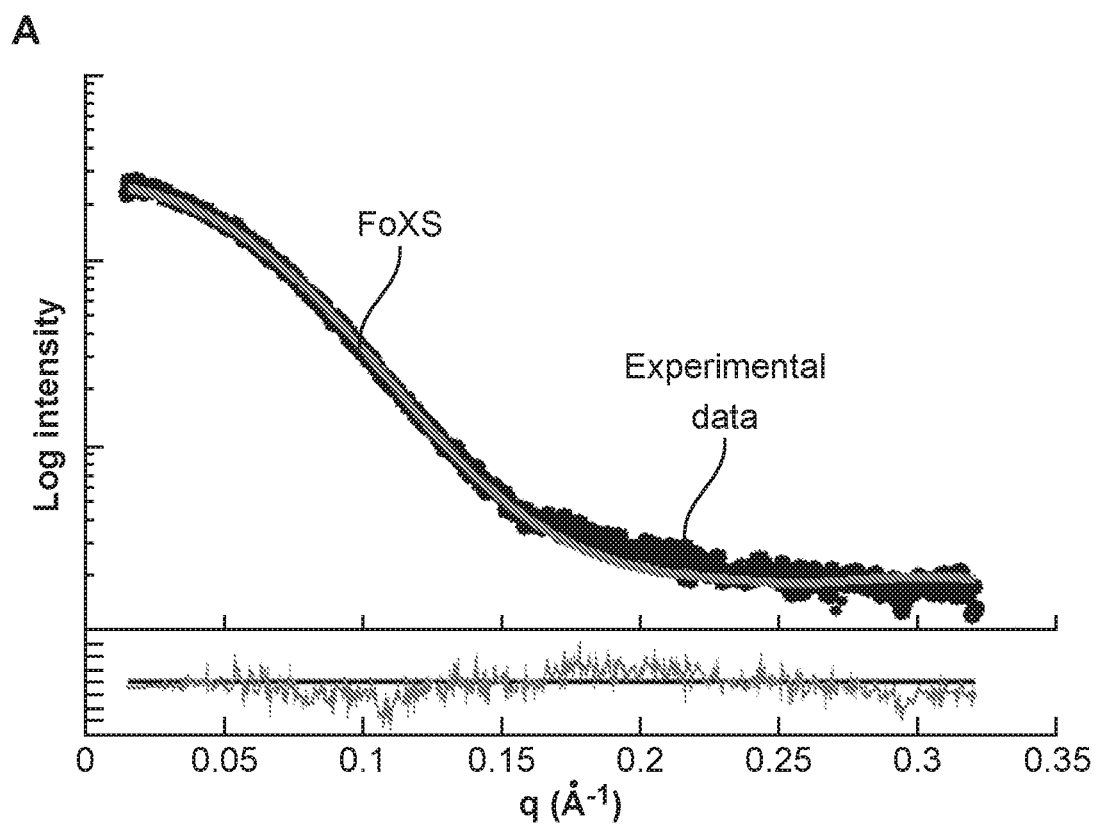
FIG. 7 depicts data indicating that the CRY1 PHR is compact and CLOCK:BMAL1 bHLH-PAS-AB dimer is highly flexible in solution. Panel A: Solution x-ray scattering profile for CRY1 PHR compared to the theoretical scattering profile for CRY1 PHR (PDB: 5T5X) calculated by the FoXS server. Residuals for the fit are shown below with an overall χ=1.13. Panel B: The crystal structure of CRY1 PHR fit into the solution envelope generated from the SAXS data. Panel C: Solution x-ray scattering profile for the CLOCK:BMAL1 PAS-AB dimer compared to the theoretical scattering profile calculated from PDB: 4F3L by the FoXS server. Multi-state modeling of flexible regions within the dimer was performed with HingeProt paired with MultiFoXS. Panel D: A representative PDB from the top MultiFoXS hit that includes flexible loops not visible in the crystal structure aligned with PDB: 4F3L using the PAS-A domain of BMAL1. Arrows indicate regions of predicted flexibility.
Figure 7:
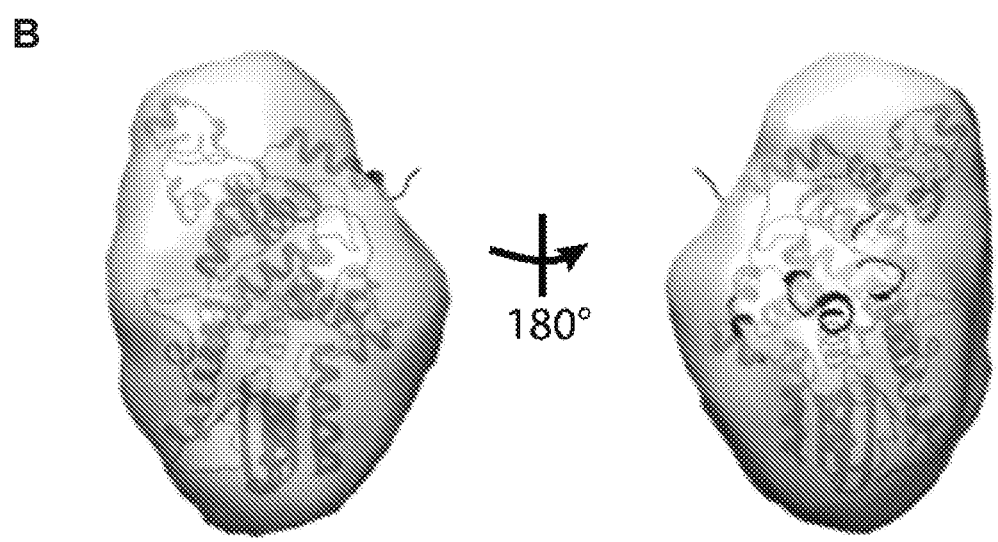
Figure 7:
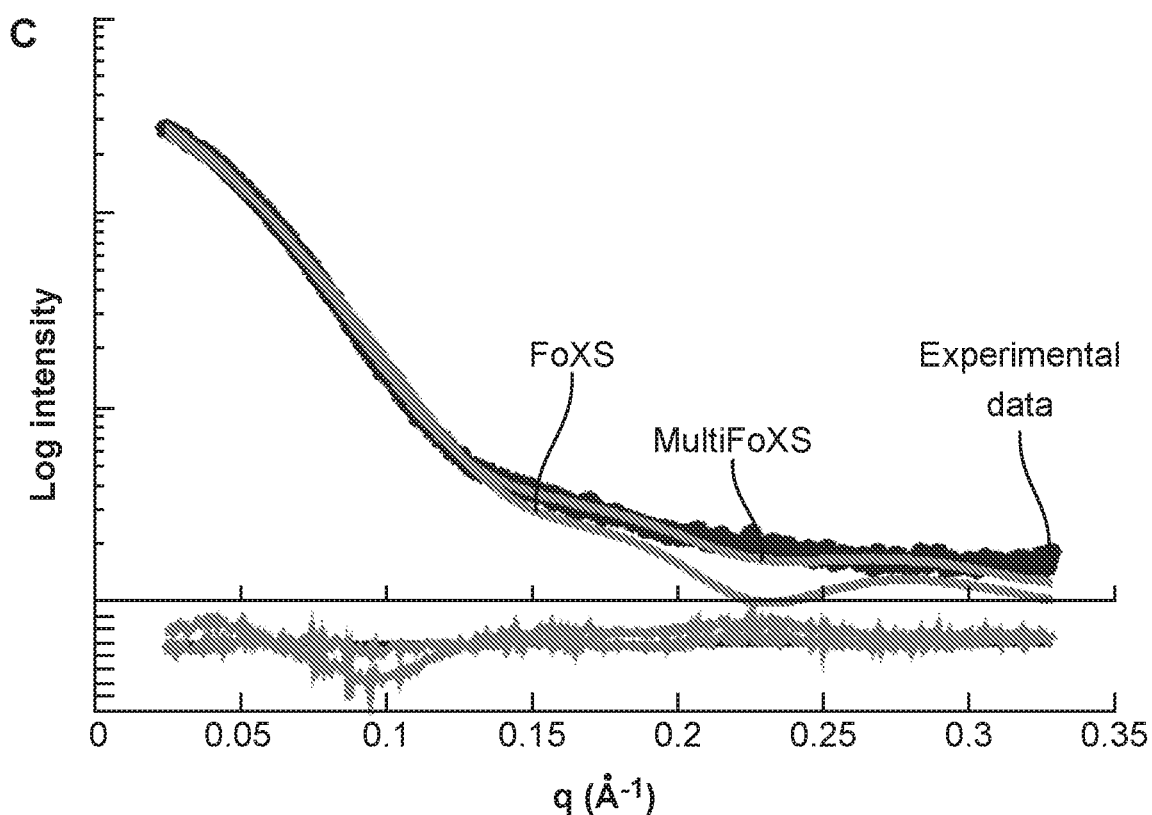
Figure 7:
Figure 8:
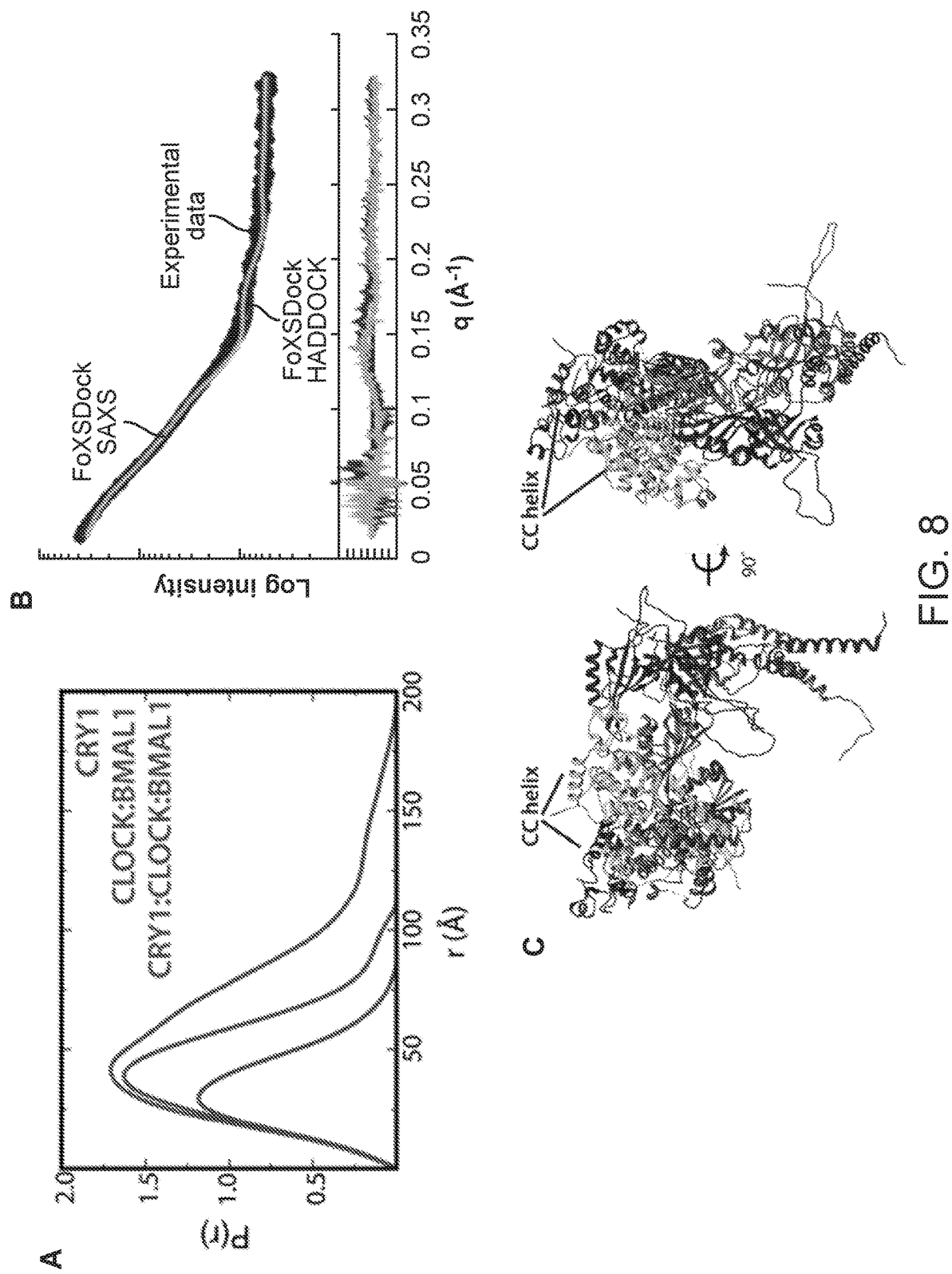
FIG. 8 provides data relating to a model for the CRY1:CLOCK:BMAL1 repressive complex. Panel A: Pairwise distribution function of complexes in the current study. CRY1 PHR, D$_{max}$=86 Å (lowest peak); CLOCK:BMAL1 bHLH-PAS-AB dimer, D$_{max}$, 115 Å (middle peak); CRY1:CLOCK:BMAL1 ternary complex, D$_{max}$, 195 Å (highest peak). Panel B: Solution x-ray scattering curve for the ternary complex. Docking of CRY1 onto CLOCK:BMAL1 was restrained by the SAXS profile using FoXSDock. The model with the best combined SAXS and energy score is shown (χ=2.22). The FoXSDock HADDOCK structure is among these top scoring models that most closely represent the CRY1 PHR:CLOCK PAS-B HADDOCK model. See FIG. 9, Panel D for representative PDB of the FoXSDock HADDOCK scattering profile shown in the scattering trace. Panel C: Top FoXSDock model aligned with the HADDOCK model from FIG. 2 using the CLOCK PAS-B domain. Panel D: SEC analysis of CRY1 PHR mixed with CLOCK:BMAL1 PAS-B heterodimer. Proteins were mixed and incubated at ~30 min. at 4° C. and then injected on a S200 10/300 GL column. Panel E: Peak fractions were analyzed by SDS-PAGE and stained with Coomassie. Panel F: Cartoon model of the late repressive CRY1:CLOCK:BMAL1 repressive complex.
Figure 8:
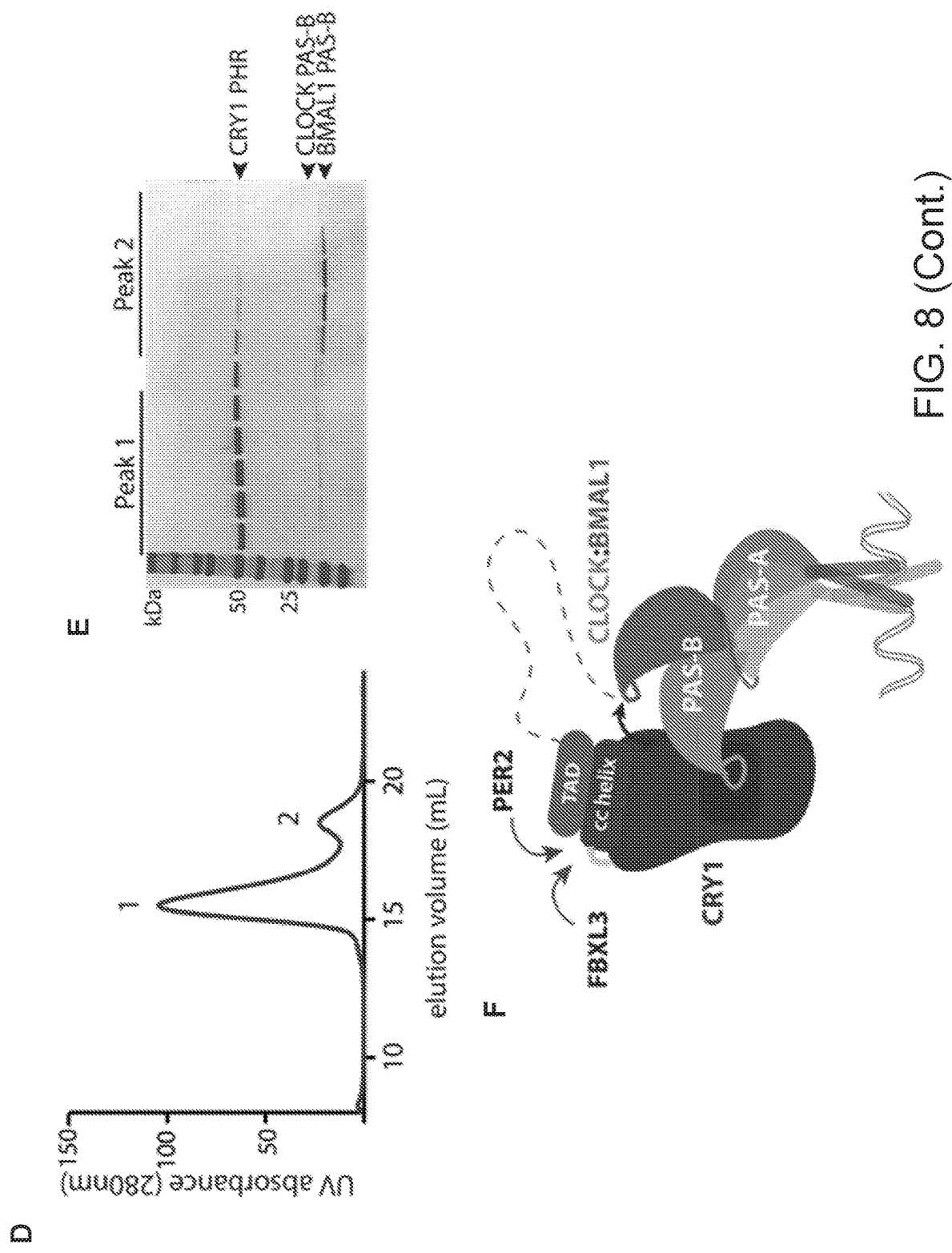

Example 3—Solution Scattering Studies Highlight Flexibility of Clock Protein Complexes To examine the behavior of the late circadian repressive complex in more detail, the solution-based technique of small angle x-ray scattering (SAXS) was employed. First performed was SAXS analysis on the isolated CRY1 PHR and CLOCK:BMAL1 bHLH PAS-AB heterodimer individually to provide insight into their behavior before assembling the ternary complex. Scattering data were collected at several concentrations; both CRY1 PHR and CLOCK:BMAL1 bHLH PAS-AB samples were well-behaved, showing no radiation damage or aggregation as demonstrated by Guinier analysis (FIG. 6). The mass and radius of gyration determined from our analysis of the SAXS data agreed with values calculated from the crystal structures of CRY1 and CLOCK:BMAL1 bHLH PAS-AB. The SAXS profile calculation server FoXS was then used to generate a theoretical scattering profile of CRY1 PHR based on the inventors' crystal structure (FIG. 7, panel A). Comparison of the theoretical scattering profile to the experimental data provided a fit within the noise ($\chi=1.13$), indicating that CRY1 PHR maintains a compact structure in solution that is similar to its crystal structure. Moreover, our crystal structure of CRY1 PHR fit well into a corresponding solution envelope consistent with the pairwise distribution function (FIG. 7, panel B and FIG. 8, panel A).

By contrast, the experimental scattering profile of the CLOCK:BMAL1 bHLH PAS-AB heterodimer was not well fit by the theoretical scattering profile calculated from its crystal structure (FoXS, $\chi=5.93$) (FIG. 7, panel C). The PAS-A domains of CLOCK and BMAL1 both possess long, flexible loops that are not observed in the crystal structure (12% and 26% of the sequence, respectively). To better describe the motions of these dynamic regions, MODELLER v9.15 was used to build in the missing fragments and MultiFoXS to sample a range of possible conformations constrained by the SAXS data. As a result, the inventors found conformations that fit the experimental scattering profile within the noise ($\chi=1.43$) (FIG. 7, panel D). The top structural ensemble resulting from this analysis highlighted two main findings: 1) the loops absent from the crystal structure are highly flexible in solution and contribute significantly to the scattering profile of the PAS domain core, and 2) the interface between CLOCK and BMAL1 PAS-B domains may be dynamic. Best fits were obtained using a model where the PAS-B domains were able to sample an undocked state, suggesting that the PAS-B domains may exist in more than one state in solution. Given that multiple regions within the PAS domain core of CLOCK:BMAL1 are known to be important for its function, characterization of their dynamic behavior in solution could begin to shed light on their role in regulation of DNA binding and/or CLOCK:BMAL1 transcriptional activity.

Example 4—Low-Resolution Model of the CRY1:CLOCK:BMAL1 Ternary Complex

Figure 9:
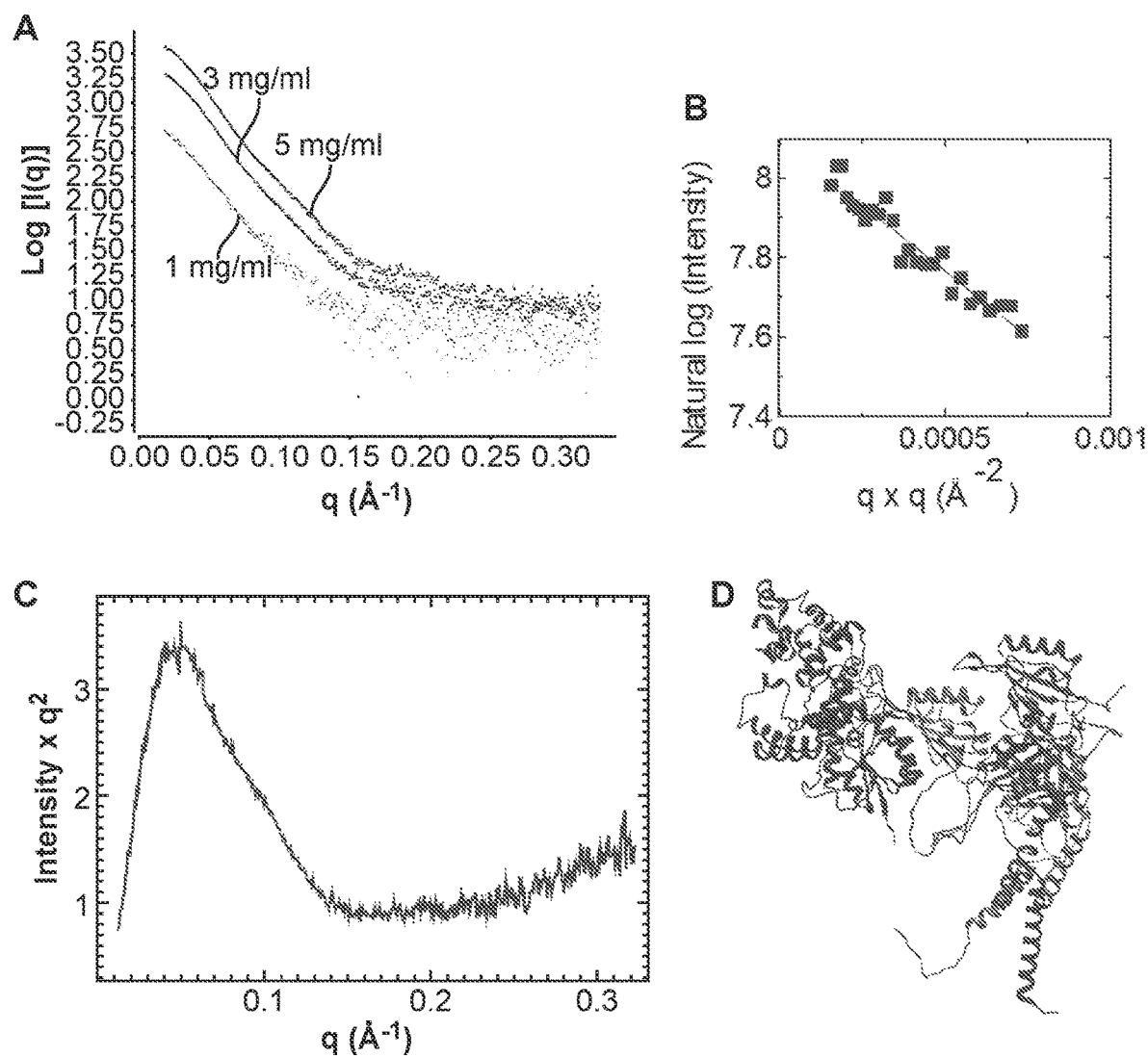
FIG. 9 depicts data relating to the small angle x-ray scattering profile of the CRY1:CLOCK:BMAL1 repressive complex. Panel A: Scattering traces of CRY1:CLOCK:BMAL1 ternary complex (CCB) at different concentrations are shown. These scattering plots were merged to generate the dataset as the input for FoXSDock. Panel B: Guinier analysis of CCB shows little or no aggregation of sample. SAXS calculated molecular weight of the ternary complex is 113 kDa. Panel C: Kratky plot shows the CCB complex indicates a folded mass with an elongated shape. Panel D: PDB of FoXSDock HADDOCK driven model that is amongst the top 20 nearly degenerate docking structures, χ=2.74.

The use of SAXS to guide and validate computational models of protein complexes can be a powerful tool with high-resolution structures in hand for individual components. To generate a low-resolution model for the ternary complex, the CRY1 PHR was purified together with the CLOCK:BMAL1 bHLH PAS-AB dimer as a stable ternary complex by size exclusion chromatography and SAXS data was collected (FIG. 8). Analysis of the scattering profiles confirmed the presence of all three molecules consistent with the molecular weight of the ternary complex (FIG. 9, panels A, B and C). Furthermore, the ternary complex showed a maximum particle size ($D_{max}$) of 195 Å, much longer than either CRY1 or CLOCK:BMAL1 alone (86 Å and 115 Å, respectively) (FIG. 8, panel A). The elongated $D_{max}$ of the ternary complex suggests that CRY1 extends out from the CLOCK:BMAL1 bHLH PAS-AB dimer.

Models for the ternary complex were assessed using two methods. First used was FoXSDock, which combines experimental data and analysis of calculated energies at predicted interfaces to best fit the SAXS profile of a complex from two known structures. In agreement with the long $D_{max}$, the top FoXSDock model of the ternary complex ($\chi=2.22$) placed CRY1 alongside the PAS-AB core, docked at the CLOCK PAS-B interface (FIG. 8, panels B and C). Importantly, each of the statistically degenerate top ensembles independently placed CRY1 at the CLOCK PAS-B interface. However, there was some ambiguity in the positioning of CRY1 using the SAXS data alone, as the experimental scattering profile was equally fit by several orientations of CRY1 bound to the HI loop protrusion in CLOCK PAS-B. Next examined was how well the HADDOCK model fit the data when aligned onto the bHLH PAS-AB dimer via the CLOCK PAS-B domain. As shown in FIG. 8 (panel B), both methods provided reasonable fits to the experimental data, as shown by the overlay of a representative model of HADDOCK (FoXSDock HADDOCK $\chi=2.74$, FIG. 9, panel D) with the best-scored SAXS-driven model (FoXSDock SAXS). Importantly, both of these models orient CRY1 such that its coiled-coil (CC) helix sits on the top of the ternary complex, available to make interactions with the BMAL1 TAD and other clock proteins that target this critical interface (FIG. 8, panel C). Therefore, the integration of biochemistry, SAXS and computational modeling provides the first low resolution models of the CRY1:CLOCK:BMAL1 ternary complex.

Figure 5:
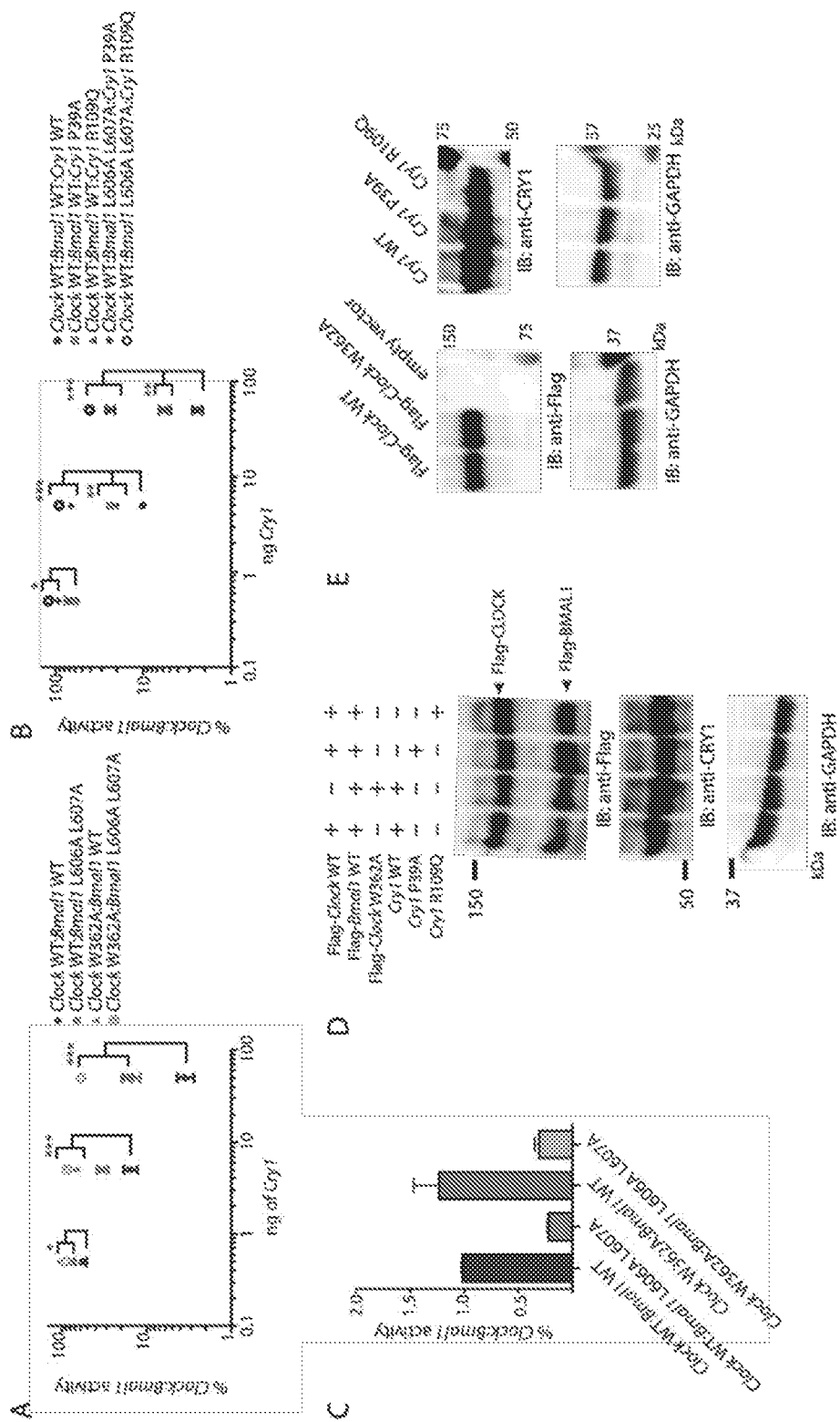
FIG. 5 depicts data demonstrating that point mutations in CLOCK PAS-B and CRY1 secondary pocket reduce repression of CLOCK:BMAL1 by CRY1. Panel A: Per1-Luc assay with increasing amounts of plasmids encoding Cry1 (0.5, 5 and 50 ng) with Clock WT or Clock W362A and Bmal1 WT or L606A L607A (100 ng each). Relative activity normalized to Clock:Bmal1 (WT or mut) without Cry1 co-transfected set to 100. Panel B: Per1-Luc assay with increasing amounts of Cry1 WT or point mutants (P39A and R109Q) with Clock WT and Bmal1 WT or L606A L607A. L606A and L607A mutations in the transactivation domain of Bmal1 reduce repression by Cry1 and synergistically reduce repression when paired with mutations in CLOCK PAS-B and the CRY1 secondary pocket. *P<0.05; P<0.01; *P<0.001 compared by two-tailed t-test. Panel C: Comparison of relative activity of Clock:Bmal1 constructs used in Per1-luciferase assay. The basal activity of the mutants are shown relative to wild-type Clock:Bmal1 activity set to 1.0. Panel D: HEK293T cells were transfected with plasmid ratios used in Per1-luciferase assay (100 ng each Flag-Clock and Flag-Bmal1, and Cry1 plasmid as indicated, scaled 4× for increase in culture dish area). Relative protein expression levels are shown by western blotting using indicated antibodies. GAPDH is shown as a loading control. Panel E: HEK293T cells were transfected with 1 µg of the indicated plasmid. Relative protein expression levels are shown by western blotting using indicated antibodies.
Figure 10:
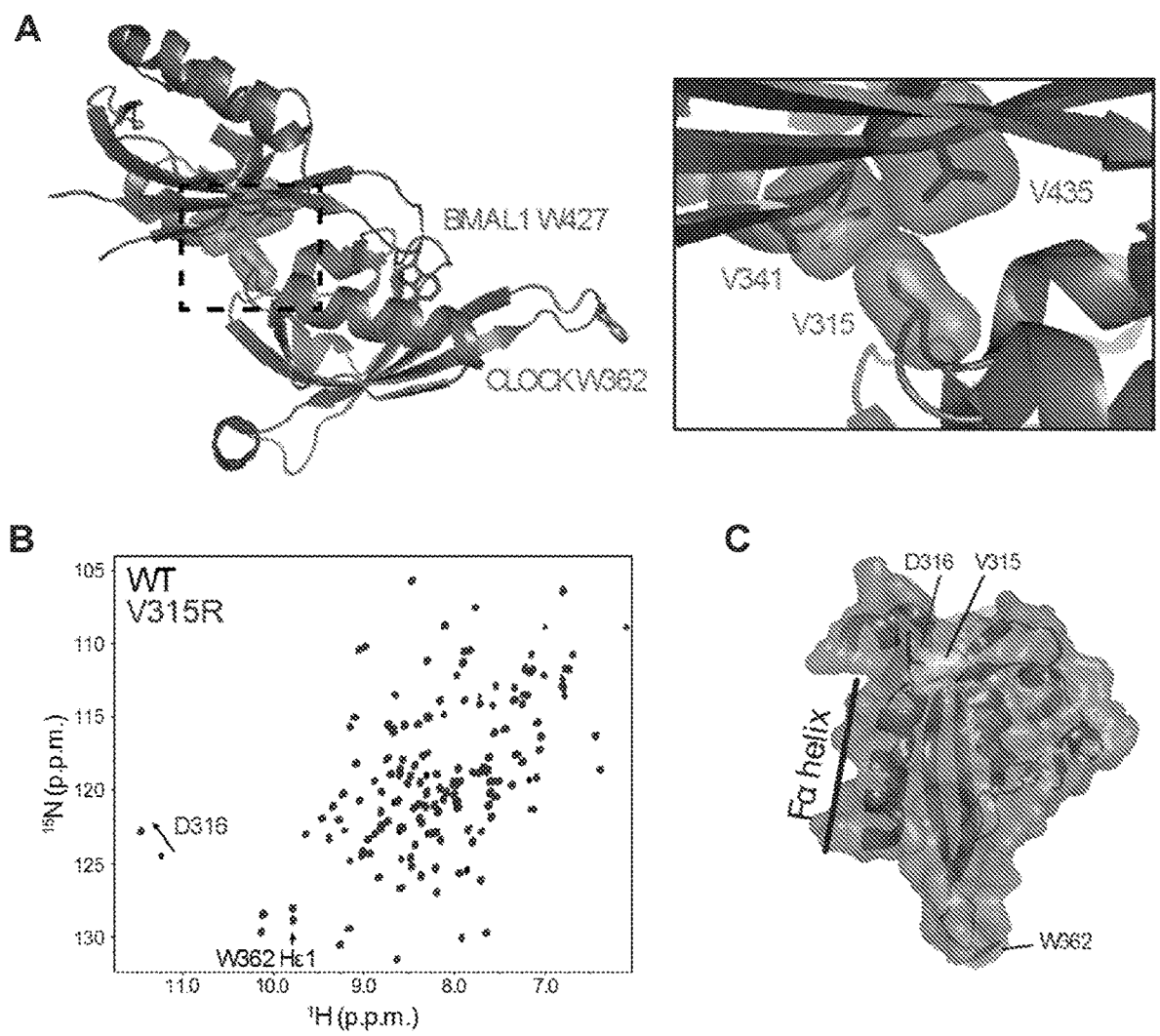
FIG. 10 provides data demonstrating that CLOCK PAS-B and BMAL1 PAS-B form a native dimer in solution. Panel A: Residue V315 in the Fα-helix of CLOCK PAS-B is at the native CLOCK:BMAL1 PAS-B interface in the bHLH-PAS-AB dimer structure (PDB: 4F3L). Introduction of a charge V315R is predicted to disrupt native PAS-B dimer formation. Panel B: 15N HSQC of CLOCK PAS-B WT and CLOCK PAS-B V315R mutant. Peaks are well-dispersed indicative of a well-folded PAS domain protein. D316 shows a minor shift as it is located in close proximity to the mutation (See panel C). Panel C: CLOCK PAS-B domain highlighting residues assigned in the 5N HSQC spectra in Panel B. Panel D: Superdex 75 10/300 GL analytical size exclusion analysis of BMAL1 PAS-B and CLOCK PAS-B heterodimerization. Co-elution and a shift in elution volume indicate PAS-B dimer formation. BMAL1 PAS-B alone UV trace is shown in yellow dash. CLOCK:BMAL1 PAS-B dimer trace is displayed. Peak fractions analyzed by SDS-PAGE gel electrophoresis. Panel E: CLOCK PAS-B V315R mutant no longer binds BMAL1 PAS-B. Size exclusion analysis on Superdex 75 10/300 GL of BMAL1 PAS-B and CLOCK PAS-B V315R no longer results in a gel shift or co-elution of the proteins. CLOCK PAS-B V315R incubated 1:1 with BMAL1 PAS-B is shown by the solid UV trace.
Figure 10:
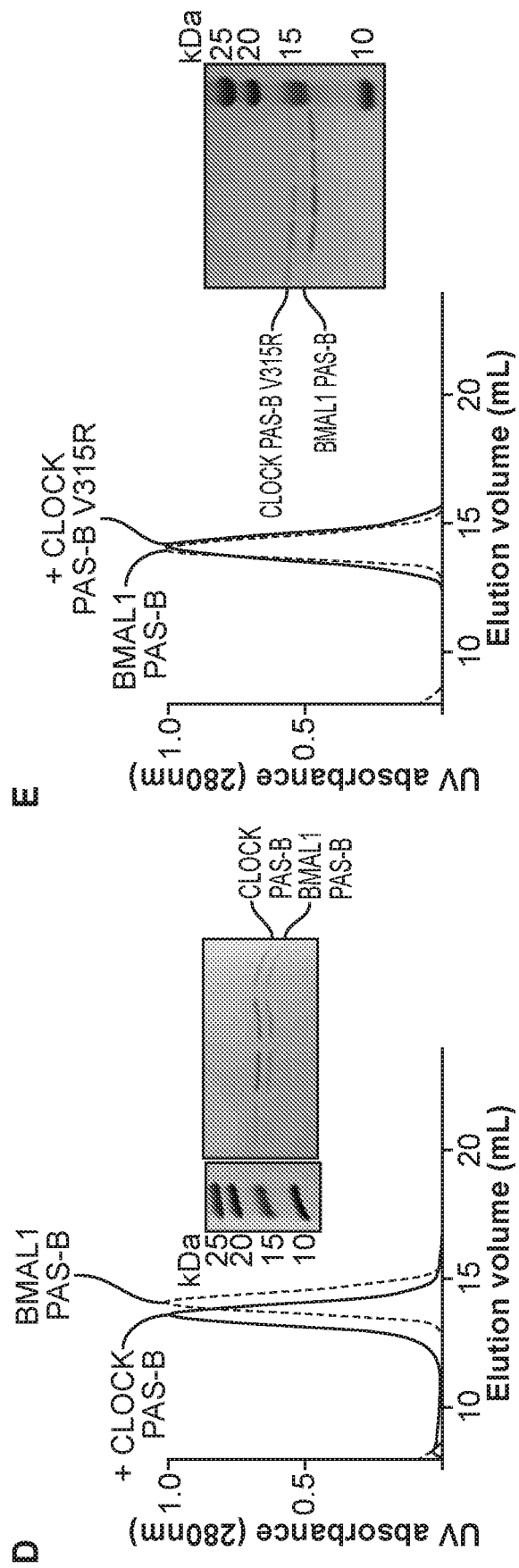

As with the above-described SAXS studies of the CLOCK:BMAL1 heterodimer, scattering data for the ternary complex were best fit by a model where the PAS-B domains of CLOCK and BMAL1 were no longer tightly bound to each other, with the heterodimer maintained by interactions between the N-terminal PAS-A domains (FIG. 2, panel C) and bHLH domains (FIG. 8, panel B). To test whether CRY1 binding influences the association of CLOCK and BMAL1 PAS-B domains with one another, binding assays using the heterodimer of isolated PAS-B domains were performed. The PAS-B domains of CLOCK and BMAL1 form a complex that co-migrates by size exclusion chromatography (FIG. 10). Using NMR and size exclusion chromatography, it was confirmed that the PAS-B domains maintain a parallel, stacked orientation in isolation similar to that observed in the bHLH PAS-AB structure (FIG. 10, panels A-E). Investigated next was whether binding of CRY1 would influence the interaction between CLOCK and BMAL1 PAS-B domains in the dimer. Size exclusion chromatography of CRY1 with a preformed CLOCK:BMAL1 PAS-B dimer demonstrated that binding of CLOCK PAS-B to CRY1 disrupted its interaction with BMAL1 PAS-B (FIG. 5, panels D and E). Altogether, these data indicate that CRY1 binding to CLOCK:BMAL1 may influence the architecture of the PAS domain core.

Materials and Methods for Examples 1-4

Protein Expression and Purification

Using the baculovirus expression system (Invitrogen), $His_6$-tagged mouse CRY1 PHR was expressed in Sf9 suspension insect cells (Expression Systems). $His_6$-tagged mouse CLOCK bHLH PAS-AB domains (residues 26-384) and native mouse BMAL1 bHLH PAS-AB (residues 68-453) were cloned into pFastBac HTb and pFastBac1 vectors, respectively. CLOCK PAS-B (residues 261-395), CLOCK PAS-AB (residues 93-395), and BMAL1 PAS-B (residues 329-441) were expressed in *E. coli* Rosetta2 (DE3) cells as a fusion to the solubilizing tags $His_6$-NusA or $His_6$-B1 domain of *Streptococcal* protein G (GB1).

For $His_6$-tagged mouse CRY1 PHR (amino acids 1-491) Sf9 suspension cells were infected with a P3 virus at $1.5 \times 10^6$ cells/mL and grown for 72 hours. Following brief centrifugation at 4K rpm, cells were resuspended in 50 mM Tris pH 7.5, 200 mM NaCl, 20 mM imidazole, 10% glycerol, 0.2% triton x-100, 0.1% NP40, 0.4% Tween-20, 5 mM 3-mercaptoethanol and EDTA-free protease inhibitors (Pierce). Cells were lysed using a microfluidizer followed by brief sonication for 15 sec. on/30 sec. off for 3 pulses at 40% amplitude. Lysate was clarified at 37K rpm, 4° C. for 1 hour. The protein was then isolated by $Ni^{2+}$-nitrilotriacetic acid affinity chromatography (QIAGEN) followed by ion exchange and size-exclusion chromatography. The protein was isolated by $Ni^{2+}$-nitrilotriacetic acid affinity chromatography (QIAGEN). The eluted protein was further purified by ion exchange and size-exclusion chromatography into 20 mM HEPES (pH 7.5), 125 mM NaCl, 5% glycerol and 2 mM TCEP.

Sf9 insect cells (Expression systems) co-expressing $His_6$ tagged mouse CLOCK and BMAL1 bHLH PAS-AB for 65 hours were lysed by sonication in lysis buffer containing 50 mM $Na_2HPO_4$ pH 8.0, 300 mM NaCl, 10% v/v glycerol, 15 mM imidazole, 2.5 mM CHAPS, 5 mM β-mercaptoethanol and EDTA-free protease inhibitors (Thermo). The clarified cell lysate was applied onto a Ni-NTA Agarose column (Qiagen) and bound protein was eluted with a gradient of 15 mM-500 mM imidazole. Pooled fractions were buffer exchanged into 20 mM Tris pH 8.0, 200 mM NaCl, 10% v/v glycerol, 1 mM DTT. His tag was removed by treatment with TEV Protease overnight at 4° C. The CLOCK:BMAL1 bHLH PAS-AB complex was further purified using a heparin column followed by a size exclusion chromatography into 20 mM HEPES pH 7.5, 300 mM NaCl, 5% v/v glycerol and 1 mM DTT.

For CLOCK PAS-B, CLOCK PAS-AB and BMAL1 PAS-B expressed in Rosetta (DE3) cells; protein expression was induced with 0.5 mM IPTG at an $OD_{600}$ of 0.8, and grown for an additional 16 h at 18° C. Soluble protein was purified by $Ni^{2+}$-nitrilotriacetic acid affinity chromatography (QIAGEN), followed by cleavage of the tag with $His_6$-TEV protease overnight at 4° C. Subsequent $Ni^{2+}$-nitrilotriacetic acid affinity chromatography was performed to remove the protease and cleaved tag. The protein was further purified by size-exclusion chromatography on a Superdex 75 16/60 prep grade column (GE Healthcare) equilibrated with 20 mM HEPES pH 7.5, 125 mM NaCl, 5% glycerol and 2 mM TCEP. Point mutations in CRY1 PHR, CLOCK PAS-B and CLOCK PAS-AB were introduced by site-directed mutagenesis and validated by sequencing.

BMAL1 PAS-AB (residues 136-441) was expressed in *E. coli* SoluBL21 cells as a fusion to the solubilizing tag Glutathione S-Transferase (GST). Protein was expressed via the method described above. Soluble protein was purified by GST affinity chromatography (GE Healthcare), followed by cleavage of the tag with $His_6$-TEV protease overnight at 4° C. Subsequent $Ni^{2+}$-nitrilotriacetic acid and GST affinity chromatography were performed to remove the protease and cleaved tag. The protein was further purified by size-exclusion chromatography as described above.

Analytical Size-Exclusion Chromatography

For analysis of complex formation by size-exclusion chromatography (SEC), purified proteins were injected on a Superdex 200 10/300 GL or Superdex 75 10/300 GL analytical column at 10-50 μM (~250 μL, 1:1 molar ratio) in 20 mM HEPES pH 7.5, 125 mM NaCl, 5% glycerol and 2 mM TCEP. Proteins were incubated for ~30 min. or overnight and analyzed by SEC. All size-exclusion columns were calibrated with a low-molecular-weight gel filtration standards kit (GE Healthcare Life Sciences). The content of each peak was evaluated by SDS-PAGE and Coomassie staining.

Transcriptional Reporter Assays and Western Blotting

Per1-Luc reporter gene assays investigating repression by CRY1 were performed as described in Xu et al. (2015) *Nat Struct Mol Biol* 22(6):476-484. Briefly, the following plasmids were transfected in duplicate into HEK293T cells in a 48-well plate using LT-1 transfection reagent (Mirus): 5 ng pGL3 Per1-Luc reporter, 100 ng each pSG5 mouse Flag-Bmal1 and pSG5 mouse $His_6$Flag-Clock, and pcDNA3 mouse Cry1 (untagged) in increasing amounts as indicated; empty pcDNA4 vector was used to normalize total plasmid levels to 800 ng DNA/well. Cells were harvested 30 hours after transfection using Passive Lysis Buffer (NEB) and luciferase activity assayed using Bright-Glo luciferin reagent (Promega). Each reporter assay was repeated three independent times. To compare expression of Flag-tagged Clock, Bmal1 and untagged Cry1 genes, cells were lysed in 50 mM HEPES pH 7.5, 150 mM NaCl, 1 mM EDTA, 5% glycerol and 1% Triton X-100. Immunoblotting was done with the HRP-conjugated rabbit polyclonal OctA-Probe antibody (D-8) (Santa Cruz Biotechnology cat. no. sc-807), rabbit polyclonal anti-CRY1 (H-84) (Santa Cruz Biotechnology cat. no. sc-33177) or mouse monoclonal GAPDH (G-9) (Santa Cruz Biotechnology, sc-365-062). HRP-conjugated secondary antibodies were used at 1:10,000 (Santa Cruz Biotechnology) in TBST. Western signal was detected using Clarity ECL reagent (Bio-Rad) and visualized on a ChemiDoc XRS+ imager (Bio-Rad).

HADDOCK Modeling

The CLOCK PAS-B molecule (residues 261-384) used in the modeling was generated from the CLOCK:BMAL1 bHLH-PAS-AB structure (PDB:4F3L). The CRY1 input molecule used was the inventors' 1.8 Å resolution structure (PDB: 5T5X). After generating the protein components; the structures were docked as a complex using the HADDOCK 2.2 server (22). The protocol for docking and refinement was executed using the default parameter sets on the server and defining passive residues automatically around the active residues.

GST Pulldown Assays

GST CLOCK PAS-B and GST BMAL1 PAS-AB were expressed in *E. coli* as described above. Soluble proteins were purified using GS4B resin (GE Healthcare). GST-tagged proteins were eluted with 10 mM glutathione and peak elution was desalted into 20 mM HEPES pH 7.5, 125 mM NaCl, 5% glycerol and 2 mM TCEP. GST pulldowns contained 1 μM GST-tagged protein (bait) and 5 μM CRY1 (prey) and ~10 μL glutathione agarose in a 200 μL reaction volume. After rotation at 4° C. overnight, reactions were washed 3 times with the above buffer and eluted with 6×SDS. Samples were boiled for ~5 min. and loaded on an SDS-PAGE gel for visualization by Coomassie stain.

Small Angle X-Ray Scattering (SAXS)

SAXS data were collected on the SIBYLS beamline (12.3.1) at the Advanced Light Source (Lawrence Berkeley National Laboratory). Multiple exposures of three concentrations (1, 3, and 5 mg/mL) of freshly purified protein were taken to check for concentration dependence of scattering and radiation damage (neither was detected). Briefly, data were merged using PRIMUS, and the radius of gyration was determined using the Guinier approximation. The pair-distance distribution function [P(r)] and maximal particle size ($D_{max}$) were generated in GNOM, and the output data were used by GASBOR to calculate 10 independent solution envelopes that were averaged together using DAMAVER. The improved model of the solution structure was used in UCSF Chimera to fit into the averaged solution envelope.

SAXS modeling was performed using a combination of programs: FoXS, MultiFoXS and FoXSDock. Conformational sampling of the CLOCK:BMAL1 bHLH PAS-AB was done by MultiFoXS starting from the crystal structure (PDB: 4F3L) with missing fragments built by MODELLER. HingeProt was used to determine the hinge regions within the CLOCK:BMAL1 heterodimer with PDB: 4F3L as the input. The input to FoXSDock was the HADDOCK active residues as the binding site and (FIG. 3) the SAXS profile of the CRY1:CLOCK:BMAL1 bHLH PAS-AB complex. The entire sequences of CRY1 and CLOCK:BMAL1 bHLH PAS-AB subject to crystallography and SAXS, including vector artifacts after TEV cleavage, were used in the modeling.

X-Ray Crystallography

CRY1 protein was purified as described above. The protein was concentrated to 5 mg/mL and crystallized by hanging-drop vapor diffusion at 22° C. Crystals formed in a 1:1 ratio of protein to precipitant in 0.1 M MES pH 6.8, 10 mM EDTA, 15% (vol/vol) PEG3350. Crystals were frozen in the proper well buffer with 20% (vol/vol) PEG400 as a cryoprotectant. Data were collected at the Advanced Light Source, Lawrence Berkeley National Laboratory at Beamline (BL5.0.1). Diffraction spots were integrated using MOSFLM, and data were merged and scaled using Scala. Phases were first solved for by molecular replacement with a previous apo CRY1 structure (PDB: 4K0R) using Phaser. The structure was built with Coot and refined with PHENIX. Coordinates and structure factors have been deposited in PDB (PDB ID: 5T5X).

Nuclear Magnetic Resonance (NMR)

NMR experiments were conducted at 25° C. on a Varian INOVA 600-MHz spectrometer equipped with $^1H$, $^{13}C$, $^{15}N$ triple resonance, Z-axis pulsed field gradient probes. All NMR data were processed using NMRPipe/NMRDraw. Chemical shift assignments were made by mutation and by analogy to a far downfield-shifted peak found in all PAS domain HSQC spectra for the residue that sits at the top of the helical dipole for the Fα helix (D316 in CLOCK PAS-B). $^1H$-$^{15}N$ HSQC spectra were collected on 100 μM $^{15}N$ CLOCK PAS-B WT or V315R mutant in 50 mM Tris, pH 7.5, 50 mM NaCl, 2 mM TCEP, 10% (vol/vol) $D_2O$. HSQC data were visualized with NMRViewJ.

Example 5—Identification of Agents that Disrupt the CRY1-CLOCK-BMAL1 Ternary Complex As demonstrated above, the inventors have determined that disrupting the interaction between the secondary pocket of the photolyase homology region (PHR) of CRY1 and the CLOCK PAS-B domain is unexpectedly sufficient to disrupt the CRY1-CLOCK-BMAL1 ternary complex. In view of this finding, agents that bind the deep (and therefore highly "druggable") secondary pocket of CRY1 and inhibit interaction between the secondary pocket and the CLOCK PAS-B domain will be effective in disrupting and preventing the formation of the CRY1-CLOCK-BMAL1 ternary complex, and in turn, will be capable of resetting the circadian clock or shortening circadian period, e.g., in an individual having Delayed Sleep Phase Syndrome (DSPS).

In this example, a fluorescence polarization (FP) assay is used to screen a library of agents (e.g., a small molecule library, a library of peptides, and/or the like) for agents that inhibit interaction between the CRY1 PHR (e.g., the secondary pocket) and the CLOCK PAS-B domain. Such agents include those that bind the secondary pocket of the CRY1 PHR.

Figure 11:
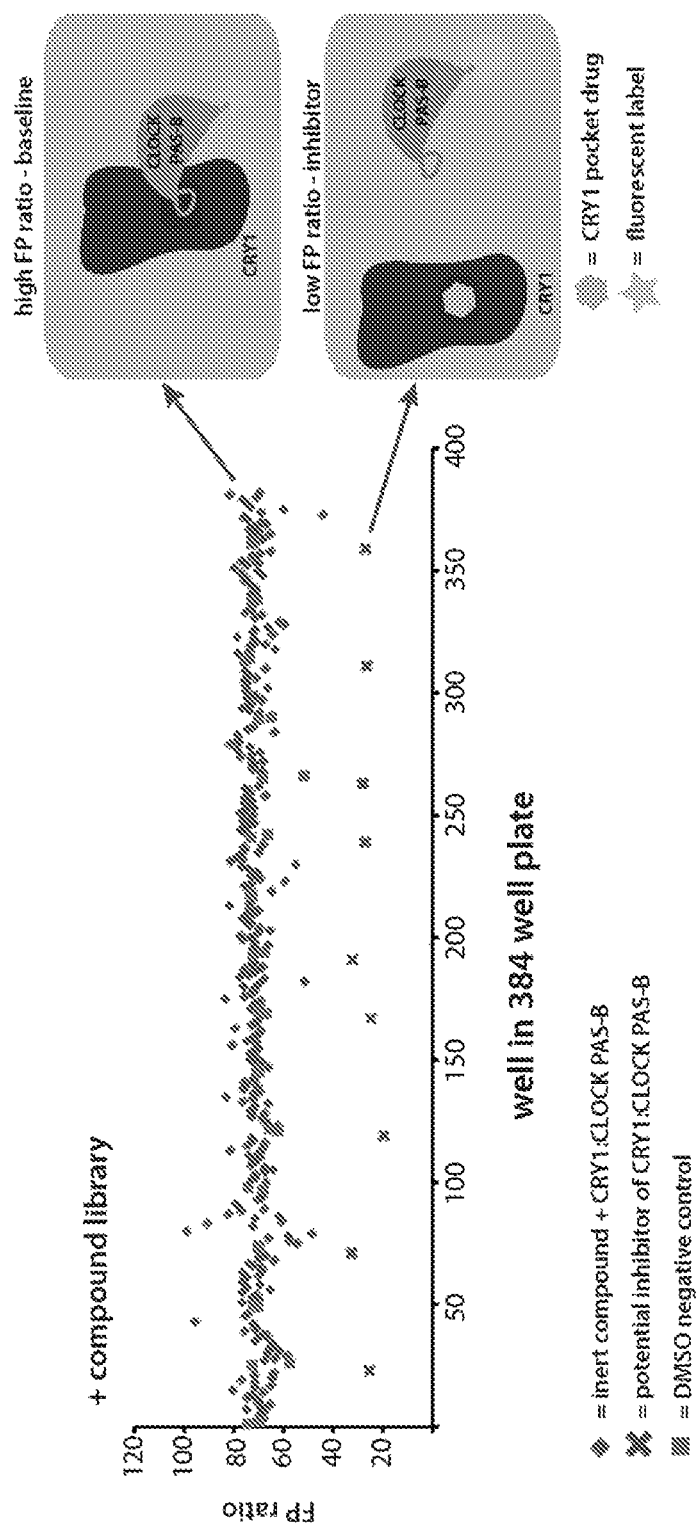
FIG. 11 schematically illustrates an example approach for identifying agents that disrupt the CRY1-CLOCK-BMAL1 ternary complex according to one embodiment of the present disclosure.

The screening approach of this example is schematically illustrated in FIG. 11. Recombinantly expressed CLOCK PAS-B domain is covalently labeled with a fluorescent tag and then incubated with purified CRY1 (residues 1-491 of the photolyase homology region (PHR)) at a concentration just above the equilibrium dissociation constant ($K_d$) to ensure complex formation. Complexes are plated, e.g., in a 384-well format opaque plate, after which compound libraries will then be pinned into the plate alongside negative controls (e.g., DMSO negative controls). Both the total fluorescence and fluorescence polarization are measured to calculate the overall FP ratio.

Compounds that produce a significantly lower FP ratio compared to controls in the initial screen may be subjected to a dose-response to obtain an approximate $K_I$ for the disruption of the complex. Compounds that pass this test (reproducibility and dose dependence outside of the screening format) may be further investigated for activity as CRY1 secondary pocket drugs that inhibit formation of the CRY1: CLOCK PAS-B complex, and by extension, the CRY1: CLOCK:BMAL1 ternary complex. Such an agent/drug could be used as a circadian-targeted therapeutic to "reset" the transcription-translation feedback loop of the clock or alter the interaction of CRY1 with CLOCK:BMAL1 to change circadian period. By directly targeting the CLOCK-binding secondary pocket of CRY1, the mechanism of action of such agents/drugs is much more rapid and focused compared to kinase inhibitors that have previously been proposed to elicit similar effects.

Approaches for producing example CRY1 and CLOCK PAS-B proteins that find use in the identification of agents that disrupt the CRY1-CLOCK-BMAL1 ternary complex, as well as an example screening assay and positive control that may be employed, are described in the following examples.

Example 6—Expression and Purification of His-CRY1 PHR

Described in this example is the expression and purification of a $His_6$-tagged CRY1 protein that includes a CRY1 photolyase homology region (PHR) consisting of residues 1-491 of the human CRY1 protein.

In this example, Sf9 cells were infected with amplified P3 virus encoding a $His_6$-tagged CRY1 PHR (~55 kDa). After incubation with gentle shaking at 27° C. for 72 hours for protein expression, the $His_6$-tagged CRY1 PHR was purified by lysing the cells and performing Ni affinity chromatography by fast protein liquid chromatography (FPLC) using a 5 mL His-Trap XL column. The $His_6$ tag was cleaved from the CRY1 PHR using $His_6$-TEV protease. The CRY1 PHR amino acid sequence and the amino acid sequence of the post-cleavage CRY1 PHR (with residual vector sequence underlined) are provided in Table 3.

TABLE 3

CRY1 PHR Amino Acid Sequences

| | |
|---|---|
| CRY1 PHR amino acid sequence (residues 1-491) (SEQ ID NO: 7) | MGVNAVHWFRKGLRLHDNPALKECIQGADTIRCVYILDPWFAGSSNV GINRWRFLLQCLEDLDANLRKLNSRLFVIRGQPADVFPRLFKEWNITK LSIEYDSEPFGKERDAAIKKLATEAGVEVIVRISHTLYDLDKIIELNGGQ PPLTYKRFQTLVSKMEPLEMPADTITSDVIGKCMTPLSDDHDEKYGV PSLEELGFDTDGLSSAVWPGGETEALTRLERHLERKAWVANFERPR MNANSLLASPTGLSPYLRFGCLSCRLFYFKLTDLYKKVKKNSSPPLSL YGOLLWREFFYTAATNNPRFDKMEGNPICVQ1PWDKNPEALAKWAE GRTGFPWIDAIMTQLRQEGWIHHLARHAVACFLTRGDLWISWEEGM KVFEELLLDADWSINAGSWMWLSCSSFFQQFFHCYCPVGFGRRTDP NGDYIRRYLPVLRGFPAKYIYDPWNAPEGIQKVAKCLIGVNYPKPMV NHAEASRLNIERMKQIYQQL |
| CRY1 PHR-final amino acid sequence with vector sequence underlined (SEQ ID NO: 8) | <u>GAMDPEF</u>MGVNAVHWFRKGLRLHDNPALKECIQGADTIRCVYILDP WFAGSSNVGINRWRFLLQCLEDLDANLRKLNSRLFVIRGQPADVFPR LFKEWNITKLSIEYDSEPFGKERDAAIKKLATEAGVEVIVRISHTLYDLD KIIELNGGQPPLTYKRFQTLVSKMEPLEMPADTITSDVIGKCMTPLSD DHDEKYGVPSLEELGFDTDGLSSAVWPGGETEALTRLERHLERKAW VANFERPRMNANSLLASPTGLSPYLRFGCLSCRLFYFKLTDLYKKVK KNSSPPLSLYGOLLWREFFYTAATNNPRFDKMEGNPICVQIPWDKNP EALAKWAEGRTGFPWIDAIMTQLRQEGWIHHLARHAVACFLTRGDL WISWEEGMKVFEELLLDADWSINAGSWMWLSCSSFFQQFFHCYCP VGFGRRTDPNGDYIRRYLPVLRGFPAKYIYDPWNAPEGIQKVAKCLI GVNYPKPMVNHAEASRLNIERMKQIYQQL |

Example 7—Expression and Purification of CLOCK PAS-B

Described in this example is the expression and purification of a CLOCK PAS-B fusion protein that includes a cleavable $His_6$NusA purification tag consisting of a $His_6$ tag, linker, NusA protein and TEV protease cleavage site fused upstream of a CLOCK PAS-B domain consisting of residues 261-395 of the human CLOCK protein.

In this example, for expression of the fusion protein, Rosetta2 (DE3) cells were transformed with a plasmid encoding the fusion protein. Clarified lysate from the cells was combined with Ni-NTA resin, which was thoroughly washed. The tag was cleaved from the CLOCK PAS-B domain on-column using $His_6$-TEV protease (1 mg protease for each ~30 mg of target protein overnight at 4° C.). Following cleavage, the resin slurry was transferred back to a gravity column and the flow through was collected. Pooled fractions were concentrated for size exclusion chromatography, which was subsequently performed using a Superdex 75 16/60 prep column. CLOCK PAS-B was then concentrated using an Amicon Ultra centrifugal concentrator with a 10 kDa molecular weight cutoff.

Amino acid sequences of the $His_6$-NusA-TEV fusion protein tag (TEV recognition sequence in bold), the CLOCK PAS-B domain, and the final CLOCK PAS-B protein sequence after purification (with residual vector sequence underlined), are provided in Table 4.

TABLE 4

Purification Tag and CLOCK PAS-B Amino Acid Sequences

| | |
|---|---|
| $His_6$NusA-XL Fusion Protein Tag amino acid sequence (SEQ ID NO: 9) | MGSSHHHHHHGSSGSSGHHHGSSGSSGSSMNKEILAVVEAVSNEKA LPREKIFEALESALATATKKKYEQEIDVRVQIDRKSGDFDTFRRWLVVD EVTQPTKEITLEAARYEDESLNLGDYVEDQIESVTFDRITTQTAKQVIV QKVREAERAMVVDQFREHEGEIITGVVKKVNRDNISLDLGNNAEAVIL REDMLPRENFRPGDRVRGVLYSVRPEARGAQLFVTRSKPEMLIELFRI EVPEIGEEVIEIKAAARDPGSRAKIAVKTNDKRIDPVGACVGMRGARV QAVSTELGGERIDIVLWDDNPAQFVINAMAPADVASIVVDEDKHTMDIA VEAGNLAQAIGRNGQNVRLASQLSGWELNVMTVDDLQAKHQAEAHA AIDTFTKYLDIDEDFATVLVEEGFSTLEELAYVPMKELLEIEGLDEPTVE ALRERAKNALATIAQAQEESLGDNKPADDLLNLEGVDRDLAFKLAARG VCTLEDLAEQGIDDLADIEGLTDEKAGALIMAARNICWFGDEAGIEENL YFQGAMDPEF |
| CLOCK PAS-B amino acid sequence (residues 261-395) (SEQ ID NO: 10) | QFIKEMCTVEEPNEEFTSRHSLEWKFLFLDHRAPPIIGYLPFEVLGTSG YDYYHVDDLENLAKCHEHLMQYGKGKSCYYRFLTKGQQWIWLQTHY YITYHQWNSRPEFIVCTHTVVSYAEVRAERRRELGIEESL |
| CLOCK PAS-B-final amino acid sequence after purification with vector sequence underlined (SEQ ID NO: 11) | <u>GAMDPEF</u>QFIKEMCTVEEPNEEFTSRHSLEWKFLFLDHRAPPIIGYLPF EVLGTSGYDYYHVDDLENLAKCHEHLMQYGKGKSCYYRFLTKGQQW IWLQTHYYITYHQWNSRPEFIVCIHTVVSYAEVRAERRRELGIEESL |

Example 8—Site-Specific Fluorescent Labeling of CLOCK PAS-B

Described in this example is the labeling of a CLOCK PAS-B domain prepared according to method described in Example 7. In this particular example, the CLOCK PAS-B domain was site-specifically labeled with FAM (fluorescein) at its N-terminus using Sortase A.

The CLOCK PAS-B domain was buffer exchanged into Sortase Buffer. Labeling was carried out using a labeling reaction that included the CLOCK PAS-B domain with N-terminal glycine, $CaCl_2$, purified $His_6$-Sortase A, and FAM-LPETGG, incubated at 4° C. overnight. The enzyme was removed using a His-Trap Excel column. Analytical scale size exclusion chromatography was carried out to further purify the labeled CLOCK PAS-B domain. The purified labeled CLOCK PAS-B domain was flash frozen in liquid nitrogen for storage at −80° C. The inventors have determined that more than one freeze/thaw cycle of CLOCK PAS-B should not be carried out, nor should the protein be stored on ice at 4° C. longer than a day or soluble aggregates will form.

Example 9—Displacement Assay of Labeled CLOCK PAS-B from CRY1 PHR

Described in this example is a fluorescence polarization (FP)-based displacement assay developed by the inventors for identifying agents that disrupt the CRY1-CLOCK-BMAL1 ternary complex.

CRY1 PHR and CLOCK PAS-B domain fluorescently labeled at its N-terminus were prepared as described in the preceding examples. Equipment/Reagents included the following: Greiner 384 Well Assay Plate, 120 µl rounded square wells, flat bottom, black polystyrene; Envision 2103 Multilabel Reader (2103-0020); Fluorescence Polarization (FP) assay buffer (50 mM Bis-Tris Propane, 100 mM NaCl, 2 mM TCEP, 0.05% Tween-20, 0.5% DMSO, pH 7.5); and GraphPad Prism (version 6 or higher). All assay components were buffer exchanged into FP buffer.

A stock assay mixture of 8 µM CRY1 and 40 nM labeled CLOCK PAS-B was incubated at 4° C. overnight. Equal volumes (half of final well volume) stock assay mixture was dispensed into wells of the Greiner 384 Well Assay Plate, reserving wells for appropriate controls. Equal volumes (half of final well volume) of the test agent was dispensed into wells of the assay plate. Fluorescence polarization was measured using an Envision 2013 plate reader.

A labeled CLOCK PAS-B-only control of 20 nM was used to determine the G-factor for FP. The G-factor should be variable "G" such that Fluorescence polarization (FP) =1000*(S−G*P)/(S+G*P). For labeled CLOCK PAS-B-only control, FP=27 mP. G=(S/P)*(1−27/1000)/(1+27/1000), with S being the parallel fluorescence intensity, and P being the perpendicular fluorescence intensity. The constant of 27 mP is reflective of the literature value of FP for FITC. The unit mP is a dimensionless unit that is an abbreviation of "milli-Polarization." FP values are collected for each well.

Example 10—Positive Control for Displacement Assay of Labeled CLOCK PAS-B from CRY1 PHR A dominant mutation in CRY1 which induces alternate splicing and exclusion of CRY1 Exon 11 was recently discovered in humans having a longer circadian period. Patke et al. (2017) *Cell* 169:203-215. The longer circadian period leads to the delayed rise melatonin at night and a late onset for sleep (bedtimes ~2-3 am). This meets clinical criteria for Delayed Sleep Phase Syndrome (DSPS) and has severe consequences for overall sleep quality and duration, as well as other co-morbidities such as depression.

The present inventors have determined how this mutation exerts biochemical control of CRY1 interactions with CLOCK:BMAL1. In summary, the ~25 residue peptide encoded by the 11th exon of CRY1 acts as an auto-inhibitory module to antagonize the interaction of CRY1 with CLOCK PAS-B.

Figure 12:
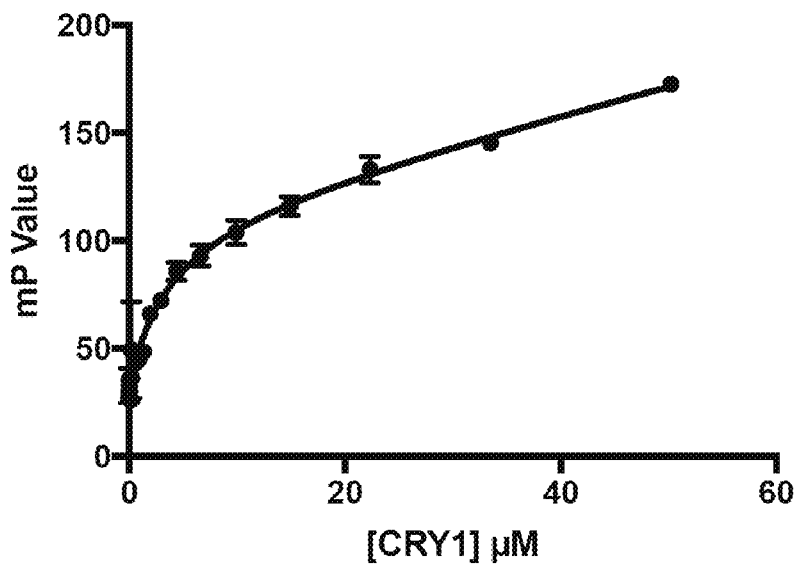
FIG. 12 shows binding of CLOCK PAS-B to CRY1 PHR under screening assay conditions according to one embodiment of the present disclosure.

The inventors investigated whether the peptide encoded by human CRY1 Exon 11 could serve as a positive control inhibitor of the CRY1-CLOCK PAS-B domain complex. Using the assay conditions described in Example 9, negative and positive controls were carried out. For the negative control, DMSO only was added to triplicate wells that included 20 nM CLOCK PAS-B probe and 4 µM CRY1 PHR. In the negative control, binding of the CRY1 PHR to CLOCK PAS-B was observed, as shown in FIG. 12. For the positive control, 100 µM of the peptide encoded by CRY1 Exon 11 was added to triplicate wells that included 20 nM CLOCK PAS-B probe and 4 µM CRY1 PHR. The amino acid sequence of the peptide encoded by human CRY1 Exon 11 is provided in Table 5.

TABLE 5

| Human CRY1 Exon 11-Encoded Amino Acid Sequence | |
| --- | --- |
| Human CRY1 Exon 11-encoded peptide amino acid sequence (residues 530-552) (SEQ ID NO: 12) | CSQGSG1LHYAHGDSQQTHLLK |

Figure 13:
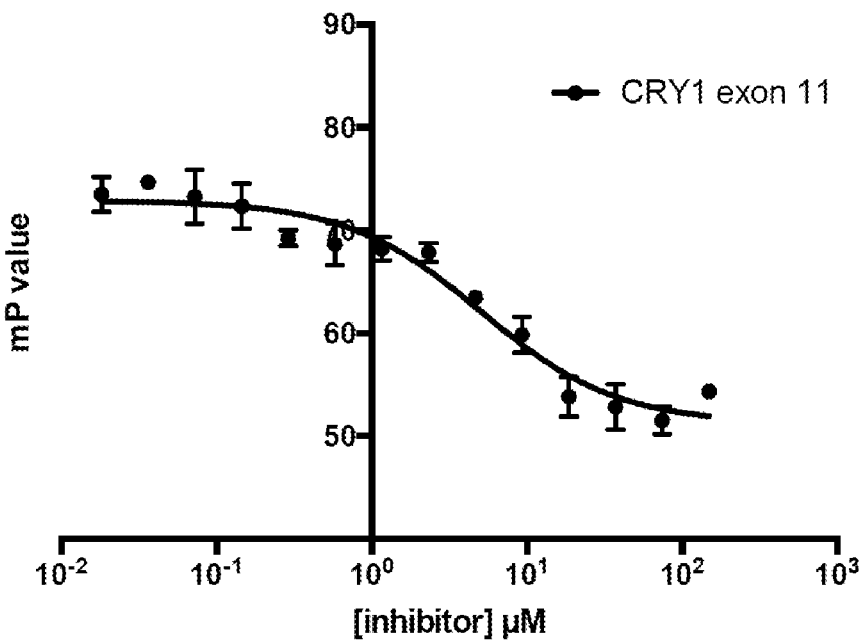
FIG. 13 shows displacement of CLOCK PAS-B from CRY1 PHR using a peptide encoded by CRY1 Exon 11 under screening assay conditions according to one embodiment of the present disclosure.

As shown in FIG. 13, the peptide encoded by CRY1 Exon 11 displaced CLOCK PAS-B from the CRY1 PHR, demonstrating the feasibility of the FP-based displacement assay developed by the inventors, as well as the utility of the peptide encoded by CRY1 Exon 11 as a positive control inhibitor in such assays.

Notwithstanding the appended claims, the disclosure is also defined by the following clauses:

1. A method for identifying an agent that disrupts a ternary complex including Cryptochrome-1 (CRY1), CLOCK, and BMAL1, the method including:
   combining:
   a CRY1 protein including the CRY1 photolyase homology region (PHR),
   a CLOCK PAS-B domain, and
   a test agent,
   under conditions suitable for CRY1-CLOCK PAS-B domain complex formation; and
   assessing CRY1-CLOCK PAS-B domain complex formation,
   wherein inhibition of CRY1-CLOCK PAS-B domain complex formation identifies the test agent as an agent that disrupts a ternary complex including CRY1, CLOCK, and BMAL1.

2. The method according to Clause 1, wherein the combining includes combining the CRY1 protein with the CLOCK PAS-B domain to form CRY1-CLOCK PAS-B domain complexes in the absence of the test agent, and subsequently combining the test agent and the CRY1-CLOCK PAS-B domain complexes.

3. The method according to Clause 1, wherein the combining includes combining the CRY1 protein with the test agent, and subsequently combining the CLOCK PAS-B domain with the CRY1 protein and test agent.

4. The method according to any one of Clauses 1 to 3, wherein the assessing is by fluorescence polarization (FP) assay, surface plasmon resonance (SPR), size exclusion chromatography coupled to multi-angle light scattering (SEC-MALS), nuclear magnetic resonance (NMR) spectroscopy, flow cytometry, or any combination thereof.

5. The method according to Clause 4, wherein the assessing is by fluorescence polarization (FP) assay.

6. The method according to Clause 5, wherein the CLOCK PAS-B domain is fluorescently-labeled.

7. The method according to Clause 6, wherein the CLOCK PAS-B domain is site-specifically fluorescently-labeled.

8. The method according to Clause 7, wherein the CLOCK PAS-B domain is site-specifically fluorescently-labeled at an internal site of the CLOCK PAS-B domain.

9. The method according to Clause 7, wherein the CLOCK PAS-B domain is site-specifically fluorescently-labeled at a terminus of the CLOCK PAS-B domain.

10. The method according to Clause 9, wherein the terminus is the N-terminus of the CLOCK PAS-B domain.

11. The method according to any one of Clauses 6 to 10, including site-specifically labeling the CLOCK PAS-B domain using Sortase A.

12. The method according to any one of Clauses 6 to 11, wherein the CLOCK PAS-B domain includes a Tetramethylrhodamine (TAMRA) fluorescent label or a Fluorescein amidite (FAM) fluorescent label.

13. The method according to any one of Clause 5 to 12, wherein the assessing includes measuring fluorescence polarization and total fluorescence, and calculating the ratio of fluorescence polarization to total fluorescence, wherein an FP ratio below a cut-off ratio identifies the test agent as an agent that disrupts a ternary complex including CRY1, CLOCK, and BMAL1.

14. The method according to any one of Clauses 1 to 13, wherein the test agent is a small molecule.

15. The method according to Clause 14, wherein the test agent includes a flavin moiety.

16. The method according to Clause 14, wherein the test agent is a folate derivative.

17. The method according to any one of Clauses 1 to 13, wherein the test agent is a polymer.

18. The method according to Clause 17, wherein the polymer is a peptide or polypeptide.

19. The method according to any one of Clauses 1 to 18, wherein the method further includes:
combining:
a CRY1 protein including the CRY1 photolyase homology region (PHR),
a CLOCK PAS-B domain, and
a positive control agent,
under conditions suitable for CRY1-CLOCK PAS-B domain complex formation,
wherein the positive control agent inhibits CRY1-CLOCK PAS-B domain complex formation.

20. The method according to Clause 19, wherein the positive control agent is a peptide encoded by Exon 11 of CRY1.

21. A CRY1:CLOCK:BMAL1 complex-disrupting agent that binds to the secondary pocket of CRY1 and inhibits interaction between the secondary pocket and the CLOCK PAS-B domain.

22. The CRY1:CLOCK:BMAL1 complex-disrupting agent of Clause 21, wherein the agent includes a flavin moiety.

23. The CRY1:CLOCK:BMAL1 complex-disrupting agent of Clause 21, wherein the agent is a folate derivative.

24. The CRY1:CLOCK:BMAL1 complex-disrupting agent of Clause 21, wherein the agent includes a CLOCK PAS-B domain or variant thereof.

25. The CRY1:CLOCK:BMAL1 complex-disrupting agent of Clause 21, wherein the agent consists of a CLOCK PAS-B domain or variant thereof.

26. The CRY1:CLOCK:BMAL1 complex-disrupting agent of any one of Clauses 21 to 25, wherein the agent was identified as a CRY1:CLOCK:BMAL1 complex-disrupting agent by the method according to any one of Clauses 1 to 18.

27. A pharmaceutical composition including:
the CRY1:CLOCK:BMAL1 complex-disrupting agent of any one of Clauses 21 to 26; and
a pharmaceutically acceptable carrier.

28. The pharmaceutical composition of Clause 27, wherein the composition is formulated for oral, parenteral, intravenous, intraperitoneal, intramuscular, topical, transdermal, subcutaneous, intranasal, mucosal, or sublingual administration.

29. A method for disrupting a CRY1:CLOCK:BMAL1 complex, including contacting the CRY1:CLOCK:BMAL1 complex with the CRY1:CLOCK:BMAL1 complex-disrupting agent of any one of Clauses 21 to 26.

30. The method of Clause 29, wherein the method is in vitro.

31. The method of Clause 29, wherein the method is in vivo.

32. A method including administering to an individual in need thereof a therapeutically effective amount of the CRY1:CLOCK:BMAL1 complex-disrupting agent of any one of Clauses 21 to 26 or the pharmaceutical composition of Clause 27 or Clause 28.

33. The method according to Clause 32, wherein the individual in need thereof has a circadian rhythm disorder.

34. The method according to Clause 33, wherein the circadian rhythm disorder is selected from the group consisting of: shift-work sleep disorder, jet lag, metabolic imbalance, delayed sleep phase syndrome (DSPS), advanced sleep phase syndrome (ASPS), non-24-hour sleep-wake syndrome, and irregular sleep-wake rhythm.

35. The method according to any one of Clauses 32 to 34, wherein the administering includes administration by oral, parenteral, intravenous, intraperitoneal, intramuscular, topical, transdermal, subcutaneous, intranasal, mucosal, or sublingual administration, or any combination thereof.

36. A kit, including:
a CRY1 protein including the CRY1 photolyase homology region (PHR), a CLOCK PAS-B domain, or both; and
instructions for using the CRY1 protein, the CLOCK PAS-B domain, or both, in a screening assay for identifying an agent that disrupts a ternary complex including CRY1, CLOCK, and BMAL1.

37. The kit of Clause 36, including a CRY1 protein including the CRY1 PHR, and a CLOCK PAS-B domain.

38. The kit of Clause 36 or 37, wherein the CLOCK PAS-B domain is labeled.

39. The kit of Clause 38, wherein the CLOCK PAS-B domain is site-specifically labeled.

40. The kit of Clause 39, wherein the CLOCK PAS-B domain is site-specifically labeled at a terminus of the CLOCK PAS-B domain.

41. The kit of Clause 40, wherein the terminus is the N-terminus of the CLOCK PAS-B domain.

42. The kit of any one of Clauses 36 to 41, wherein the CLOCK PAS-B domain is labeled with a fluorescent label.

43. The kit of Clause 42, wherein the fluorescent label is a Tetramethylrhodamine (TAMRA) fluorescent label or a Fluorescein amidite (FAM) fluorescent label.

44. The kit of any one of Clauses 36 to 43, further including a positive control agent.

45. The kit of Clause 44, wherein the positive control agent is a peptide encoded by Exon 11 of CRY1.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for identifying an agent that disrupts a ternary complex comprising Cryptochrome-1 (CRY1), CLOCK, and BMAL1, the method comprising:
combining:
a CRY1 protein comprising the CRY1 photolyase homology region (PHR),
a fluorescently-labeled CLOCK PAS-B domain, and
a test agent,
under conditions suitable for CRY1-CLOCK PAS-B domain complex formation; and
assessing CRY1-CLOCK PAS-B domain complex formation,
wherein inhibition of CRY1-CLOCK PAS-B domain complex formation identifies the test agent as an agent that disrupts a ternary complex comprising CRY1, CLOCK, and BMAL1.

2. The method according to claim 1, wherein the combining comprises combining the CRY1 protein with the CLOCK PAS-B domain to form CRY1-CLOCK PAS-B domain complexes in the absence of the test agent, and subsequently combining the test agent and the CRY1-CLOCK PAS-B domain complexes.

3. The method according to claim 1, wherein the combining comprises combining the CRY1 protein with the test agent, and subsequently combining the CLOCK PAS-B domain with the CRY1 protein and test agent.

4. The method according to claim 1, wherein the assessing is by fluorescence polarization (FP) assay, surface plasmon resonance (SPR), size exclusion chromatography coupled to multi-angle light scattering (SEC-MALS), nuclear magnetic resonance (NMR) spectroscopy, flow cytometry, or any combination thereof.

5. The method according to claim 4, wherein the assessing is by fluorescence polarization (FP) assay.

6. The method according to claim 1, wherein the CLOCK PAS-B domain is site-specifically fluorescently-labeled at an internal site or at a terminus of the CLOCK PAS-B domain.

7. The method according to claim 6, comprising site-specifically labeling the CLOCK PAS-B domain using Sortase A.

8. The method according to claim 5, wherein the assessing comprises measuring fluorescence polarization and total fluorescence, and calculating the ratio of fluorescence polarization to total fluorescence, wherein an FP ratio below a cut-off ratio identifies the test agent as an agent that disrupts a ternary complex comprising CRY1, CLOCK, and BMAL1.

9. The method according to claim 1, wherein the test agent is selected from the group consisting of: a small molecule, an agent comprising a flavin moiety, a folate derivative, a polymer, a peptide, and a polypeptide.

10. The method according to claim 1, wherein the method further comprises:
combining:
a CRY1 protein comprising the CRY1 photolyase homology region (PHR),
a CLOCK PAS-B domain, and
a positive control agent,
under conditions suitable for CRY1-CLOCK PAS-B domain complex formation,
wherein the positive control agent inhibits CRY1-CLOCK PAS-B domain complex formation.

11. The method according to claim 10, wherein the positive control agent is a peptide encoded by Exon 11 of CRY1.

12. The method of claim 1, wherein the CLOCK PAS-B domain is covalently labeled with a fluorescent label.

13. The method of claim 12, wherein the CLOCK PAS-B domain is covalently labeled with a fluorescent label at the N-terminus of the CLOCK PAS-B domain.

* * * * *